(12) United States Patent
Skibinski et al.

(10) Patent No.: US 9,618,508 B2
(45) Date of Patent: Apr. 11, 2017

(54) FLOW CYTOMETRY ANALYSIS OF MATERIALS ADSORBED TO METAL SALTS

(75) Inventors: David Skibinski, Singapore (SG); Donatello Laera, Siena (IT); Sandra Nuti, Siena (IT); Mildred Ugozzoli, San Rafael, CA (US)

(73) Assignee: GlaxoSmithKline Biologicals SA, Rixensart (BE)

( * ) Notice: Subject to any disclaimer, the term of this patent is extended or adjusted under 35 U.S.C. 154(b) by 0 days.

(21) Appl. No.: 13/994,536

(22) PCT Filed: Dec. 14, 2011

(86) PCT No.: PCT/US2011/064938
§ 371 (c)(1),
(2), (4) Date: Aug. 23, 2013

(87) PCT Pub. No.: WO2012/082914
PCT Pub. Date: Jun. 21, 2012

(65) Prior Publication Data
US 2013/0330840 A1    Dec. 12, 2013

Related U.S. Application Data

(60) Provisional application No. 61/423,001, filed on Dec. 14, 2010.

(51) Int. Cl.
*G01N 33/537* (2006.01)
*G01N 33/84* (2006.01)
(Continued)

(52) U.S. Cl.
CPC ..... *G01N 33/56911* (2013.01); *G01N 33/537* (2013.01); *G01N 33/68* (2013.01); *G01N 33/84* (2013.01)

(58) Field of Classification Search
CPC ........... G01N 33/56911; G01N 33/537; G01N 33/68; G01N 33/84
See application file for complete search history.

(56) References Cited

U.S. PATENT DOCUMENTS 6,699,474 B1    3/2004  Cerny
2009/0317919 A1* 12/2009 Watkinson ....... G01N 33/56911
                                                    436/501

FOREIGN PATENT DOCUMENTS

EP    1649287 B1    8/2008
WO    9318150 A1    9/1993
(Continued)

OTHER PUBLICATIONS

Zhu et al. Development of a Direct Alhydrogel Formulation Immunoassay (DAFIA). Journal of Immunological Methods 344: 73-78 (2009).*

(Continued)

*Primary Examiner* — Gail R Gabel
(74) *Attorney, Agent, or Firm* — Morrison & Foerster LLP

(57) ABSTRACT

The invention utilizes the techniques and instruments which are typically used in flow cytometry (FC) as a tool for analyzing adsorbed materials. Thus the invention provides a method for analyzing a component which is adsorbed to an insoluble metal salt, comprising steps of: (i) labelling the adsorbed component with a binding reagent; and (ii) analyzing the labelled adsorbed component by flow cytometry.

20 Claims, 40 Drawing Sheets

(51) Int. Cl.
G01N 33/68 (2006.01)
G01N 33/569 (2006.01)

(56) References Cited

FOREIGN PATENT DOCUMENTS

| WO | 9527787 A1 | 10/1995 |
|---|---|---|
| WO | 9601272 A1 | 1/1996 |
| WO | 9601273 A1 | 1/1996 |
| WO | 9725429 A1 | 7/1997 |
| WO | 0037494 A2 | 6/2000 |
| WO | 0202606 A2 | 1/2002 |
| WO | 03010317 A1 | 2/2003 |
| WO | 03049762 A2 | 6/2003 |
| WO | 03097091 A2 | 11/2003 |
| WO | 2004/038417 A1 | 5/2004 |
| WO | 2005002619 A2 | 1/2005 |
| WO | 2005/022157 A1 | 3/2005 |
| WO | 2005084306 A2 | 9/2005 |
| WO | 2006089264 A2 | 8/2006 |
| WO | 2006091517 A2 | 8/2006 |
| WO | 2006138004 A2 | 12/2006 |
| WO | 2007060548 A2 | 5/2007 |
| WO | 2007110700 A2 | 10/2007 |
| WO | WO-2007/122373 A1 | 11/2007 |
| WO | 2008020330 A2 | 2/2008 |
| WO | WO-2010/119343 A2 | 10/2010 |
| WO | WO-2010/140119 A1 | 12/2010 |
| WO | WO-2011/027222 A2 | 3/2011 |

OTHER PUBLICATIONS

Morefield et al. Distribution of adsorbed antigen in mono-valent and combination vaccine, Vaccine 27: 1973-1984 (2004).*
Morefield, G.L.. et al., "Distribution of adsorbed antigen in mono-valent and combination vaccines", Vaccine, 22 (15-16):1973-1984 (2004).
Ugozzoli, M. et al., "Flow cytometry: An alternative method for direct quantification of antigens adsorbed to aluminum hydroxide adjuvant", Anal. Biochem., 418(2):224-230 (2011).
Lai, X. et al., "Determination of Adsorbed Protein Concentration in Aluminum Hydroxide Suspensions by Near-Infrared Transmittance Spectroscopy", Applied Spectroscopy, 62(7): 784-790 (2008).
Katz, J.B. et al., "In Vitro Assessment of Viral Antigen Content in Inactivated Aluminum Hydroxide Adjuvanted Vaccines", J. Virol. Methiods, 25(1): 101-108 (1989).
Zhu, D. et al., "Development of a Direct Alhydrogel Formulation Immunoassay", J. Immunol. Methods, 344(1): 73-78 (2009).
Zhu, D. et al., "Use of o-phthalaldehyde assay to determine protein contents of Alhydrogel-based vaccines", Vaccine, 27(43): 6054-6059 (2009).
Thiele, G.M. et al., "An enzyme-linked immunosorbent assay for the detection of antitetanus toxoid antibody using aluminum-absorbed coating antigen", J. Clin. Lab. Anal., 4(2): 126-129 (1990).
Cassone et al., "Opportunistic Fungi and Fungal Infections: the Challenge of a Single, General Antifungal Vaccine," Expert Rev. Vaccines, 2006, vol. 5, No. 6, pp. 859-867.
Covacci et al., "Molecular Characterization of the 128-kDa Immunodominant Antigen of Helicobacter pylori Associated with Cytotoxicity and Duodenal Ulcer," Proc. Natl. Acad. Sci. USA, 1993, vol. 90, pp. 5791-5795.
Covacci et al., "Tyrosine-Phosphorylated Bacterial Proteins: Trojan Horses for the Host Cell," J. Exp. Med., 2000, vol. 191, No. 4, pp. 587-592.
Evans et al., "Identification of Four New Prokaryotic Bacterioferritins, from Helicobacter pylori, Anabaena variabilis, Bacillus subtilis and Treponema pallidum, by Analysis of Gene Sequences," Gene, 1995, vol. 153, pp. 123-127.
Giuliani et al., "A Universal Vaccine for Serogroup B Meningococcus," Proc. Natl. Acad. Sci. USA, 2006, vol. 103, No. 29, pp. 10834-10839.
Harper et al. "Efficacy of a Bivalent L1 Virus-Like Particle Vaccine in Prevention of Infection with Human Papillomavirus Types 16 and 18 in Young Women: a Randomised Controlled Trial," The Lancet, 2004, vol. 364, pp. 1757-1765.
Hem et al., "Relationship between Physical and Chemical Properties of Aluminum-Containing Adjuvants and Immunopotentiation," Expert Rev. Vaccines, 2007, vol. 6, No. 5, pp. 685-698.
Keitel et al., "Increasing Doses of Purified Influenza Virus Hemagglutinin and Subvirion Vaccines Enhance Antibody Responses in the Elderly," Clin. Diagn. Lab. Immunol., 1996, vol. 3, No. 5, pp. 507-510.
Marchetti et al., "Protection against Helicobacter pylori Infection in Mice by Intragastric Vaccination with H. pylori Antigents is Achieved Using a Non-Toxic Mutant of E. coli Heat-Labile Enterotoxin (LT) as Adjuvant," Vaccine, 1998, vol. 16, No. 1, pp. 33-37.
Matheis et al., "The Role of the Adsorption Process for Production and Control Combined Adsorbed Vaccines," Vaccine, 2002, vol. 20, pp. 67-73.
The Molecular Probes Handbook—A Guide to Fluorescent Probes and Labeling Technologies, 2010, 11th Edition, Invitrogen.
Morbidity and Mortality Weekly Report (MMWR), 1998, vol. 47, No. 1, pp. 12, 19.
Remington: The Science and Practice of Pharmacy, 2000, 20th Edition, Lippincott Williams & Wilkins, ISBN:0683306472.
Telford et al., "Gene Structure of the Helicobacter pylori Cytotoxin and Evidence of Its Key Role in Gastric Disease," J. Exp. Med., 1994, vol. 179, pp. 1653-1658.
Treanor et al., "Evaluation of a Recombinant Hemagglutinin Expressed in Insect Cells as an Influenza Vaccine in Young and Elderly Adults," J. Infect. Dis., 1996, vol. 173, pp. 1467-1470.
Tummuru et al., "Cloning and Expression of a High-Molecular-Mass Major Antigen of Helicobacter pylori: Evidence of Linkage to Cytotoxin Production," Infect. Immun., 1994, vol. 61, pp. 1799-1809.
Vaccine Design—the Subunit and Adjuvant Approach, 1995, Springer, ISBN:030644867X.
Bernd (2009). "In Deutschland zugelassene Impfstoffe mit Aluminium-Adjuvans", Acta Crystallographica Section A, pp. 14-15, Retrieved Apr. 4, 2016 from <http://www.bermibs.de/fileadmin/pdf/impfen-sinn_oder_unsinn/impfstoffe_mit_aluminium-adjuvans.pdf>.
Maraskovsky et al. (2004). "NY-ESO-1 protein formulated in ISCOMATRIX adjuvant is a potent anticancer vaccine inducing both humoral and CD8+ t-cell-mediated immunity and protection against NY-ESO-1+ tumors," Clin Cancer Res. 10(8):2879-90.
Summons to attend oral proceedings, dated Dec. 11, 2015, filed during examination of EP2652511, 9 pages.

* cited by examiner

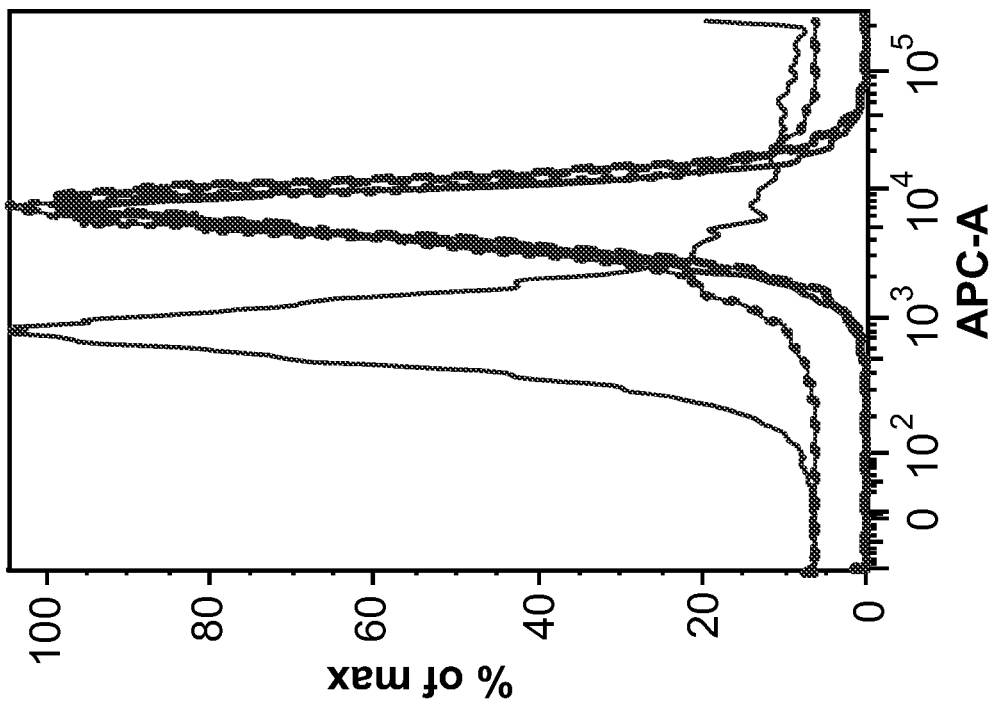
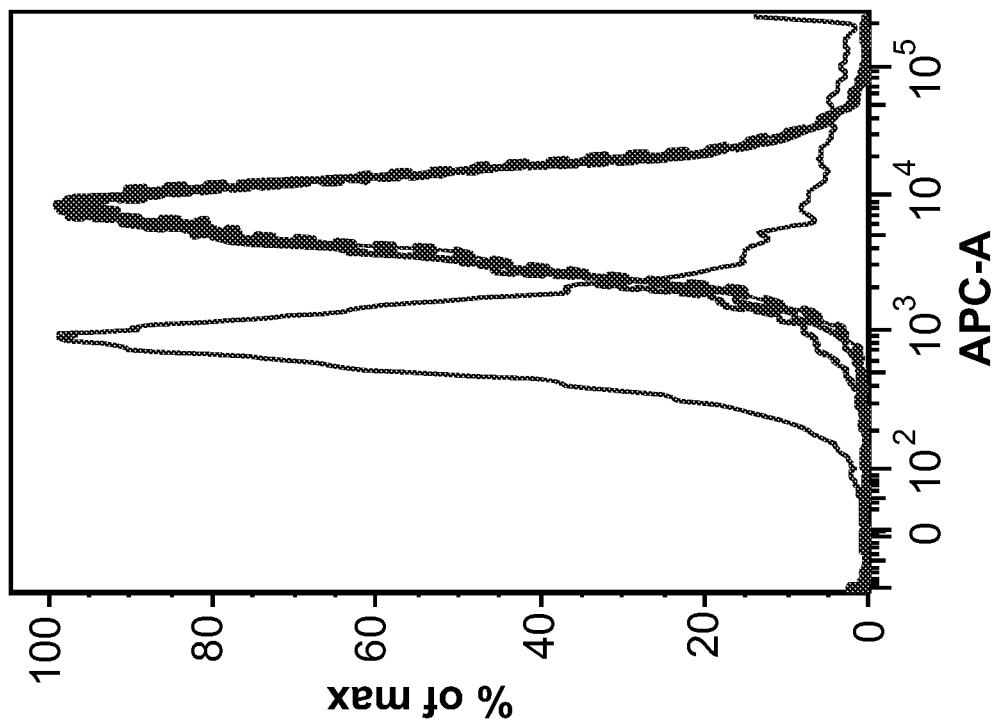

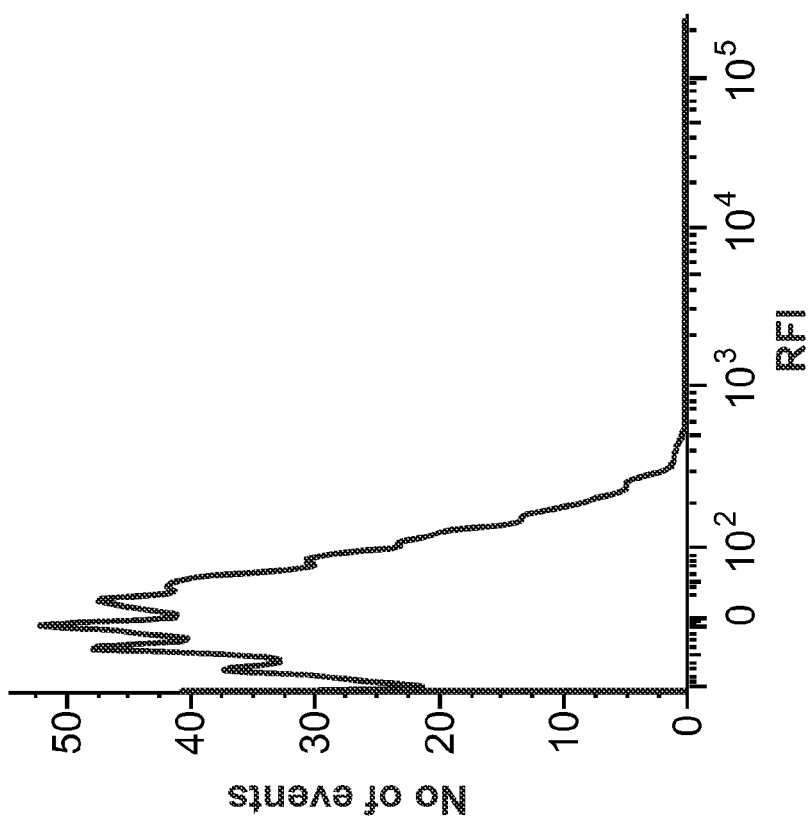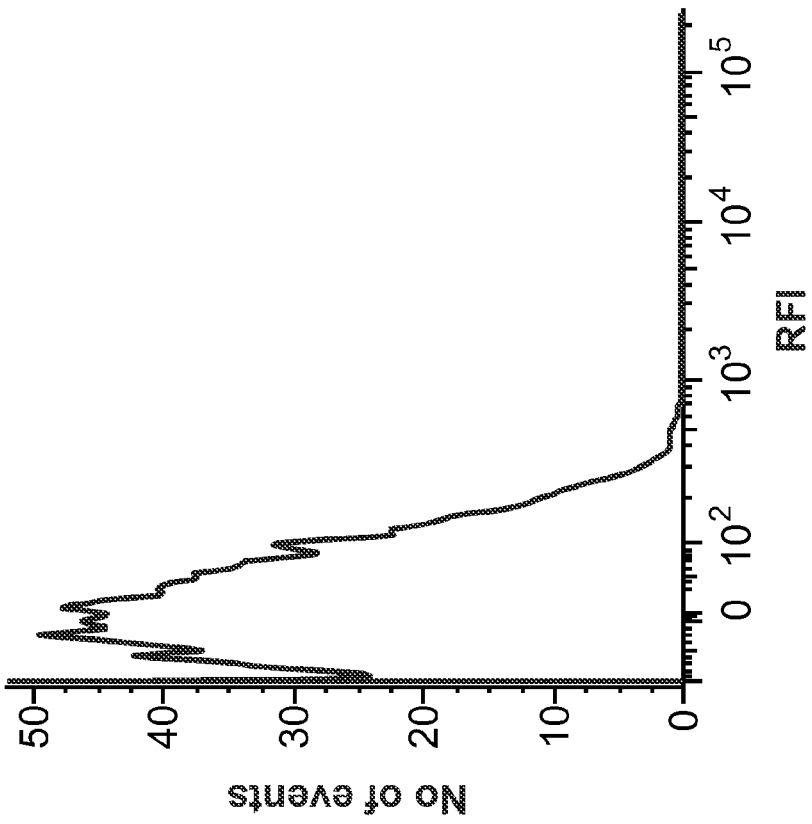

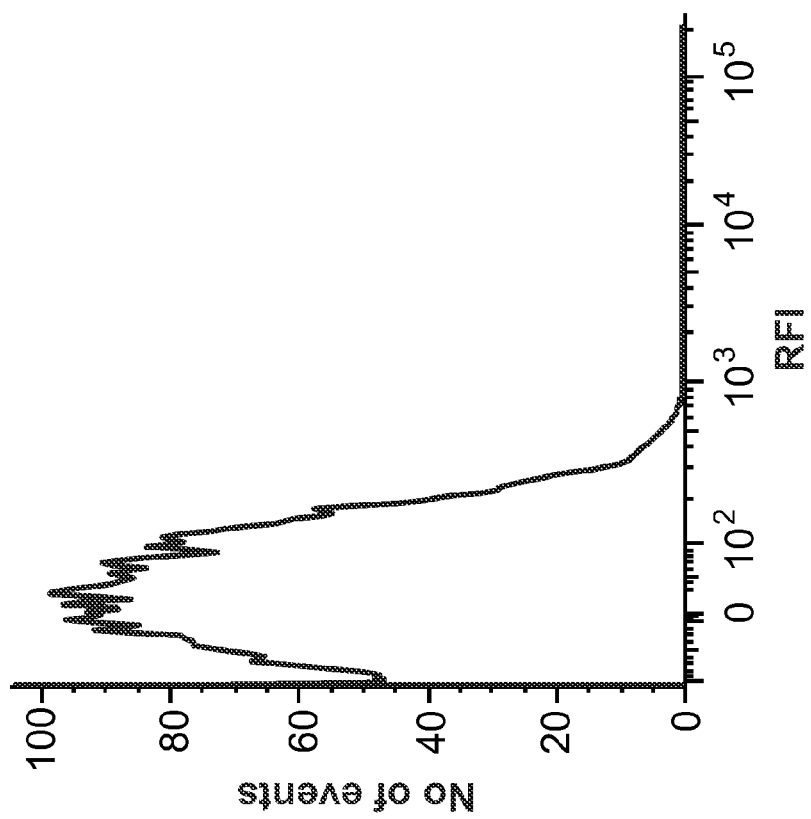
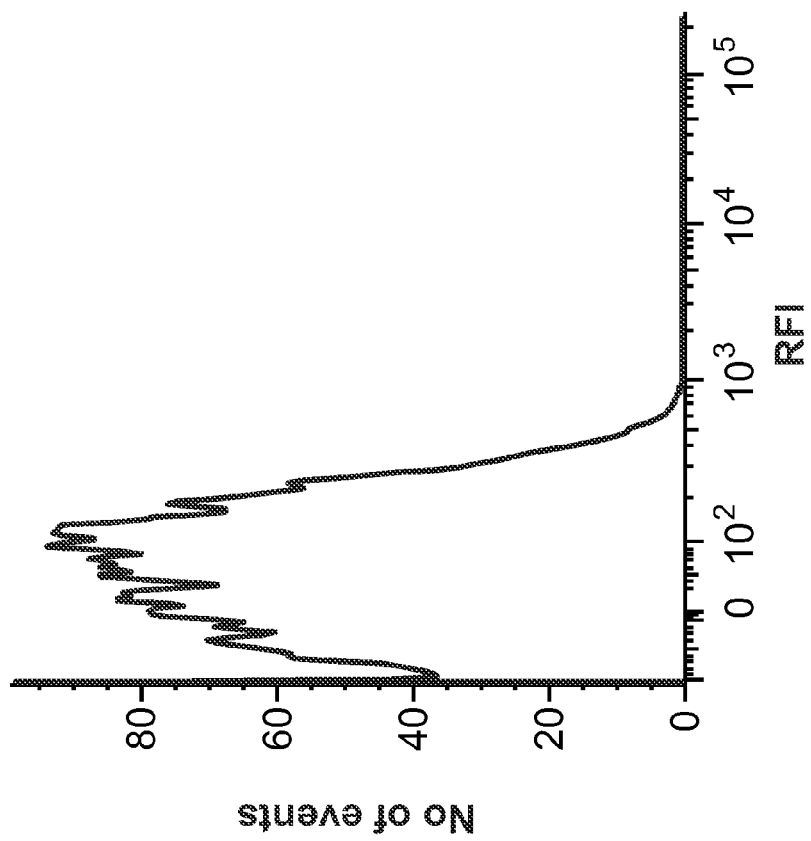

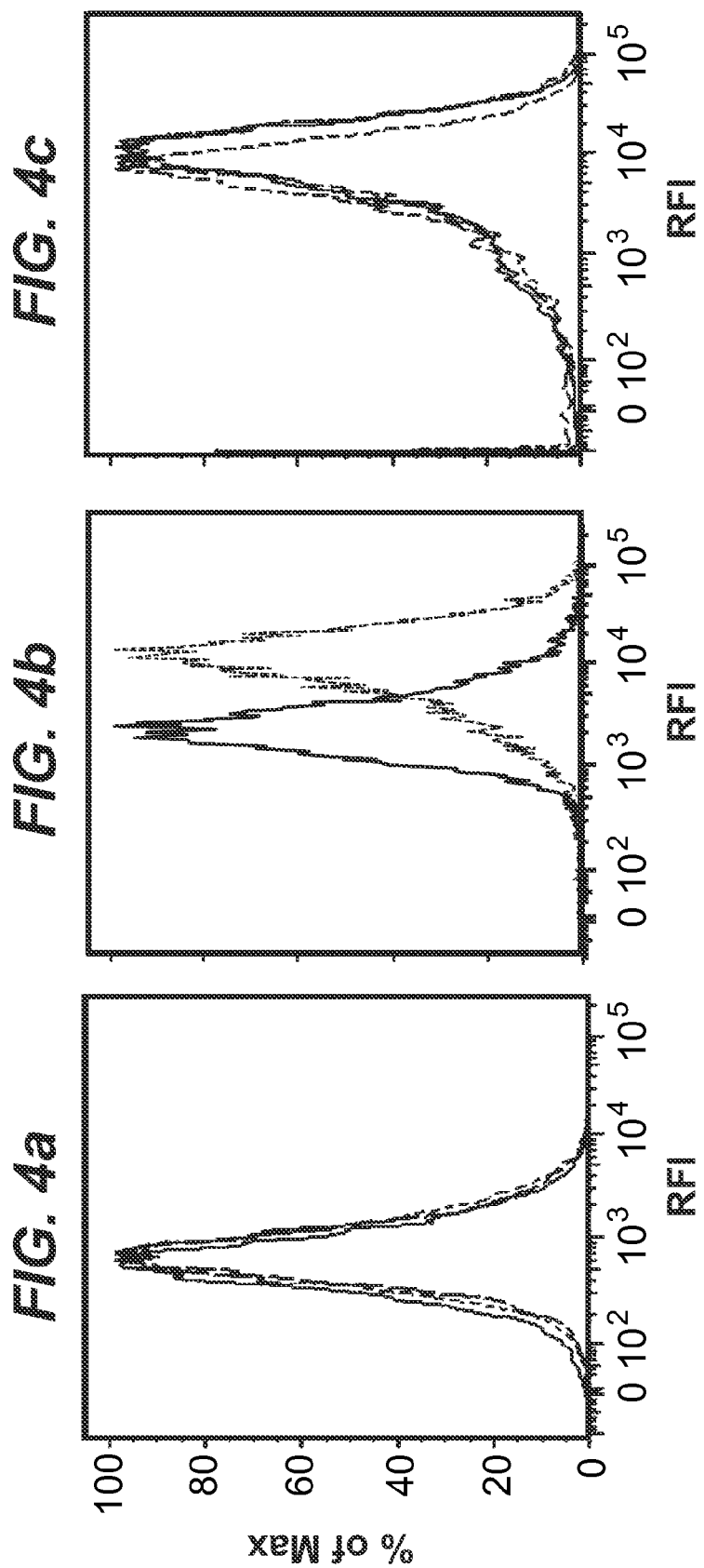

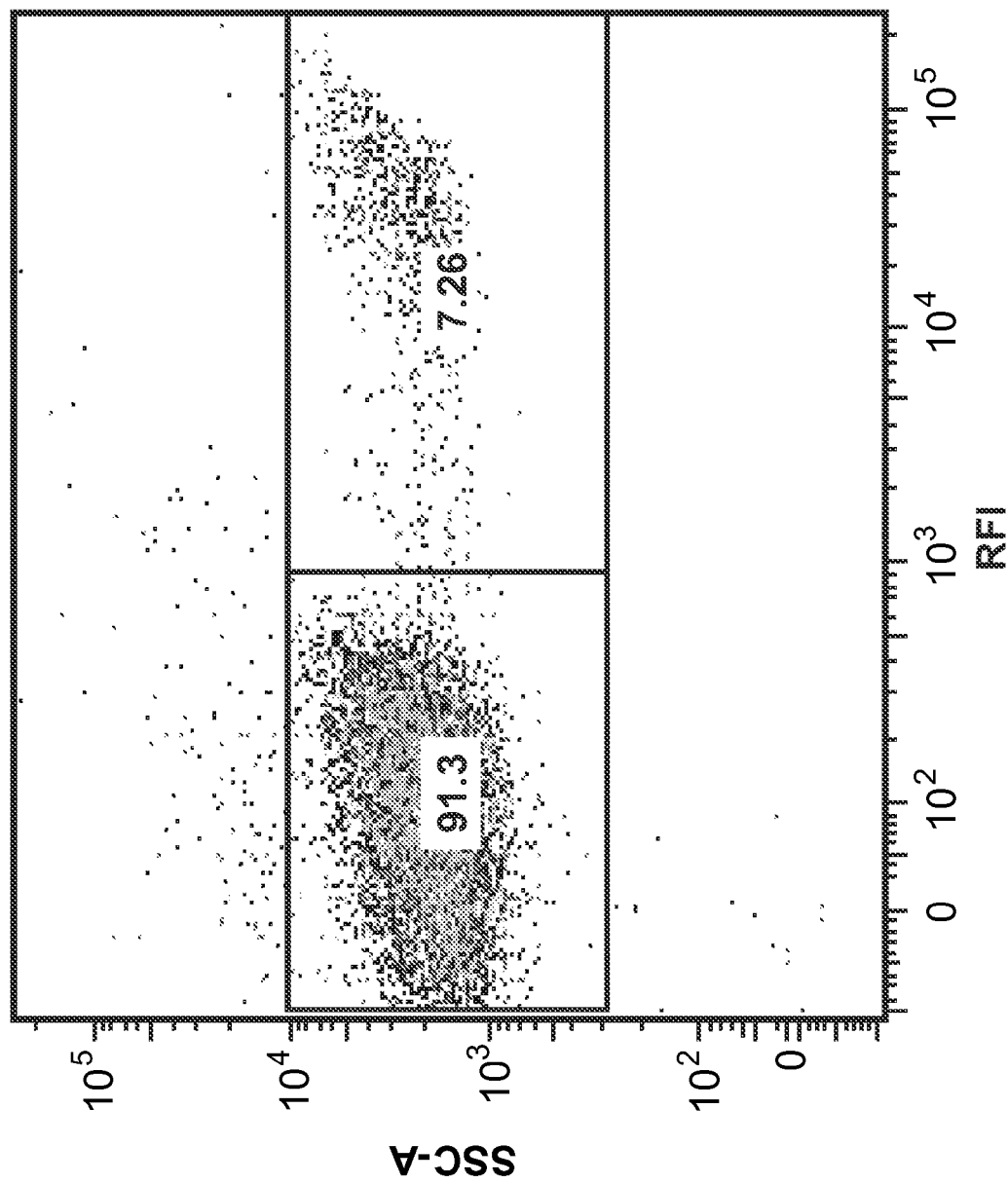

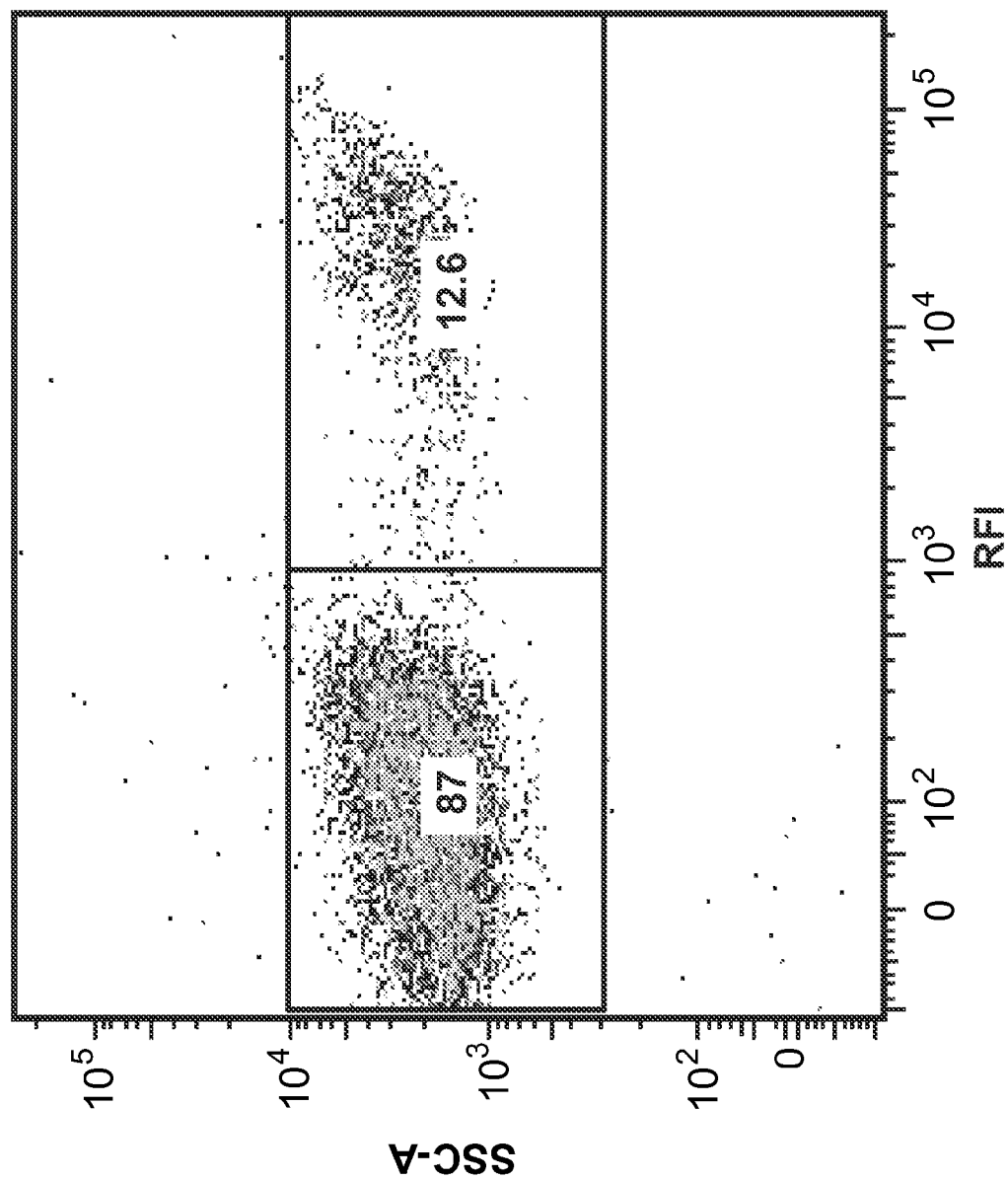

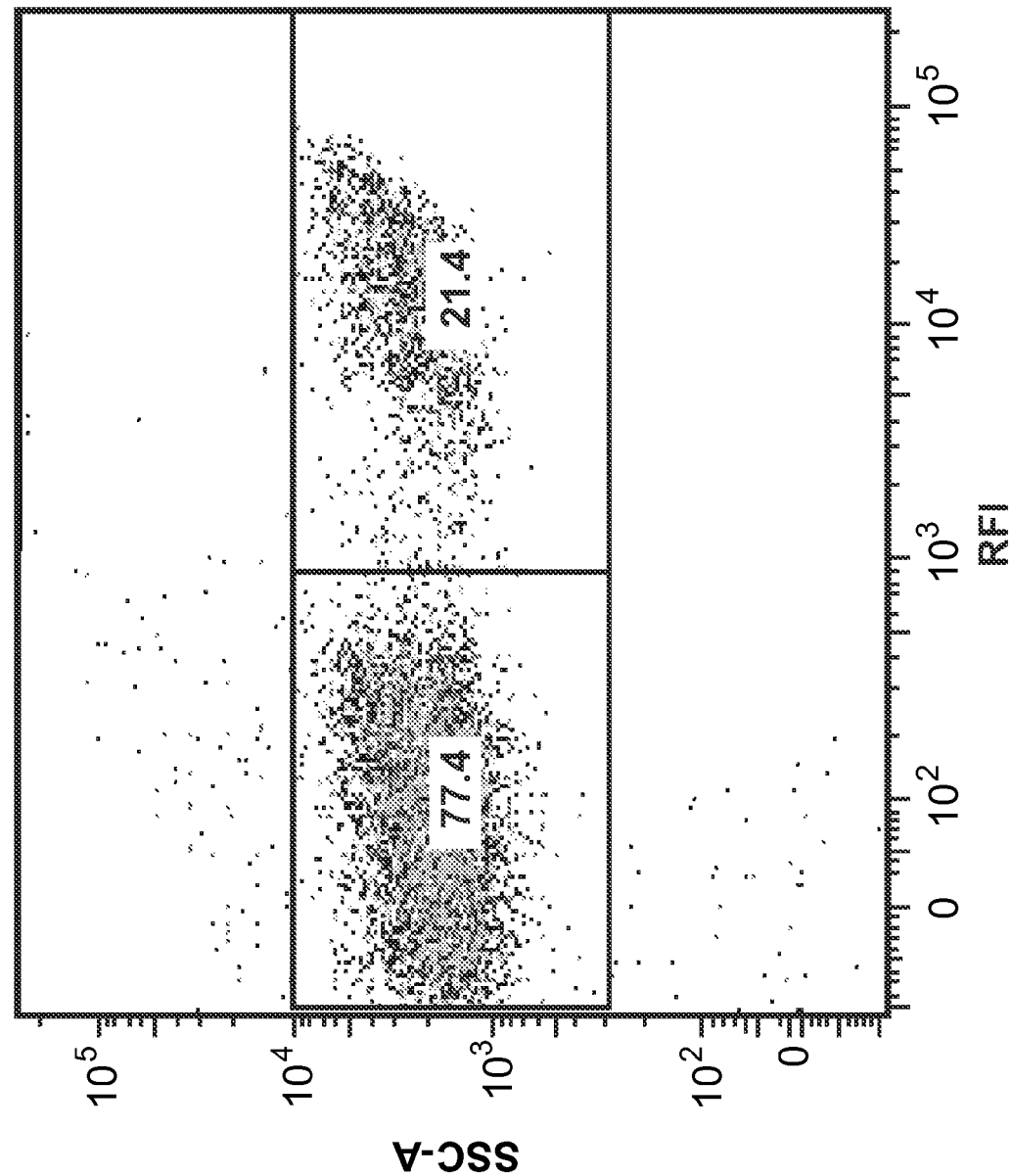

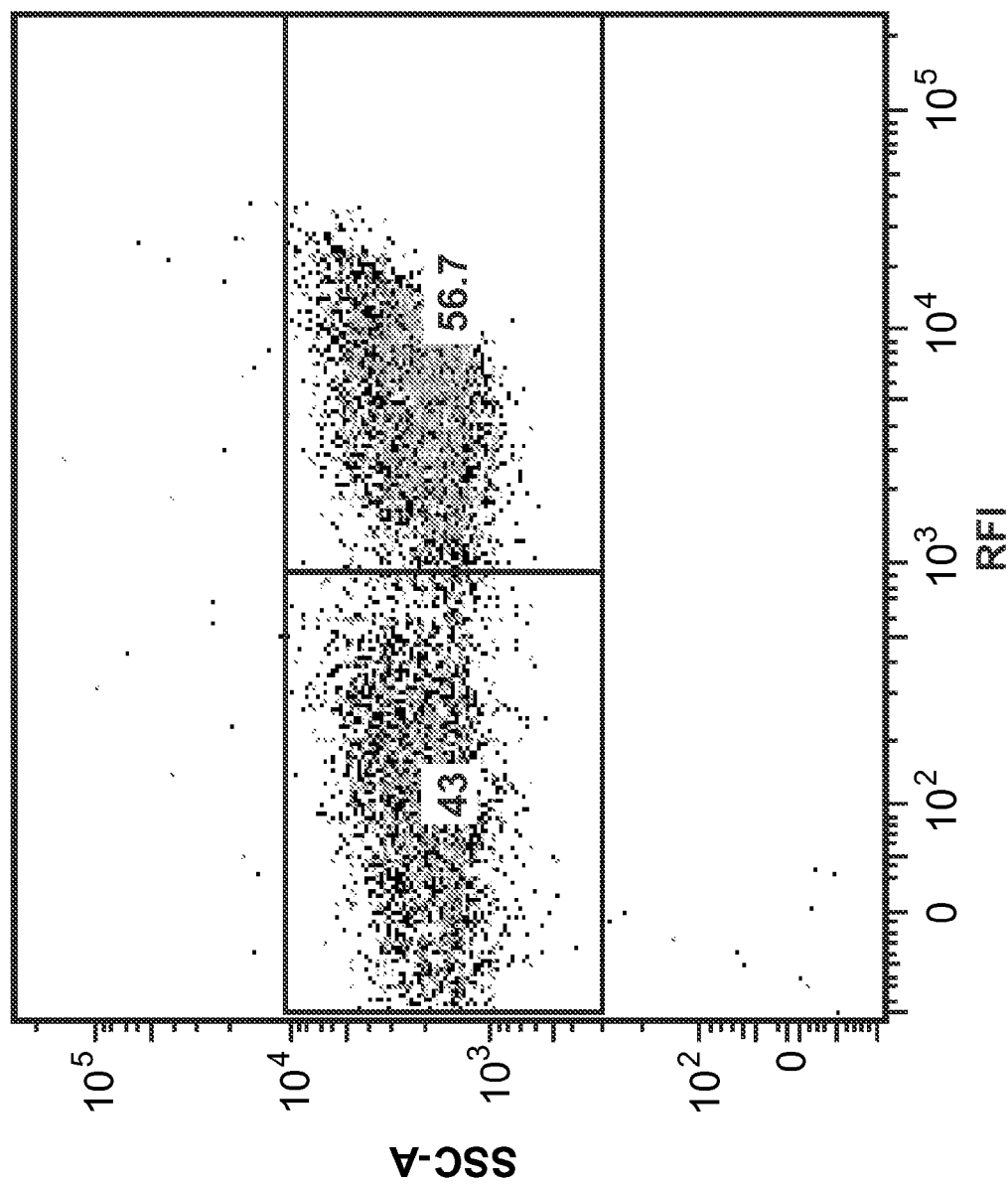

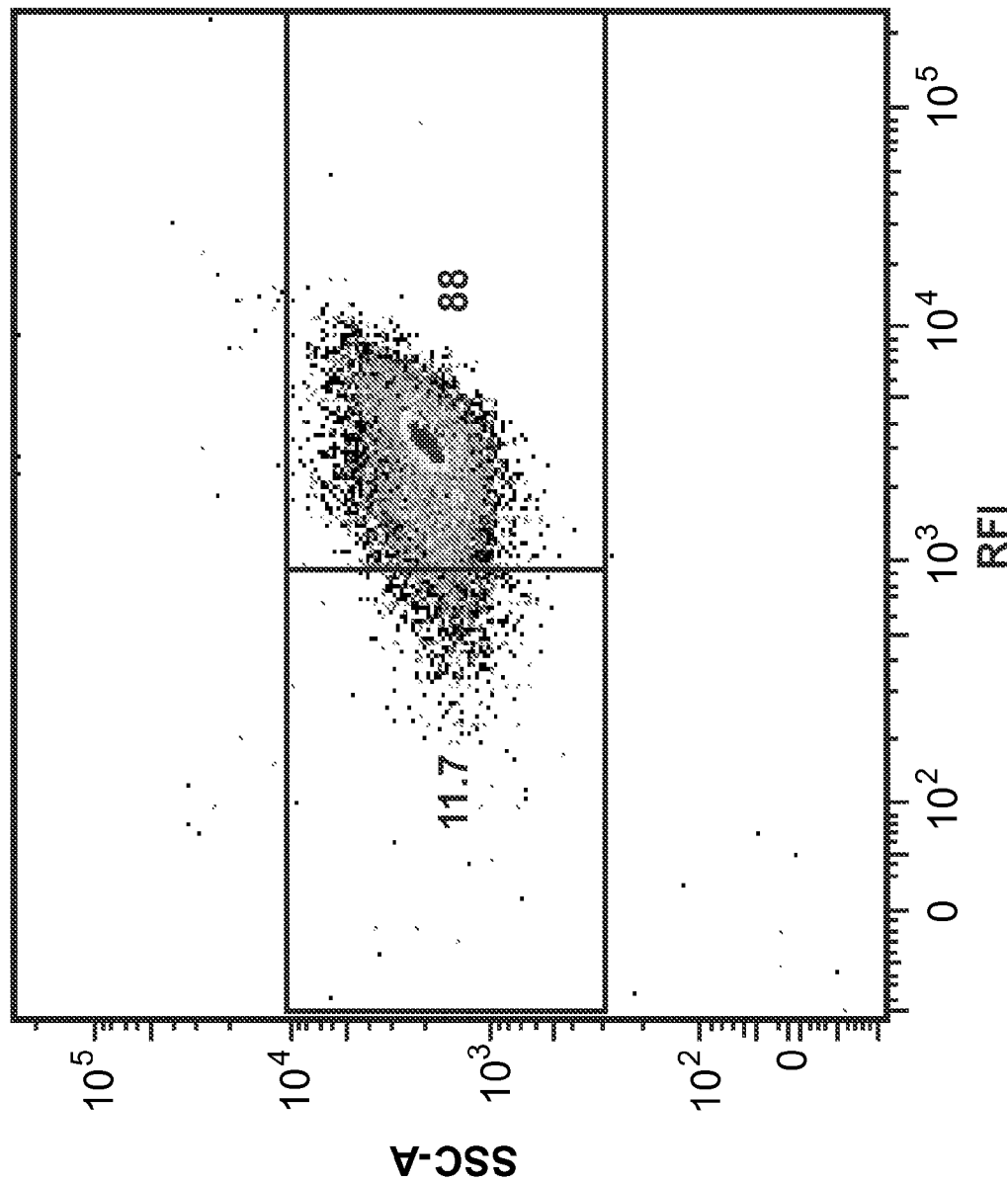

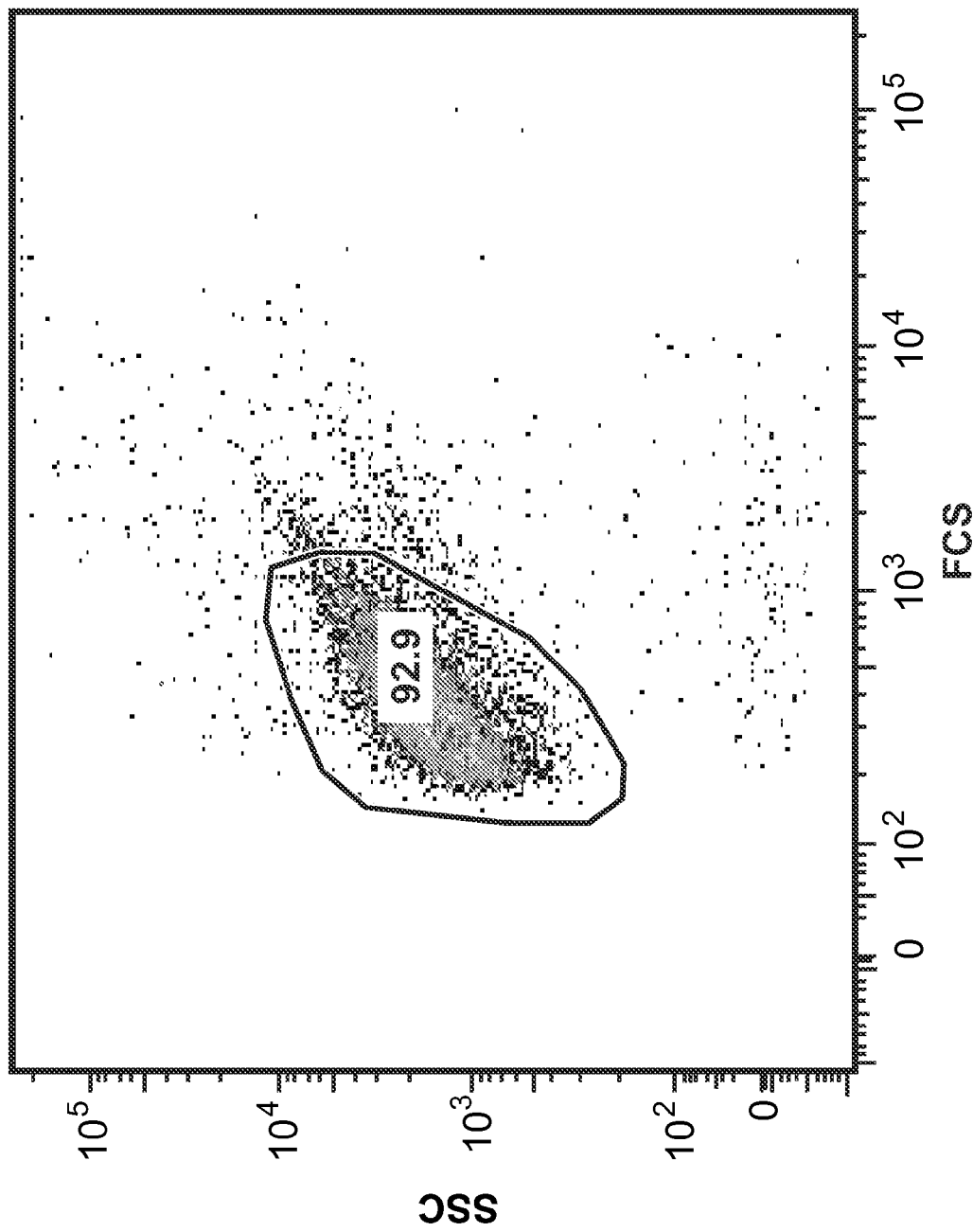

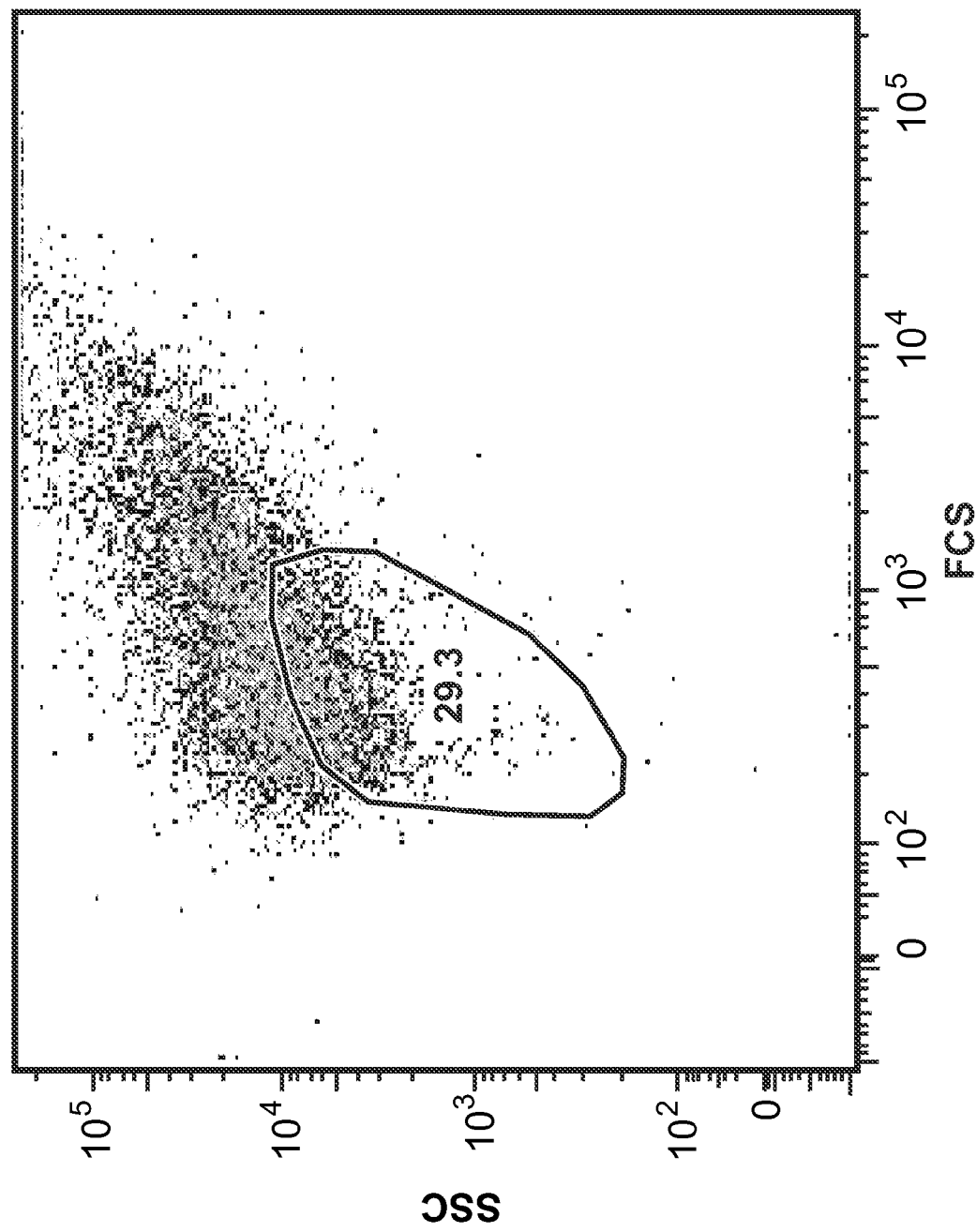

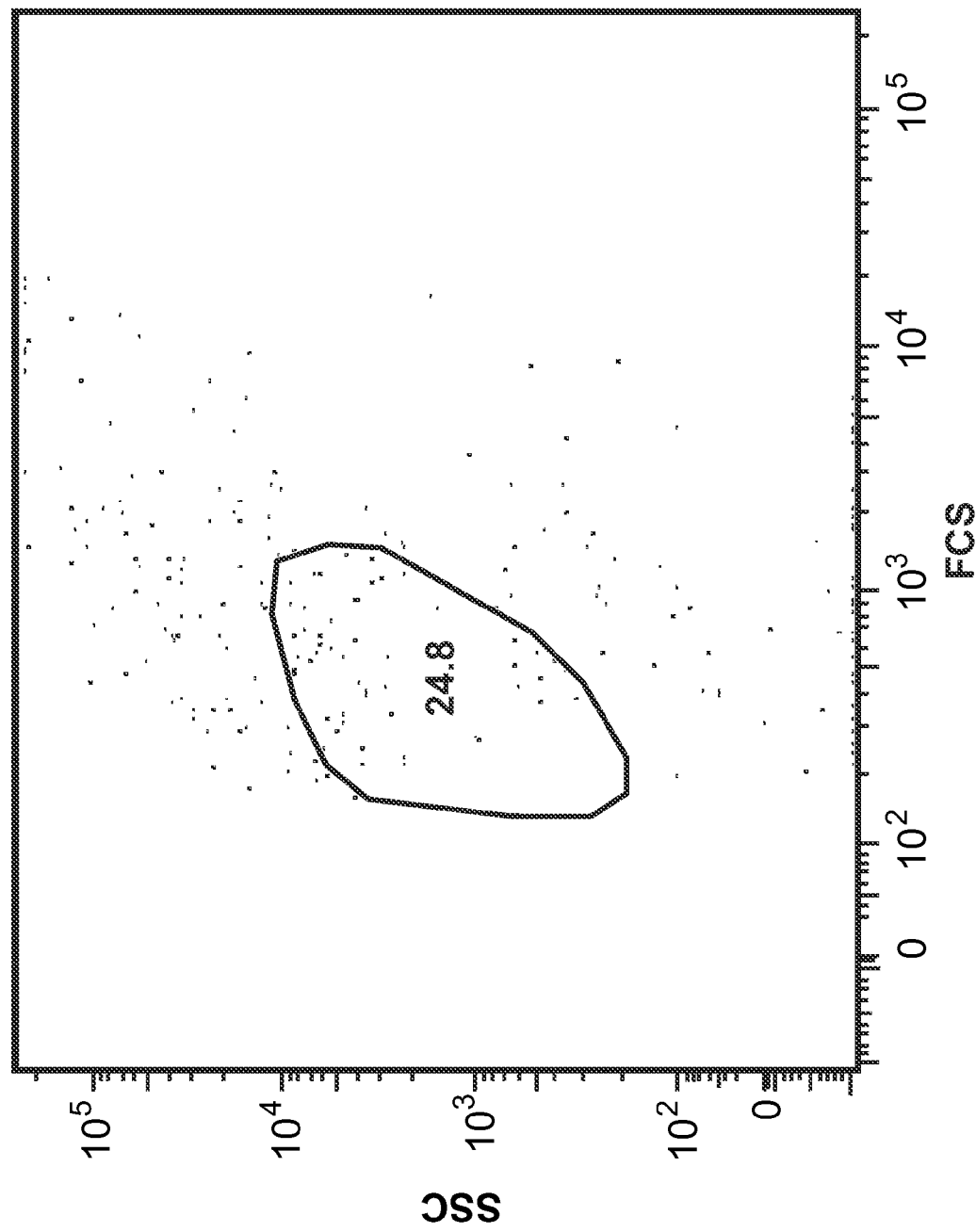

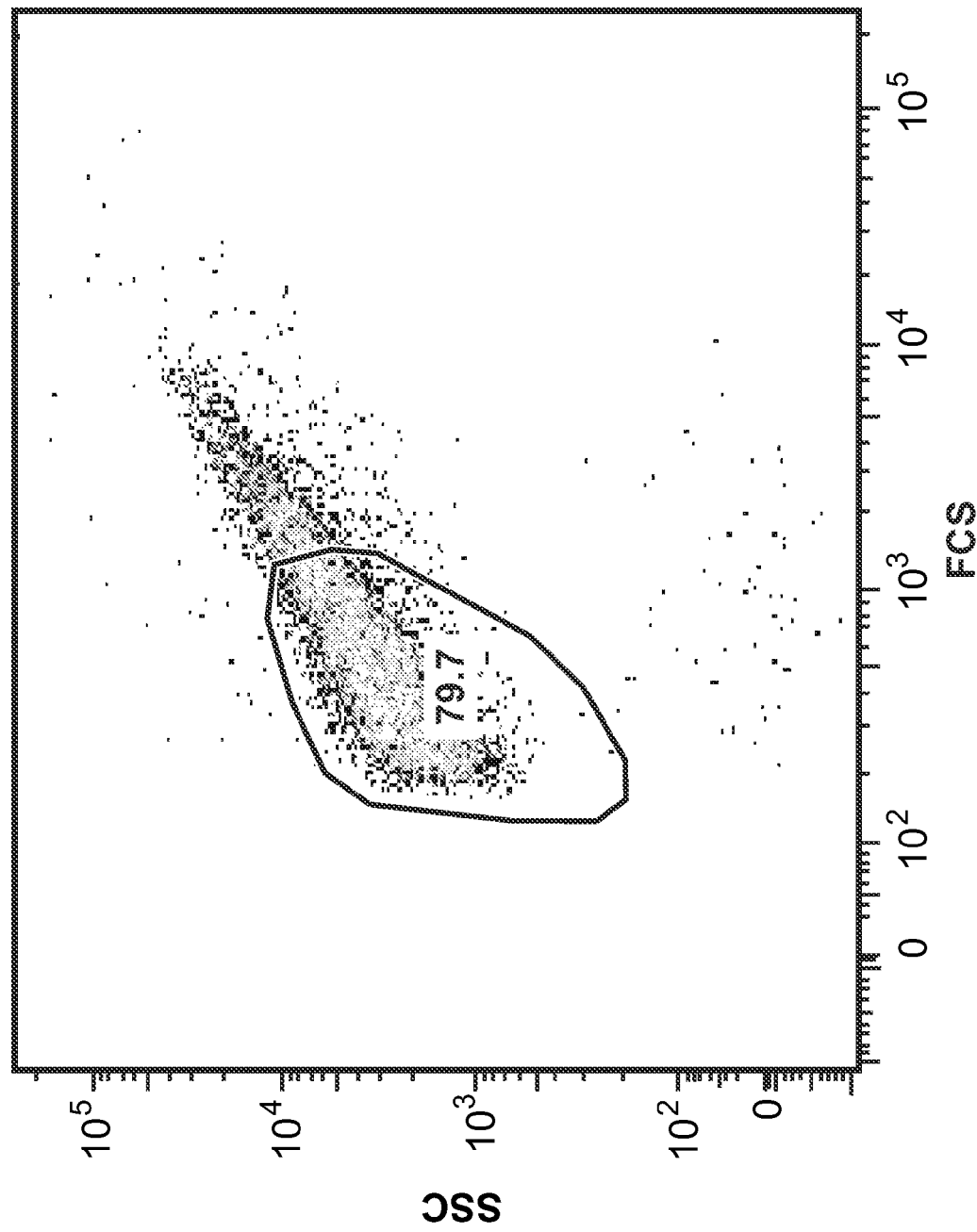

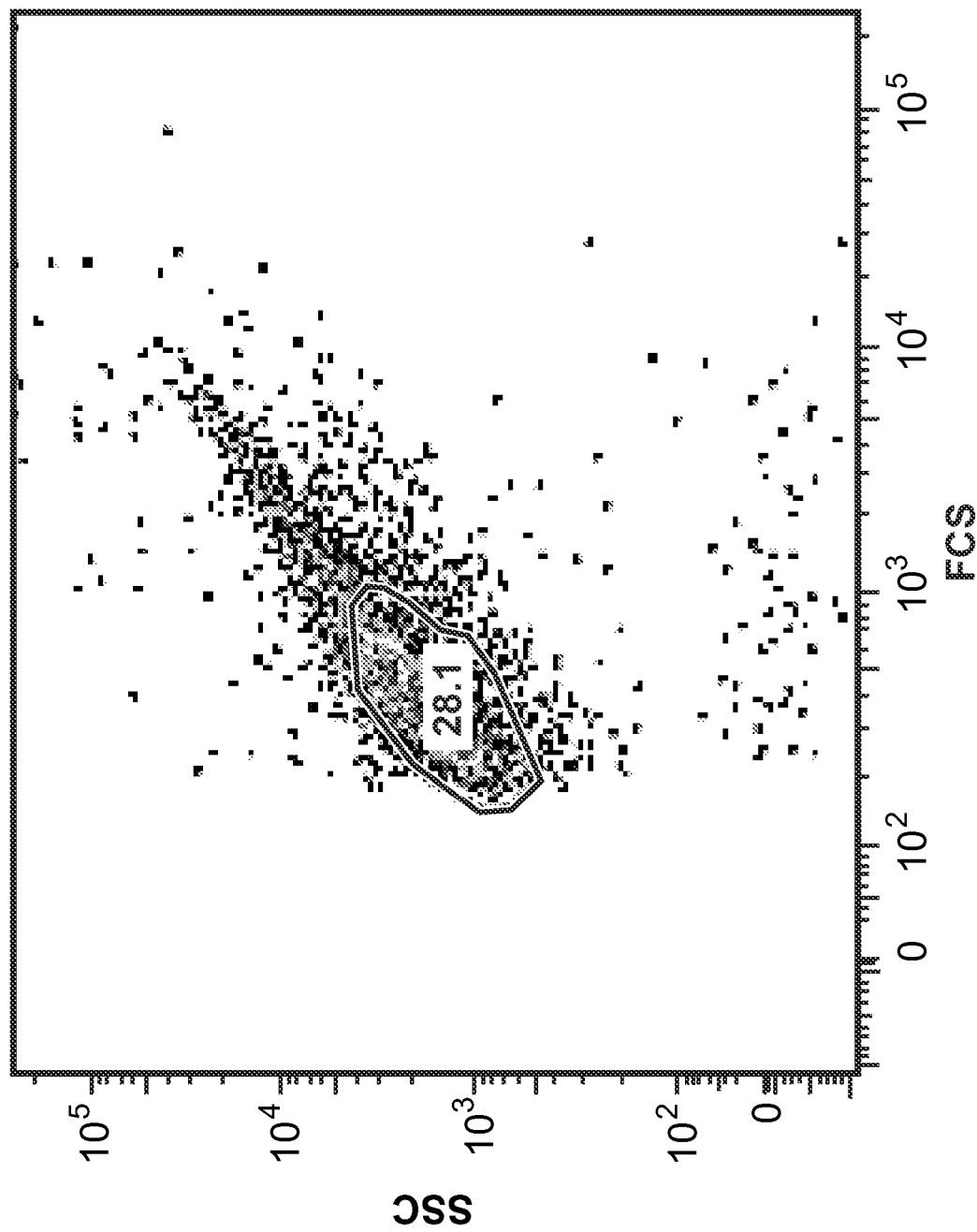

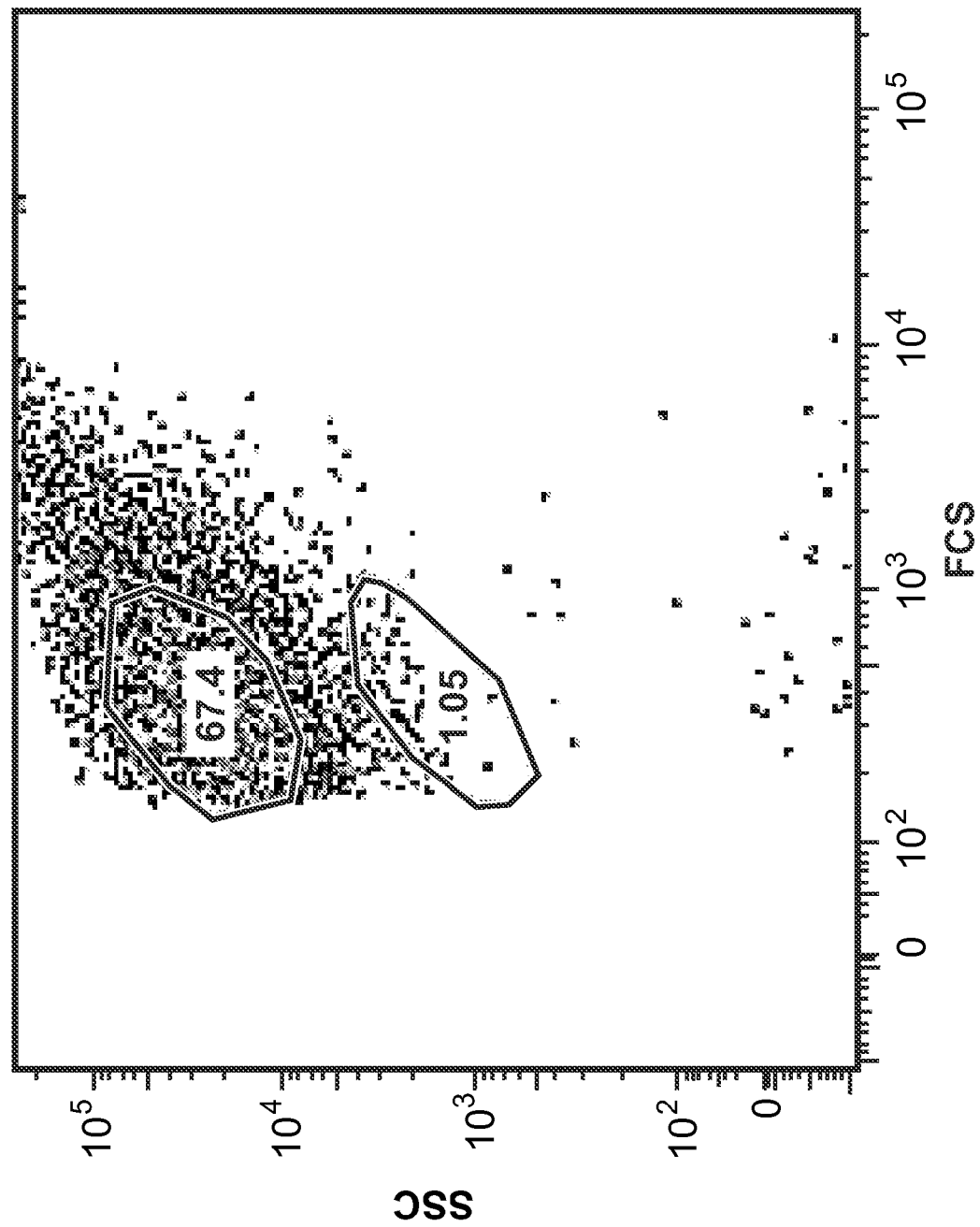

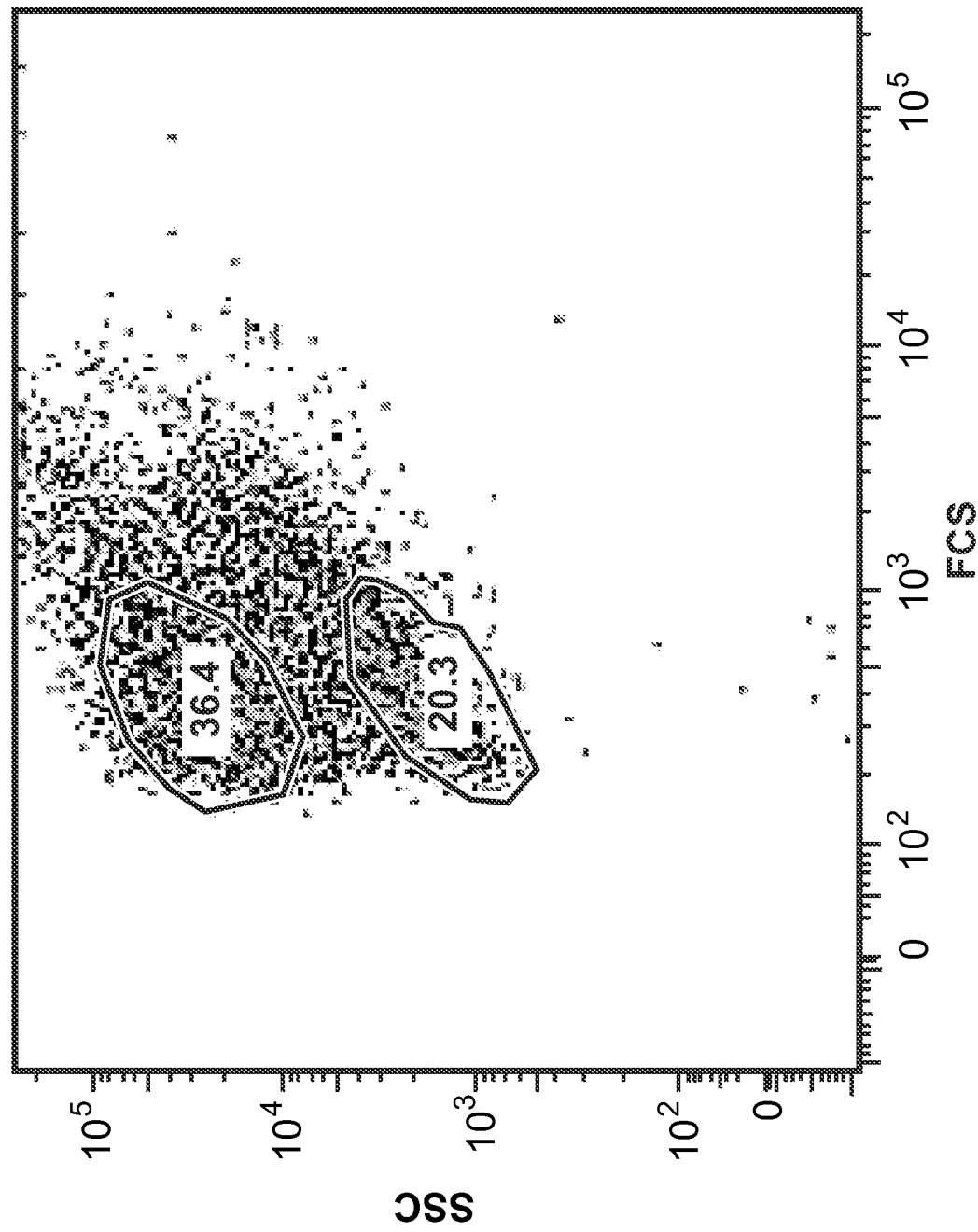

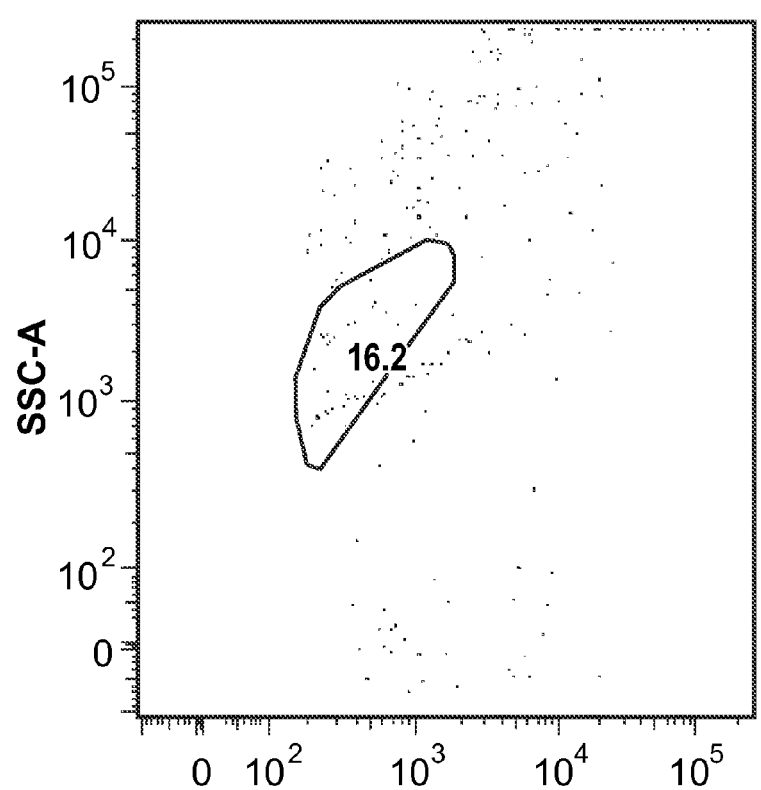
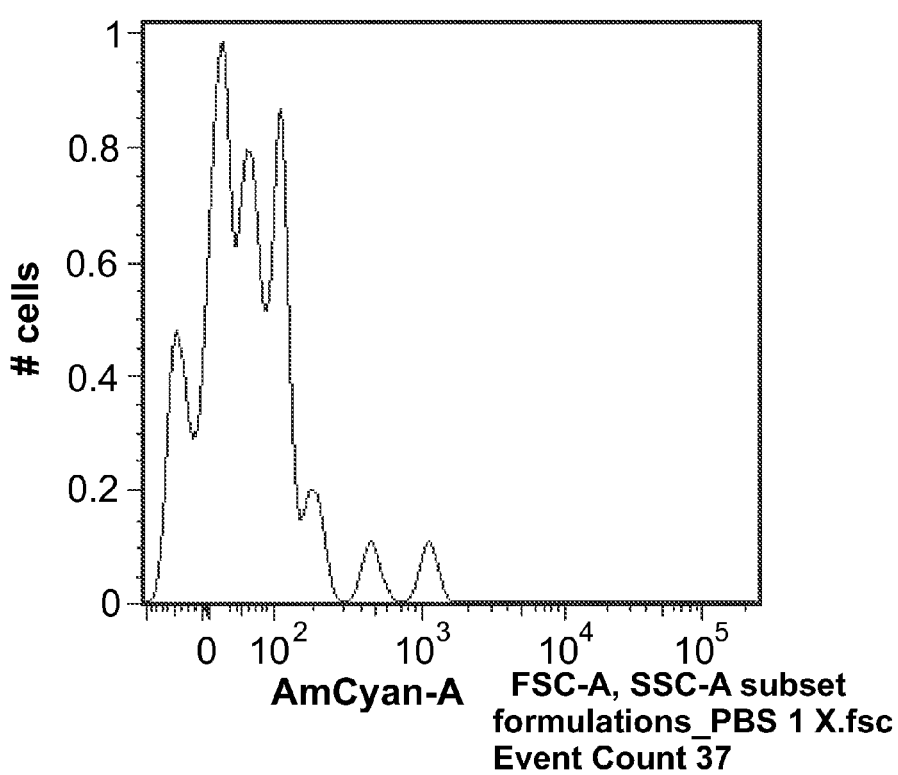
FIG. 15a

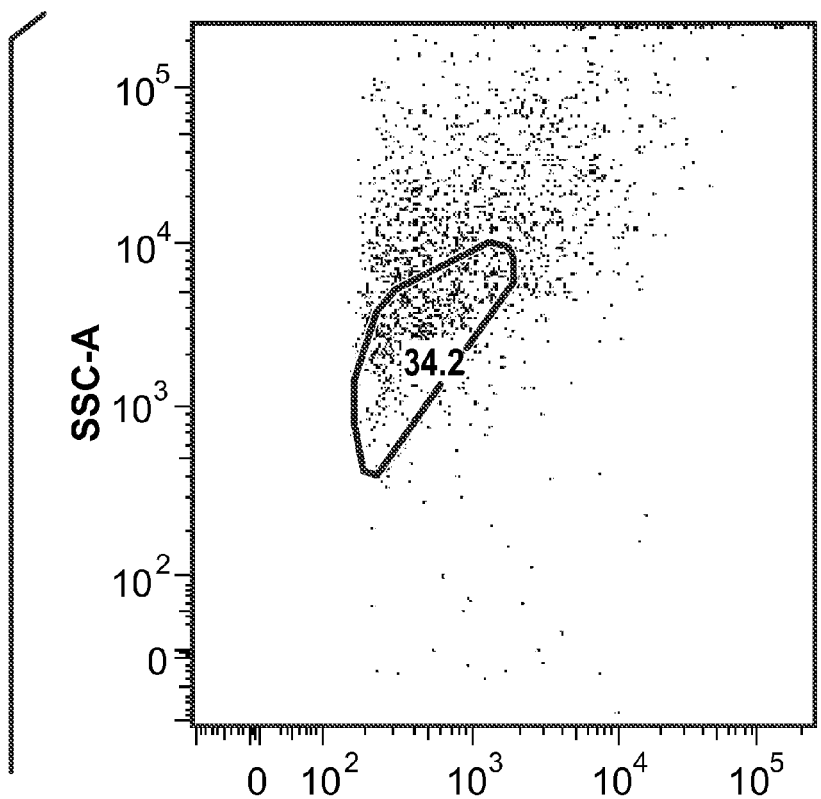
FIG. 15b
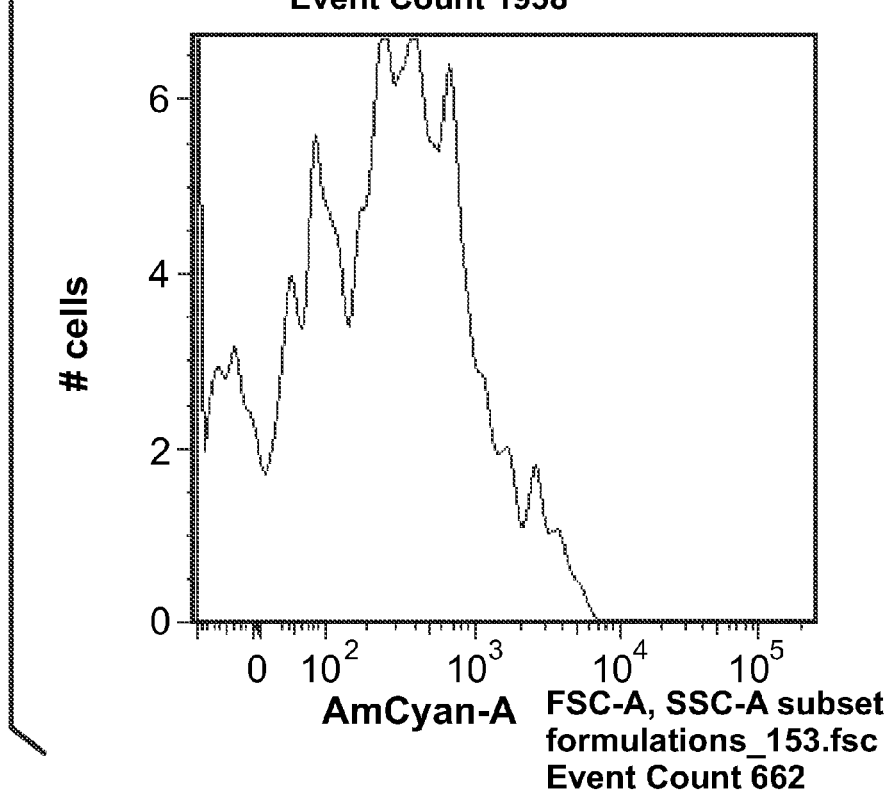

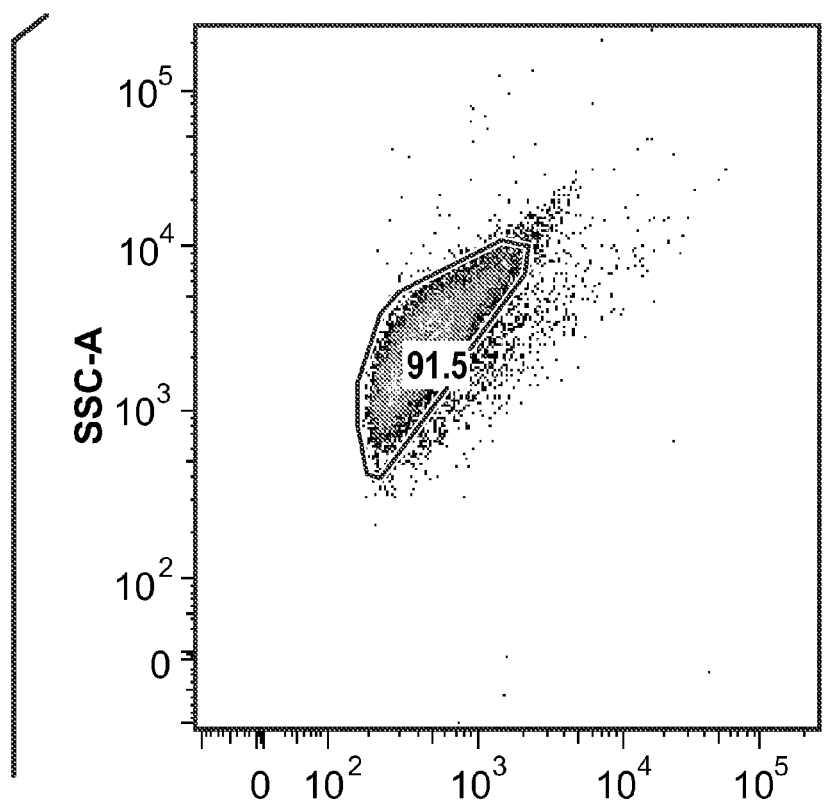
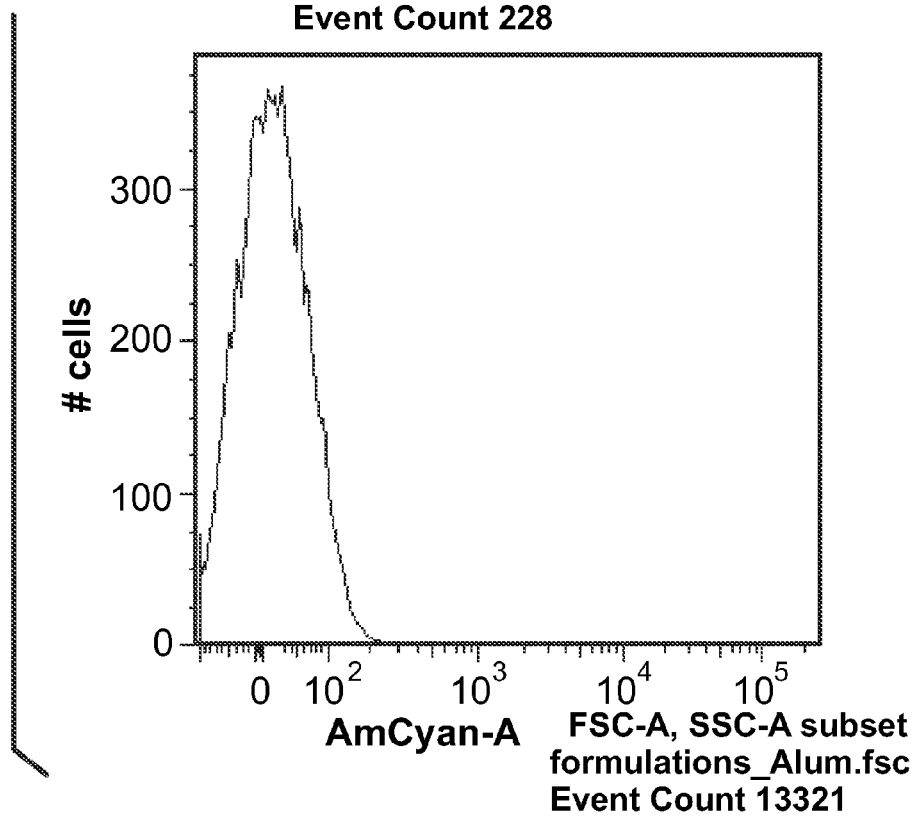
FIG. 15c

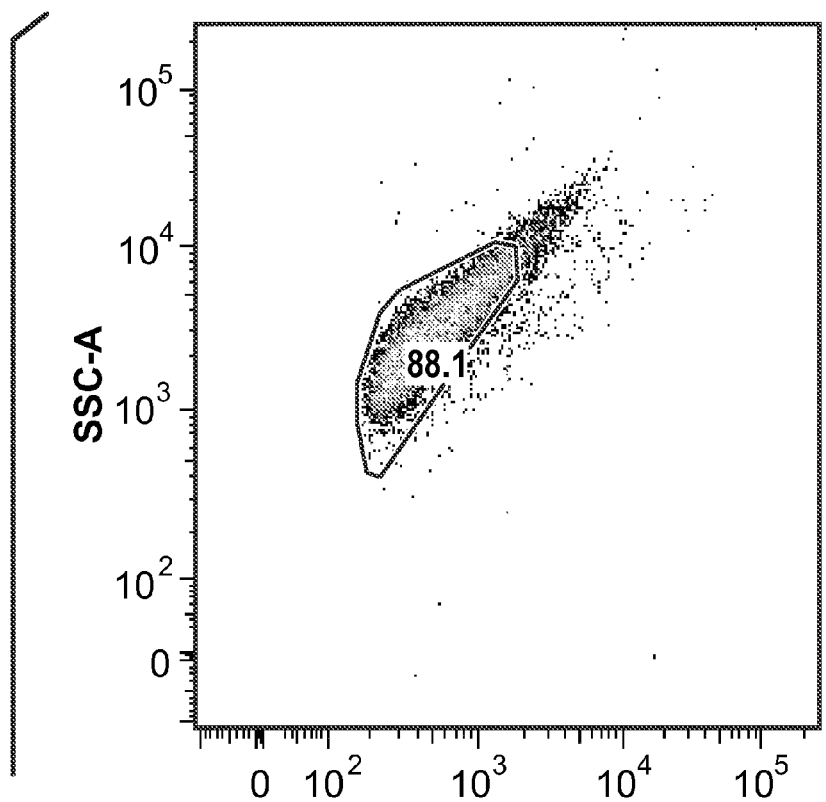
FIG. 15d
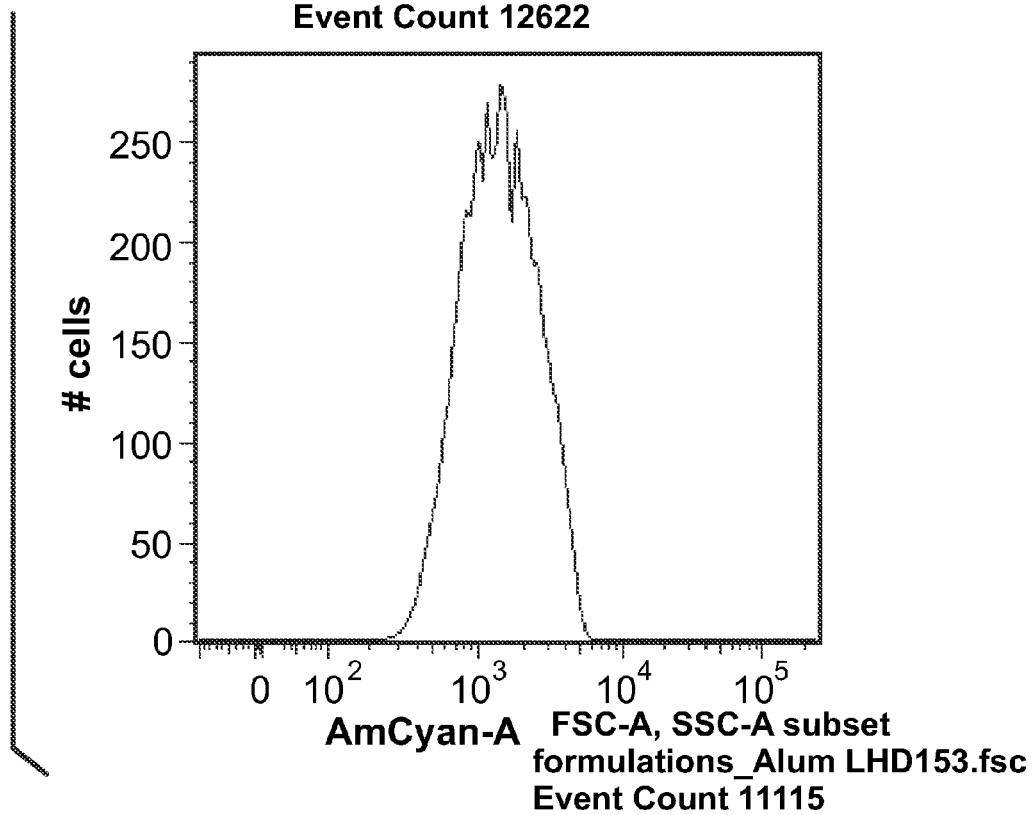

SEQUENCE LISTING

<160> NUMBER OF SEQ ID NOS: 5

<210> SEQ ID NO 1
<211> LENGTH: 327
<212> TYPE: PRT
<213> ORGANISM: Artificial Sequence
<220> FEATURE:
<223> OTHER INFORMATION: Immunogen for Neisseria meningitidis

<400> SEQUENCE: 1

Ala Thr Asn Asp Asp Val Lys Lys Ala Ala Thr Val Ala Ile Ala
1               5                   10                  15

Ala Ala Tyr Asn Asn Gly Gln Glu Ile Asn Gly Phe Lys Ala Gly Glu

-continued

```
                20                  25                  30
Thr Ile Tyr Asp Ile Asp Glu Asp Gly Thr Ile Thr Lys Lys Asp Ala
            35                  40                  45

Thr Ala Ala Asp Val Glu Ala Asp Asp Phe Lys Gly Leu Gly Leu Lys
        50                  55                  60

Lys Val Val Thr Asn Leu Thr Lys Thr Val Asn Glu Asn Lys Gln Asn
65                  70                  75                  80

Val Asp Ala Lys Val Lys Ala Ala Glu Ser Glu Ile Glu Lys Leu Thr
                85                  90                  95

Thr Lys Leu Ala Asp Thr Asp Ala Ala Leu Ala Asp Thr Asp Ala Ala
            100                 105                 110

Leu Asp Ala Thr Thr Asn Ala Leu Asn Lys Leu Gly Glu Asn Ile Thr
        115                 120                 125

Thr Phe Ala Glu Glu Thr Lys Thr Asn Ile Val Lys Ile Asp Glu Lys
    130                 135                 140

Leu Glu Ala Val Ala Asp Thr Val Asp Lys His Ala Glu Ala Phe Asn
145                 150                 155                 160

Asp Ile Ala Asp Ser Leu Asp Glu Thr Asn Thr Lys Ala Asp Glu Ala
                165                 170                 175

Val Lys Thr Ala Asn Glu Ala Lys Gln Thr Ala Glu Glu Thr Lys Gln
            180                 185                 190

Asn Val Asp Ala Lys Val Lys Ala Ala Glu Thr Ala Ala Gly Lys Ala
        195                 200                 205

Glu Ala Ala Ala Gly Thr Ala Asn Thr Ala Ala Asp Lys Ala Glu Ala
    210                 215                 220

Val Ala Ala Lys Val Thr Asp Ile Lys Ala Asp Ile Ala Thr Asn Lys
225                 230                 235                 240

Asp Asn Ile Ala Lys Lys Ala Asn Ser Ala Asp Val Tyr Thr Arg Glu
                245                 250                 255

Glu Ser Asp Ser Lys Phe Val Arg Ile Asp Gly Leu Asn Ala Thr Thr
            260                 265                 270

Glu Lys Leu Asp Thr Arg Leu Ala Ser Ala Glu Lys Ser Ile Ala Asp
        275                 280                 285

His Asp Thr Arg Leu Asn Gly Leu Asp Lys Thr Val Ser Asp Leu Arg
    290                 295                 300

Lys Glu Thr Arg Gln Gly Leu Ala Glu Gln Ala Ala Leu Ser Gly Leu
305                 310                 315                 320

Phe Gln Pro Tyr Asn Val Gly
                325

<210> SEQ ID NO 2
<211> LENGTH: 644
<212> TYPE: PRT
<213> ORGANISM: Artificial Sequence
<220> FEATURE:
<223> OTHER INFORMATION: Immunogen for Neisseria meningitidis - fusion
      protein

<400> SEQUENCE: 2

Met Ala Ser Pro Asp Val Lys Ser Ala Asp Thr Leu Ser Lys Pro Ala
1               5                   10                  15

Ala Pro Val Val Ser Glu Lys Glu Thr Glu Ala Lys Glu Asp Ala Pro
            20                  25                  30

Gln Ala Gly Ser Gln Gly Gln Gly Ala Pro Ser Ala Gln Gly Gly Gln
        35                  40                  45
```

```
Asp Met Ala Ala Val Ser Glu Glu Asn Thr Gly Asn Gly Gly Ala Ala
    50                  55                  60

Ala Thr Asp Lys Pro Lys Asn Glu Asp Glu Gly Ala Gln Asn Asp Met
65                  70                  75                  80

Pro Gln Asn Ala Ala Asp Thr Asp Ser Leu Thr Pro Asn His Thr Pro
                85                  90                  95

Ala Ser Asn Met Pro Ala Gly Asn Met Glu Asn Gln Ala Pro Asp Ala
            100                 105                 110

Gly Glu Ser Glu Gln Pro Ala Asn Gln Pro Asp Met Ala Asn Thr Ala
        115                 120                 125

Asp Gly Met Gln Gly Asp Pro Ser Ala Gly Glu Asn Ala Gly
    130                 135                 140

Asn Thr Ala Ala Gln Gly Thr Asn Gln Ala Glu Asn Asn Gln Thr Ala
145                 150                 155                 160

Gly Ser Gln Asn Pro Ala Ser Ser Thr Asn Pro Ser Ala Thr Asn Ser
                165                 170                 175

Gly Gly Asp Phe Gly Arg Thr Asn Val Gly Asn Ser Val Val Ile Asp
            180                 185                 190

Gly Pro Ser Gln Asn Ile Thr Leu Thr His Cys Lys Gly Asp Ser Cys
        195                 200                 205

Ser Gly Asn Asn Phe Leu Asp Glu Glu Val Gln Leu Lys Ser Glu Phe
    210                 215                 220

Glu Lys Leu Ser Asp Ala Asp Lys Ile Ser Asn Tyr Lys Lys Asp Gly
225                 230                 235                 240

Lys Asn Asp Gly Lys Asn Asp Lys Phe Val Gly Leu Val Ala Asp Ser
                245                 250                 255

Val Gln Met Lys Gly Ile Asn Gln Tyr Ile Ile Phe Tyr Lys Pro Lys
            260                 265                 270

Pro Thr Ser Phe Ala Arg Phe Arg Arg Ser Ala Arg Ser Arg Arg Ser
        275                 280                 285

Leu Pro Ala Glu Met Pro Leu Ile Pro Val Asn Gln Ala Asp Thr Leu
    290                 295                 300

Ile Val Asp Gly Glu Ala Val Ser Leu Thr Gly His Ser Gly Asn Ile
305                 310                 315                 320

Phe Ala Pro Glu Gly Asn Tyr Arg Tyr Leu Thr Tyr Gly Ala Glu Lys
                325                 330                 335

Leu Pro Gly Gly Ser Tyr Ala Leu Arg Val Gln Gly Glu Pro Ser Lys
            340                 345                 350

Gly Glu Met Leu Ala Gly Thr Ala Val Tyr Asn Gly Val Leu His
        355                 360                 365

Phe His Thr Glu Asn Gly Arg Pro Ser Pro Ser Arg Gly Arg Phe Ala
    370                 375                 380

Ala Lys Val Asp Phe Gly Ser Lys Ser Val Asp Gly Ile Ile Asp Ser
385                 390                 395                 400

Gly Asp Gly Leu His Met Gly Thr Gln Lys Phe Lys Ala Ala Ile Asp
                405                 410                 415

Gly Asn Gly Phe Lys Gly Thr Trp Thr Glu Asn Gly Gly Asp Val
            420                 425                 430

Ser Gly Lys Phe Tyr Gly Pro Ala Gly Glu Glu Val Ala Gly Lys Tyr
        435                 440                 445

Ser Tyr Arg Pro Thr Asp Ala Glu Lys Gly Phe Gly Val Phe Ala
    450                 455                 460

Gly Lys Lys Glu Gln Asp Gly Ser Gly Gly Gly Ala Thr Tyr Lys
```

```
              465                 470                 475                 480

Val Asp Glu Tyr His Ala Asn Ala Arg Phe Ala Ile Asp His Phe Asn
                    485                 490                 495

Thr Ser Thr Asn Val Gly Gly Phe Tyr Gly Leu Thr Gly Ser Val Glu
                500                 505                 510

Phe Asp Gln Ala Lys Arg Asp Gly Lys Ile Asp Ile Thr Ile Pro Val
                515                 520                 525

Ala Asn Leu Gln Ser Gly Ser Gln His Phe Thr Asp His Leu Lys Ser
530                 535                 540

Ala Asp Ile Phe Asp Ala Ala Gln Tyr Pro Asp Ile Arg Phe Val Ser
545                 550                 555                 560

Thr Lys Phe Asn Phe Asn Gly Lys Lys Leu Val Ser Val Asp Gly Asn
                565                 570                 575

Leu Thr Met His Gly Lys Thr Ala Pro Val Lys Leu Lys Ala Glu Lys
                580                 585                 590

Phe Asn Cys Tyr Gln Ser Pro Met Ala Lys Thr Glu Val Cys Gly Gly
                595                 600                 605

Asp Phe Ser Thr Thr Ile Asp Arg Thr Lys Trp Gly Val Asp Tyr Leu
                610                 615                 620

Val Asn Val Gly Met Thr Lys Ser Val Arg Ile Asp Ile Gln Ile Glu
625                 630                 635                 640

Ala Ala Lys Gln

<210> SEQ ID NO 3
<211> LENGTH: 434
<212> TYPE: PRT
<213> ORGANISM: Artificial Sequence
<220> FEATURE:
<223> OTHER INFORMATION: Immunogen for Neisseria meningitidis - fusion
      protein

<400> SEQUENCE: 3

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
                20                  25                  30

Leu Arg Ile Glu Thr Thr Ala Arg Ser Tyr Leu Arg Gln Asn Asn Gln
            35                  40                  45

Thr Lys Gly Tyr Thr Pro Gln Ile Ser Val Val Gly Tyr Asp Arg His
        50                  55                  60

Leu Leu Leu Leu Gly Gln Val Ala Thr Glu Gly Glu Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
                100                 105                 110

Thr Trp Asn Thr Ser Lys Val Arg Ala Thr Leu Leu Gly Ile Ser Pro
                115                 120                 125

Ala Thr Arg Ala Arg Val Lys Ile Val Thr Tyr Gly Asn Val Thr Tyr
130                 135                 140

Val Met Gly Ile Leu Thr Pro Glu Glu Gln Ala Gln Ile Thr Gln Lys
145                 150                 155                 160

Val Ser Thr Thr Val Gly Val Gln Lys Val Ile Thr Leu Tyr Gln Asn
                165                 170                 175

Tyr Val Gln Arg Gly Ser Gly Gly Gly Gly Val Ala Ala Asp Ile Gly
```

```
            180                 185                 190
Ala Gly Leu Ala Asp Ala Leu Thr Ala Pro Leu Asp His Lys Asp Lys
            195                 200                 205

Gly Leu Gln Ser Leu Thr Leu Asp Gln Ser Val Arg Lys Asn Glu Lys
            210                 215                 220

Leu Lys Leu Ala Ala Gln Gly Ala Glu Lys Thr Tyr Gly Asn Gly Asp
225                 230                 235                 240

Ser Leu Asn Thr Gly Lys Leu Lys Asn Asp Lys Val Ser Arg Phe Asp
            245                 250                 255

Phe Ile Arg Gln Ile Glu Val Asp Gly Gln Leu Ile Thr Leu Glu Ser
            260                 265                 270

Gly Glu Phe Gln Val Tyr Lys Gln Ser His Ser Ala Leu Thr Ala Phe
            275                 280                 285

Gln Thr Glu Gln Ile Gln Asp Ser Glu His Ser Gly Lys Met Val Ala
            290                 295                 300

Lys Arg Gln Phe Arg Ile Gly Asp Ile Ala Gly Glu His Thr Ser Phe
305                 310                 315                 320

Asp Lys Leu Pro Glu Gly Gly Arg Ala Thr Tyr Arg Gly Thr Ala Phe
            325                 330                 335

Gly Ser Asp Asp Ala Gly Gly Lys Leu Thr Tyr Thr Ile Asp Phe Ala
            340                 345                 350

Ala Lys Gln Gly Asn Gly Lys Ile Glu His Leu Lys Ser Pro Glu Leu
            355                 360                 365

Asn Val Asp Leu Ala Ala Ala Asp Ile Lys Pro Asp Gly Lys Arg His
            370                 375                 380

Ala Val Ile Ser Gly Ser Val Leu Tyr Asn Gln Ala Glu Lys Gly Ser
385                 390                 395                 400

Tyr Ser Leu Gly Ile Phe Gly Gly Lys Ala Gln Glu Val Ala Gly Ser
            405                 410                 415

Ala Glu Val Lys Thr Val Asn Gly Ile Arg His Ile Gly Leu Ala Ala
            420                 425                 430

Lys Gln

<210> SEQ ID NO 4
<211> LENGTH: 686
<212> TYPE: PRT
<213> ORGANISM: Artificial Sequence
<220> FEATURE:
<223> OTHER INFORMATION: Immunogen for Neisseria meningitidis - fusion
      protein

<400> SEQUENCE: 4

Met Val Ser Ala Val Ile Gly Ser Ala Ala Val Gly Ala Lys Ser Ala
1               5                   10                  15

Val Asp Arg Arg Thr Thr Gly Ala Gln Thr Asp Asp Asn Val Met Ala
            20                  25                  30

Leu Arg Ile Glu Thr Thr Ala Arg Ser Tyr Leu Arg Gln Asn Asn Gln
        35                  40                  45

Thr Lys Gly Tyr Thr Pro Gln Ile Ser Val Val Gly Tyr Asp Arg His
    50                  55                  60

Leu Leu Leu Leu Gly Gln Val Ala Thr Glu Gly Lys Gln Phe Val
65                  70                  75                  80

Gly Gln Ile Ala Arg Ser Glu Gln Ala Ala Glu Gly Val Tyr Asn Tyr
                85                  90                  95

Ile Thr Val Ala Ser Leu Pro Arg Thr Ala Gly Asp Ile Ala Gly Asp
```

-continued

```
                100                 105                 110
Thr Trp Asn Thr Ser Lys Val Arg Ala Thr Leu Leu Gly Ile Ser Pro
            115                 120                 125
Ala Thr Arg Ala Arg Val Lys Ile Val Thr Tyr Gly Asn Val Thr Tyr
        130                 135                 140
Val Met Gly Ile Leu Thr Pro Glu Glu Gln Ala Gln Ile Thr Gln Lys
145                 150                 155                 160
Val Ser Thr Thr Val Gly Val Gln Lys Val Ile Thr Leu Tyr Gln Asn
                165                 170                 175
Tyr Val Gln Arg Gly Ser Gly Gly Gly Val Ala Ala Asp Ile Gly
            180                 185                 190
Ala Gly Leu Ala Asp Ala Leu Thr Ala Pro Leu Asp His Lys Asp Lys
        195                 200                 205
Gly Leu Gln Ser Leu Thr Leu Asp Gln Ser Val Arg Lys Asn Glu Lys
    210                 215                 220
Leu Lys Leu Ala Ala Gln Gly Ala Glu Lys Thr Tyr Gly Asn Gly Asp
225                 230                 235                 240
Ser Leu Asn Thr Gly Lys Leu Lys Asn Asp Lys Val Ser Arg Phe Asp
                245                 250                 255
Phe Ile Arg Gln Ile Glu Val Asp Gly Gln Leu Ile Thr Leu Glu Ser
            260                 265                 270
Gly Glu Phe Gln Val Tyr Lys Gln Ser His Ser Ala Leu Thr Ala Phe
        275                 280                 285
Gln Thr Glu Gln Ile Gln Asp Ser Glu His Ser Gly Lys Met Val Ala
    290                 295                 300
Lys Arg Gln Phe Arg Ile Gly Asp Leu Gly Gly Glu His Thr Ala Phe
305                 310                 315                 320
Asn Gln Leu Pro Asp Gly Lys Ala Glu Tyr Arg Gly Thr Ala Phe Gly
                325                 330                 335
Ser Asp Asp Ala Gly Gly Lys Leu Thr Tyr Thr Ile Asp Phe Thr Lys
            340                 345                 350
Lys Gln Gly Asn Gly Lys Ile Glu His Leu Lys Ser Pro Glu Leu Asn
        355                 360                 365
Val Glu Leu Ala Ser Ala Glu Ile Lys Ala Asp Gly Lys Ser His Ala
    370                 375                 380
Val Ile Leu Gly Asp Val Arg Tyr Gly Ser Glu Glu Lys Gly Ser Tyr
385                 390                 395                 400
Ser Leu Gly Ile Phe Gly Gly Arg Ala Gln Glu Val Ala Gly Ser Ala
                405                 410                 415
Glu Val Lys Thr Val Asn Gly Ile Arg His Ile Gly Leu Ala Ala Lys
            420                 425                 430
Gln Gly Ser Gly Gly Gly Val Ala Ala Asp Ile Gly Ala Gly Leu
        435                 440                 445
Ala Asp Ala Leu Thr Ala Pro Leu Asp His Lys Asp Lys Gly Leu Gln
    450                 455                 460
Ser Leu Thr Leu Asp Gln Ser Val Arg Lys Asn Glu Lys Leu Lys Leu
465                 470                 475                 480
Ala Ala Gln Gly Ala Glu Lys Thr Tyr Gly Asn Gly Asp Ser Leu Asn
                485                 490                 495
Thr Gly Lys Leu Lys Asn Asp Lys Val Ser Arg Phe Asp Phe Ile Arg
            500                 505                 510
Gln Ile Glu Val Asp Gly Gln Leu Ile Thr Leu Glu Ser Gly Glu Phe
        515                 520                 525
```

-continued

```
Gln Val Tyr Lys Gln Ser His Ser Ala Leu Thr Ala Phe Gln Thr Glu
    530                 535                 540

Gln Ile Gln Asp Ser Glu His Ser Gly Lys Met Val Ala Lys Arg Gln
545                 550                 555                 560

Phe Arg Ile Gly Asp Leu Gly Gly Glu His Thr Ala Phe Asn Gln Leu
                565                 570                 575

Pro Asp Gly Lys Ala Glu Tyr Arg Gly Thr Ala Phe Gly Ser Asp Asp
            580                 585                 590

Ala Gly Gly Lys Leu Thr Tyr Thr Ile Asp Phe Thr Lys Lys Gln Gly
        595                 600                 605

Asn Gly Lys Ile Glu His Leu Lys Ser Pro Glu Leu Asn Val Glu Leu
    610                 615                 620

Ala Ser Ala Glu Ile Lys Ala Asp Gly Lys Ser His Ala Val Ile Leu
625                 630                 635                 640

Gly Asp Val Arg Tyr Gly Ser Glu Glu Lys Gly Ser Tyr Ser Leu Gly
                645                 650                 655

Ile Phe Gly Gly Arg Ala Gln Glu Val Ala Gly Ser Ala Glu Val Lys
            660                 665                 670

Thr Val Asn Gly Ile Arg His Ile Gly Leu Ala Ala Lys Gln
        675                 680                 685

<210> SEQ ID NO 5
<211> LENGTH: 776
<212> TYPE: PRT
<213> ORGANISM: Artificial Sequence
<220> FEATURE:
<223> OTHER INFORMATION: Immunogen for Neisseria meningitidis - fusion
      protein

<400> SEQUENCE: 5

Met Gly Pro Asp Ser Asp Arg Leu Gln Gln Arg Arg Val Ala Ala Asp
1               5                   10                  15

Ile Gly Ala Gly Leu Ala Asp Ala Leu Thr Ala Pro Leu Asp His Lys
            20                  25                  30

Asp Lys Ser Leu Gln Ser Leu Thr Leu Asp Gln Ser Val Arg Lys Asn
        35                  40                  45

Glu Lys Leu Lys Leu Ala Ala Gln Gly Ala Glu Lys Thr Tyr Gly Asn
    50                  55                  60

Gly Asp Ser Leu Asn Thr Gly Lys Leu Lys Asn Asp Lys Val Ser Arg
65                  70                  75                  80

Phe Asp Phe Ile Arg Gln Ile Glu Val Asp Gly Gln Leu Ile Thr Leu
                85                  90                  95

Glu Ser Gly Glu Phe Gln Ile Tyr Lys Gln Asp His Ser Ala Val Val
            100                 105                 110

Ala Leu Gln Ile Glu Lys Ile Asn Asn Pro Asp Lys Ile Asp Ser Leu
        115                 120                 125

Ile Asn Gln Arg Ser Phe Leu Val Ser Gly Leu Gly Gly Glu His Thr
    130                 135                 140

Ala Phe Asn Gln Leu Pro Asp Gly Lys Ala Glu Tyr His Gly Lys Ala
145                 150                 155                 160

Phe Ser Ser Asp Asp Ala Gly Gly Lys Leu Thr Tyr Thr Ile Asp Phe
                165                 170                 175

Ala Ala Lys Gln Gly His Gly Lys Ile Glu His Leu Lys Thr Pro Glu
            180                 185                 190

Gln Asn Val Glu Leu Ala Ala Ala Glu Leu Lys Ala Asp Glu Lys Ser
```

-continued

```
            195                 200                 205
His Ala Ile Leu Gly Asp Thr Arg Tyr Gly Ser Glu Glu Lys Gly
210                 215                 220

Thr Tyr His Leu Ala Leu Phe Gly Asp Arg Ala Gln Glu Ile Ala Gly
225                 230                 235                 240

Ser Ala Thr Val Lys Ile Gly Glu Lys Val His Glu Ile Gly Ile Ala
                245                 250                 255

Gly Lys Gln Gly Ser Gly Gly Gly Val Ala Ala Asp Ile Gly Ala
                260                 265                 270

Gly Leu Ala Asp Ala Leu Thr Ala Pro Leu Asp His Lys Asp Lys Gly
                275                 280                 285

Leu Gln Ser Leu Thr Leu Asp Gln Ser Val Arg Lys Asn Glu Lys Leu
                290                 295                 300

Lys Leu Ala Ala Gln Gly Ala Glu Lys Thr Tyr Gly Asn Gly Asp Ser
305                 310                 315                 320

Leu Asn Thr Gly Lys Leu Lys Asn Asp Lys Val Ser Arg Phe Asp Phe
                325                 330                 335

Ile Arg Gln Ile Glu Val Asp Gly Gln Leu Ile Thr Leu Glu Ser Gly
                340                 345                 350

Glu Phe Gln Val Tyr Lys Gln Ser His Ser Ala Leu Thr Ala Phe Gln
                355                 360                 365

Thr Glu Gln Ile Gln Asp Ser Glu His Ser Gly Lys Met Val Ala Lys
                370                 375                 380

Arg Gln Phe Arg Ile Gly Asp Ile Ala Gly Glu His Thr Ser Phe Asp
385                 390                 395                 400

Lys Leu Pro Glu Gly Gly Arg Ala Thr Tyr Arg Gly Thr Ala Phe Gly
                405                 410                 415

Ser Asp Asp Ala Gly Gly Lys Leu Thr Tyr Thr Ile Asp Phe Ala Ala
                420                 425                 430

Lys Gln Gly Asn Gly Lys Ile Glu His Leu Lys Ser Pro Glu Leu Asn
                435                 440                 445

Val Asp Leu Ala Ala Ala Asp Ile Lys Pro Asp Gly Lys Arg His Ala
                450                 455                 460

Val Ile Ser Gly Ser Val Leu Tyr Asn Gln Ala Glu Lys Gly Ser Tyr
465                 470                 475                 480

Ser Leu Gly Ile Phe Gly Gly Lys Ala Gln Glu Val Ala Gly Ser Ala
                485                 490                 495

Glu Val Lys Thr Val Asn Gly Ile Arg His Ile Gly Leu Ala Ala Lys
                500                 505                 510

Gln Gly Ser Gly Pro Asp Ser Asp Arg Leu Gln Gln Arg Arg Val Ala
                515                 520                 525

Ala Asp Ile Gly Thr Gly Leu Ala Asp Ala Leu Thr Ala Pro Leu Asp
                530                 535                 540

His Lys Asp Lys Gly Leu Lys Ser Leu Thr Leu Glu Asp Ser Ile Pro
545                 550                 555                 560

Gln Asn Gly Thr Leu Thr Leu Ser Ala Gln Gly Ala Glu Lys Thr Phe
                565                 570                 575

Lys Ala Gly Asp Lys Asp Asn Ser Leu Asn Thr Gly Lys Leu Lys Asn
                580                 585                 590

Asp Lys Ile Ser Arg Phe Asp Phe Val Gln Lys Ile Glu Val Asp Gly
                595                 600                 605

Gln Thr Ile Thr Leu Ala Ser Gly Glu Phe Gln Ile Tyr Lys Gln Asn
610                 615                 620
```

-continued

```
His Ser Ala Val Val Ala Leu Gln Ile Glu Lys Ile Asn Asn Pro Asp
625                 630                 635                 640

Lys Thr Asp Ser Leu Ile Asn Gln Arg Ser Phe Leu Val Ser Gly Leu
            645                 650                 655

Gly Gly Glu His Thr Ala Phe Asn Gln Leu Pro Gly Gly Lys Ala Glu
            660                 665                 670

Tyr His Gly Lys Ala Phe Ser Ser Asp Asp Pro Asn Gly Arg Leu His
        675                 680                 685

Tyr Ser Ile Asp Phe Thr Lys Lys Gln Gly Tyr Gly Arg Ile Glu His
        690                 695                 700

Leu Lys Thr Leu Glu Gln Asn Val Glu Leu Ala Ala Ala Glu Leu Lys
705                 710                 715                 720

Ala Asp Glu Lys Ser His Ala Val Ile Leu Gly Asp Thr Arg Tyr Gly
            725                 730                 735

Ser Glu Glu Lys Gly Thr Tyr His Leu Ala Leu Phe Gly Asp Arg Ala
            740                 745                 750

Gln Glu Ile Ala Gly Ser Ala Thr Val Lys Ile Gly Glu Lys Val His
        755                 760                 765

Glu Ile Gly Ile Ala Gly Lys Gln
        770                 775
```

FLOW CYTOMETRY ANALYSIS OF MATERIALS ADSORBED TO METAL SALTS

This application is the U.S. National Phase of International Application No. PCT/US2011/064938, filed Dec. 14, 2011 and published in English, which claims the benefit of U.S. Provisional Application No. 61/423,001 (filed Dec. 14, 2010), the complete contents of which are hereby incorporated herein by reference for all purposes.

TECHNICAL FIELD

The invention is in the field of analysing adsorbed material e.g. in vaccines.

SEQUENCE LISTING

The instant application contains a Sequence Listing which has been submitted via EFS-Web and is hereby incorporated by reference in its entirety. The ASCII copy, created on Jun. 14, 2013, is named PAT54336_ASCII.TXT, and is 25,126 bytes in size.

BACKGROUND ART

Vaccine antigens are frequently adsorbed to insoluble metal salts, such as aluminium hydroxide and aluminium phosphate, to provide an adjuvant effect. It is often necessary to analyse antigens after their adsorption, but the adsorption itself can make analysis difficult e.g. as described in reference 1 for hepatitis B surface antigen (HBsAg).

Rather than testing adsorbed antigens directly, many assays instead rely on a desorption treatment, followed by analysis of the released antigen. For example, to measure the proportion of adsorbed antigen it is known to test for unadsorbed antigen before and after a desorption treatment, with the difference being used to infer the amount of adsorption. In this type of assay, however, the requirement for a desorption step is cumbersome, and it also means that the antigen is not being analysed in the form in which it is actually supplied or used.

Direct in situ quantification of adsorbed antigens has been reported e.g. by ELISA in reference 2, or by near-infrared spectroscopy in reference 3. Reference 4 discloses a direct alhydrogel formulation immunoassay ("DAFIA") which is designed to directly (i.e. without prior extraction), accurately, sensitively, and specifically determine the content, identity and integrity of an antigen while it remains adsorbed to an aluminium hydroxide adjuvant.

It is an object of the invention to provide further and improved methods for analysing vaccine antigens (or other components) which are adsorbed to insoluble metal salts.

DISCLOSURE OF THE INVENTION

The invention utilises the techniques and instruments which are typically used in flow cytometry (FC) as a tool for analysing adsorbed materials. The invention provides in general a convenient way of analysing adsorbed components, which permits the analysis of individual particles of insoluble metal salts with components adsorbed to them to determine their properties, and from there to determine the average properties of a suspension of these particles.

A suspension of insoluble metal salt particles with adsorbed component(s) is passed through a flow cytometer to determine the properties of the individual particles. In a flow cytometer, each particle is passed through one or more beams of light, typically laser beams of set wavelength. A number of detectors are placed around the beam(s) of light. One detector is in line with the light beam in order to detect the forward scatter, and one or more may be perpendicular to the light beam, which detect the side scatter of the particle. Additionally, one or more detectors are situated near the light beam in order to detect light emitted from luminescent labels (e.g. fluorescent labels), which can be excited by the light beam. Typically, the wavelength of the light emitted from the luminescent label must differ from the wavelength of the light beam shone onto the particle, to ensure specific detection of the label. The degree of light scattering from the particle permits the size and morphology of the particle to be determined. The luminescence detector permits the detection of specific components adsorbed to the particle via the emission of a certain wavelength of light from a label attached to the adsorbed component. By using multiple labels, each of which emits a different wavelength of light, and each of which is specific for a single component, multiple adsorbed components in a single suspension of insoluble metal salt particles can be simultaneously analysed.

Thus the invention provides flow cytometry for the analysis of components adsorbed to an insoluble metal salt. In order to permit detection by the flow cytometer, the component must be labelled. In some embodiments, the adsorbed component contains an intrinsic label. In other embodiments, a detectable label is added by a binding reagent. Thus the invention provides a method for analysing a component which is adsorbed to an insoluble metal salt, comprising steps of: (i) labelling the adsorbed component with a binding reagent to produce a labelled adsorbed component; and (ii) analysing the labelled adsorbed component by flow cytometry.

This method is advantageous over many of the methods in the prior art because it is not necessary to desorb the component which is adsorbed to the insoluble metal salt. Instead, the adsorbed component can be analysed while it is still attached to the insoluble metal salt. In addition to the removal of the need for desorption, analysis in situ may in some circumstances also permit the determination of the activity of the adsorbed component.

The invention also provides a flow cytometer comprising a labelled component adsorbed to an insoluble metal salt. The invention also provides a cytometer sample tube comprising a labelled component adsorbed to an insoluble metal salt.

In practice, typically a large batch of insoluble metal salt adsorbed component is made. A sample of this batch is then analysed by the method of the invention.

The method of the invention can be illustrated using an example of a protein as the adsorbed component, and first and second antibodies as the binding reagent. As set out above, a blocking step which comprises incubating the adsorbed component in BSA may be performed. This ensures that any unoccupied binding sites on the insoluble metal salt are occupied, so preventing the adsorption of any binding reagents to the insoluble metal salt. Next, the adsorbed component is incubated with a first reagent, in this example an antibody, which binds to the adsorbed protein and not to any other components used in the assay. This step is followed by the addition of a second reagent, which comprises a label capable of being detected by the flow cytometer, and which binds specifically to the first reagent, for example a fluorescently labelled antibody binding to the first antibody (e.g. by binding to the Fc region of the first antibody, so that if the first antibody is a goat antibody, the second antibody should be an anti-goat antibody from another species). Wash steps are incorporated as necessary between the binding steps.

The method of analysing an adsorbed component by flow cytometry may comprise one or more additional steps prior to passing the adsorbed component through the flow cytometer. Thus the invention provides a method of analysing an adsorbed component comprising one or more of the steps of:

synthesising insoluble metal salt particles;
suspending the insoluble metal salt particles in a liquid;
synthesising one or more components for adsorption;
combining insoluble metal salt particles with one or more components for adsorption;
incubating a combination of insoluble metal salt particles with one or more components for adsorption under conditions which permit adsorption of the component onto the insoluble metal salt particles;
combining the suspension of adsorbed component on an insoluble metal salt with one or more further components, for example components adsorbed on an insoluble metal salt which optionally may have already been analysed by the flow cytometry method of the invention;
dilution or concentration of the one or more components adsorbed to the insoluble metal salt;
filtering the suspension of adsorbed component on an insoluble metal salt;
exchanging the solvent in which the particles are suspended, which may be the exchange from a non-aqueous solvent to an aqueous solvent (and vice versa) or the exchange of the buffer component of an aqueous solvent;
taking a sample of the batch of adsorbed component;
adding a preservative to the suspension of the adsorbed component on an insoluble metal salt;
adding a physiological salt to the suspension of adsorbed component on an insoluble metal salt;
altering the pH of the suspension of adsorbed component on an insoluble metal salt;
altering the osmolality of the suspension of adsorbed component on an insoluble metal salt;
sterilising the suspension of adsorbed component on an insoluble metal salt;
removing endotoxin from a suspension of adsorbed component on an insoluble metal salt;
adding a blocking reagent; and/or
adding one of more binding reagents;

and the step of analysing the adsorbed component by flow cytometry.

The order of steps listed above is not a strict indication of the order in which they are to be performed in the method, but provides one example in which they can be combined. It is well within the capabilities of the skilled person, following the teachings herein, to generate further methods of analysis by the rearrangement and/or repetition of one or more steps. Many of the steps (e.g. sampling, adjusting the pH, diluting or concentrating etc.) may be performed more than once at different stages.

The measurement by flow cytometry, however, provides data only on the degree of adsorption of the component to the insoluble metal salt at the time of assay. In practice, pharmaceutical compositions may be kept for months, and often years, before use. It is well known that adsorbed components can become desorbed from insoluble metal salts over time, and this desorption depends on the particular insoluble metal salt, adsorbed component and buffer, inter alia. The method of the present invention can therefore be used repeatedly over time to assay further samples from the same batch of component adsorbed to an insoluble metal salt to determine the stability of the adsorption interaction. A range of variables (buffer composition, temperature, osmolality etc.) can be tested to determine the optimum conditions for storage of a composition and the degree of adsorption easily and quickly determined using the method of the invention. Thus the invention provides a method of determining the stability of an adsorbed component comprising determining the degree of adsorption of a component to a metal salt by flow cytometry and repeating the flow cytometry analysis one or more times.

As noted above, the results from the analysis of the component adsorbed to the insoluble metal salt can determine if a number of downstream steps are undertaken. The properties of the analysed adsorbed component are typically compared to predetermined parameters. These parameters can be wide ranging. For instance, for a particular composition, particular sizes of insoluble metal salt particle may be preferred, particular ratios of insoluble metal salt to adsorbed component may be preferred or particular ratios of adsorbed components if the assayed composition comprises more than one, or stability for a particular period of time under specific conditions is required. The particular parameters which must be met are, of course, dependent upon the insoluble metal salt, adsorbed component, buffer, and the ultimate use of the adsorbed component.

The method of the invention has many applications. For instance, it can form a quality control step in a manufacturing and distributing process. Thus the invention provides a method of manufacturing a composition comprising the step of analysing a labelled adsorbed component by flow cytometry and one or more of the steps of:

calculating one or more parameters from the data acquired in the flow cytometry analysis, for example particle size distribution, % adsorption of the component to the insoluble metal salt and/or distribution of the antigen on the metal particles;
deciding to proceed with manufacturing a composition incorporating the assayed batch of adsorbed component on the basis of the results of the flow cytometry analysis;
combining the suspension of adsorbed component on an insoluble metal salt with one or more further components, for example components adsorbed on an insoluble metal salt which may have also been analysed by the flow cytometry method of the invention;
filtering the suspension of adsorbed component on an insoluble metal salt;
exchanging the solvent in which the particles are suspended, which may be the exchange from a non-aqueous solvent to an aqueous solvent (and vice versa) or the exchange of the buffer component of an aqueous solvent;
adding a preservative to the suspension of the adsorbed component on an insoluble metal salt;
adding a physiological salt to the suspension of adsorbed component on an insoluble metal salt;
altering the pH of the suspension of adsorbed component on an insoluble metal salt;
altering the osmolality of the suspension of adsorbed component on an insoluble metal salt;
sterilising the suspension of adsorbed component on an insoluble metal salt;
removing endotoxin from a suspension of adsorbed component on an insoluble metal salt;

lyophilising a suspension of adsorbed component on an insoluble metal salt;

resuspending a lyophilisate of adsorbed component on an insoluble metal salt;

dividing the suspension of adsorbed component on an insoluble metal salt into smaller volumes;

preparing a unit dose of the suspension of adsorbed component on an insoluble metal salt;

formatting a unit dose of the suspension of adsorbed component on an insoluble metal salt as an injectable; and/or packaging a unit dose of the suspension of adsorbed component on an insoluble metal salt, optionally with instructions for use.

The order of steps listed above is not an indication of the order in which they are to be performed in the method of manufacture. Indeed, many of the steps (e.g. sampling, adjusting the pH, dilution or concentrating etc.) may be performed more than once at different stages in the manufacturing method. The step of analysing the adsorbed component can be performed at nearly any stage in the method, and provides important information at each point. Indeed, it can be performed multiple times. For instance, a change in the buffer or the pH of the suspension to one suitable for a composition for use as a pharmaceutical may interfere with the adsorption interaction, or may cause the particles of insoluble metal salt to aggregate to a greater or lesser degree. By analysing a sample of the suspension comprising the adsorbed component prior to and following a step in the method, the precise effect of that step can be simply and quickly determined. Following its manufacture (which includes the step of analysis by flow cytometry), the adsorbed component, optionally in the form of a composition, can be distributed. Thus the invention provides a method of distributing an adsorbed component, or composition comprising the adsorbed component, comprising a method of flow cytometry or a method of manufacture as set out above and the step of distributing the adsorbed component or composition comprising the adsorbed component.

The Sample

A sample of this batch will then be analysed by the method of the invention. The sample is typically less than 100 ml, for example less than 50 ml, less than 40 ml, less than 30 ml, less than 20 ml, less than 10 ml, less than 5 ml, less than 4 ml, less than 3 ml, less than 2 ml, less than 1 ml, or less than 0.5 ml. The sample is typically at least 100 µl, for example at least 200 µl, at least 300 µl, at least 400 µl, at least 500 µl, at least 600 µl, at least 700 µl, at least 800 µl, at least 900 µl, at least 1 ml, at least 2 ml, at least 3 ml, at least 4 ml, or at least 5 ml. The batch of insoluble metal salt adsorbed component may be of a different concentration to the concentration of insoluble metal salt and/or adsorbed component that is suitable for analysis by the flow cytometry method of the invention. Therefore it may be necessary to dilute or concentrate the suspension as necessary to achieve the desired concentration of insoluble metal salt and/or adsorbed component. Typically flow cytometry analysis is performed on suspensions with a particle concentration of about $10^3$-$10^9$ particles $ml^{-1}$, for example $10^4$-$10^8$ particles $ml^{-1}$, $10^5$-$10^7$ particles $ml^{-1}$ such as about $10^6$ particles $ml^{-1}$. The concentration of insoluble metal salt may range from about 10 µg $ml^{-1}$-about 100 mg $ml^{-1}$, for example about 100 µg $ml^{-1}$-about 10 mg $ml^{-1}$, about 500 µg $ml^{-1}$-about 5 mg $ml^{-1}$, such as about 1000 to about 2000 µg $ml^{-1}$. Similarly the concentration of adsorbed component may vary, but will typically be about 1 µg $ml^{-1}$-about 10 mg $ml^{-1}$, for example about 10 µg $ml^{-1}$-about 1 mg $ml^{-1}$, about 25 µg $ml^{-1}$-about 500 µg $ml^{-1}$, such as about 50 µg $ml^{-1}$ to about 150 µg $ml^{-1}$ Determination of Adsorption The adsorbed component is detected through a specific label. This label may be part of the adsorbed component, for example a portion of a small molecule which contains a region of conjugated bonds, as detailed further below. In an alternative, the label may be attached to the adsorbed component through a binding reagent. Binding reagents and labels for use in the method of the invention are discussed in more detail below.

When the component is adsorbed to the insoluble metal salt, the insoluble metal salt particle can then be detected through the adsorbed component, either by the intrinsic label or by the one or more binding reagents used to attach a label. Thus an insoluble metal salt particle which has one or more components adsorbed to it can be distinguished from an insoluble metal salt particle which has no components attached to it. Thus the present method permits the determination of the antigen distribution on the insoluble metal salt suspension.

The determination of the distribution of adsorption is important to ensure that the optimum ratio of component and adjuvant has been reached, for example to ensure complete adsorption with minimum loss of excess antigen, or to ensure the maximal in vivo response.

Analysis of Suspensions Containing Multiple Adsorbed Components

The method of the invention can be used to specifically analyse a single antigen in a suspension of multiple adsorbed components. The method may also be used to simultaneously analyse multiple species of adsorbed component in a suspension. The suspension may contain insoluble metal salt particles with multiple different adsorbed components. This suspension may be generated by the addition of a solution containing the different species of component for adsorption to the insoluble metal salt suspension. In an alternative, the suspension of multiple absorbed components may comprise insoluble metal salt particles each of which has only one species of component adsorbed to it. This suspension may be generated by adsorbing each component to the insoluble metal salt in isolation before combining them.

In essence, the method for analysing multiple adsorbed components comprises the performance of the method of the invention multiple times in parallel. Following the optional blocking step, if required, multiple binding reagents are added, simultaneously or serially, each binding reagent being specific in its binding for a different adsorbed component. The result of the addition of the binding reagents is the linking of a different detectable label to each different adsorbed component, thus permitting the detection of each adsorbed component in isolation from the remaining components of the suspension. In an alternative, one binding reagent may bind to all adsorbed components. This alternative would permit the detection of the total amount of adsorption by the different adsorbed component to the insoluble metal salt.

In one embodiment, the multiple species of adsorbed component are adsorbed to the same metal salt (e.g. aluminium hydroxide). In another embodiment, the species are adsorbed to different metal salts, for example in a suspension comprising two adsorbed components, the first component is adsorbed to aluminium hydroxide and the second component is adsorbed to aluminium phosphate.

Binding Reagents

The methods of the invention typically require the use of a binding reagent which is used to label the adsorbed component. The binding reagent may be a single reagent, or may comprise two or more reagents. If the binding reagent comprises more than one reagent, these reagents may be added simultaneously or sequentially. If a binding reagent is used, the first reagent is a compound which binds to the adsorbed component, usually specifically to that adsorbed component. If the adsorbed compound is a protein or a carbohydrate, the first reagent may be an antibody which binds to the component. If the adsorbed component is a receptor, the first reagent may be a ligand which binds to that receptor (or vice versa). If the adsorbed compound is a carbohydrate, the first reagent may be a lectin.

The binding of a reagent to the adsorbed component may in some instances be used indicate that the component is in a biologically active from. If a particular conformation of the component is known to be necessary for the biological activity of the component, then by using an antibody which binds only to an epitope present in the active form, the active form can be specifically labelled and thus detected. Similarly, if the component is a ligand, and it can be bound by its cognate receptor, then this may be indication that the adsorbed component is in a biologically active configuration.

The first reagent may be linked to a label which is detectable by the flow cytometer, in which instance the first reagent will typically be the only reagent. In an alternative, the first reagent may be linked to a label which is not detectable by the flow cytometer, i.e. a tag, for instance one partner of a typical affinity pairing (e.g. biotin and avidin), or a sequence tag such as a $His_6$, myc or FLAG tag. In a further alternative, the first reagent is not labelled. Typically, if the first reagent comprises a detectable label, then a second reagent is not required. If the first reagent is linked to a non-detectable label or is not labelled, then a second reagent is typically employed.

The second reagent usually comprises a label which is detectable by the flow cytometer. The second reagent is capable of binding to the first reagent. The second reagent is often an antibody with affinity for the first reagent. In the case where the first reagent is an antibody, the second reagent is typically an antibody which binds to the first antibody (i.e. if the first reagent was a goat antibody, the second reagent should be an anti-goat antibody). As detailed above, in some instances the first reagent comprises a label which is not detectable by the flow cytometer. In this situation, the second reagent can bind specifically to the label of the first reagent, for instance if the non-detectable label on the first reagent is a FLAG tag, the second reagent is ideally an anti-FLAG antibody.

If the binding reagent is an antibody it may be a polyclonal antibody or a monoclonal antibody. It is preferred to use a monoclonal antibody where binding to a specific epitope is desired, for instance in the situation where specifically an active form of adsorbed component is being labelled. Antibodies of the invention can be of any isotype (e.g. IgA, IgG, IgM i.e. an $\alpha$, $\gamma$ or $\mu$ heavy chain) and may have a $\kappa$ or a $\lambda$ light chain. The antibody may be derived from a variety sources, for example human, cow, rat, mouse, pig, goat, rabbit, camel, sheep, guinea pig, snake, frog, llama, carp, shark, dog, cat, duck ostrich or chicken.

Although typically a binding reagent comprising more than one reagent will be composed of two reagents, there is no upper limit to the number of reagents. All that is required is that each reagent of the binding reagent should bind to the preceding reagent, and ultimately introduce a label which is specifically bound to the adsorbed component. Thus the binding reagent may comprise one, two, three, four, five, six, seven, eight, nine, ten or more than ten reagents.

Labels for Detection by the Flow Cytometer

If the adsorbed component is not intrinsically fluorescent (i.e. it does not autofluoresce) then, as detailed previously, it is necessary to use one or more binding reagents which comprise a label which can be detected by the flow cytometer. Typically this will be a luminescent label, for example a fluorescent label. A wide range of fluorescent labels exist which are compatible with the method of the invention. Selection of an appropriate label is dependent upon any intrinsic absorption and emission spectra of the insoluble metal salt, the adsorbed component(s), and any other reagents used in the assay. The intrinsic fluorescence of the components can be simply determined by passing the assay components through the flow cytometer without the detectable label, as described herein.

Labels should be selected with absorption and emission spectra which do not interfere, or do not interfere to a significant extent, with those of the assay components. The spectra do not interfere to a significant degree if the labelled adsorbed component can be specifically and sensitively detected when it passes through the flow cytometer.

A wide range of labels spanning the spectrum of visible light are available (see Table 1 for a non-limiting list of fluorescent labels). Further labels and a guide to fluorescent labelling may be found in reference 5. Selection of a suitable label or combination of labels is well within the capability of the skilled person following the teachings herein.

Detection without Binding Reagents

As noted previously, some adsorbed compounds may intrinsically fluoresce, a phenomenon also termed autofluorescence. When such a compound is adsorbed to an insoluble metal salt, the use of one or more binding reagents to label the adsorbed component is not required to permit the detection of the adsorbed complex by flow cytometry. Instead, flow cytometry analysis can be performed immediately following adsorption. Optionally one or more wash steps to remove unbound adsorbed component from the insoluble metal salt particles may be employed. Intrinsically fluorescent adsorbed components typically contain conjugated systems, i.e. a system of connected p-orbitals in a series of alternating single and double bonds, which allow delocalisation of pi electrons. The conjugated system may be aromatic, non-aromatic or anti-aromatic.

An exemplary class of autofluorescent molecules comprises a benzonaphthyridine scaffold, for example SMIPs which are analogs of Compound A. A number of analogs of Compound A are displayed in Table 2, including compounds B to H. Any of the general and specific compounds in references 6 can be analysed using the invention, as can other autofluorescent molecules (in particular SMIPs) which comprise a phosphonate group (or a phosphinate, a phosphonite, a phosphinite, or a phosphate group) and which can adsorb to insoluble metal salts.

The autofluorescent adsorbed component may be a protein. Fluorescence by a protein may be the result of intrinsic fluorescence of tryptophan residues in that protein, though a lesser contribution to fluorescence may be made by tyrosine and phenylalanine residues. The three residues have distinct absorption and emission maxima, which are typically as follows: tryptophan absorbs at 280 nm and fluoresces at 348 nm, tyrosine absorbs at 274 nm and fluoresces at 303 nm and phenylalanine absorbs at 257 nm and fluoresces at 282 nm. The exact absorption and fluorescence wavelengths of the residue depend on the local chemical environment of the residue. Tryptophan residues which are in hydrophobic regions of a proteins, for instance the core, can have spectra which are shifted by 10 to 20 nm compared to a tryptophan in the hydrophilic regions, e.g. the surface, of the protein.

If the component is a protein which is associated with a cofactor, then the fluorescence of that cofactor may be used as a label to detect the component. NADH and/or NADPH are cofactors for a number of proteins, and have approximate absorption and fluorescence maxima at 340 nm and 460 nm respectively. Riboflavin, FMN and FAD absorb at approximately 450 nm and fluoresce at approximately 525 nm. Other cofactors are based on a porphyrin ring. Proteins comprising a porphyrin ring include heme containing proteins and chlorophyll containing proteins.

Some components may comprise intrinsic fluorophores which are not cofactors. For example, green fluorescent protein (GFP) and its derivatives comprise an imidazolin-5-one heterocyclic ring fluorophore formed from the tripeptide Thr-Tyr-Gly present in the primary sequence of the protein.

In some embodiments, the invention encompasses methods in which there are multiple adsorbed components, at least one of which is autofluorescent and at least one of which is labeled using a binding reagent e.g. an embodiment in which both an antigen and a compound of Table 2 are adsorbed to a metal salt.

Blocking

In some suspensions that are analysed by the method of the invention, it is envisaged that some of the sites capable of binding components on the insoluble metal salt will not be occupied by the adsorbed component. In this instance, a further step to block the free sites prior to the addition of a binding reagent may be performed. By blocking is meant the addition of a further reagent which is capable of adsorption to the insoluble metal salt, but which differs from the adsorbed component and which is not recognised by a binding reagent. This ensures that the risk of the binding sites which remain on the insoluble metal salt following adsorption of the adsorbed component being occupied by the binding reagent is minimised or eliminated. Non-specific binding, i.e. adsorption, of the binding reagent to the insoluble metal salt should be avoided because it can lead to a reduction in the sensitivity and specificity of the method. A typical reagents used to block binding sites on the insoluble metal salt includes one or more of BSA, newborn calf serum, casein, casein digest, milk powder (e.g. skimmed milk powder), chick albumin, rabbit serum, horse serum, goat serum, mouse serum, human serum, rat serum, pig serum, Block Ace (Serotec), *E. coli* extract, pig skin gelatin, fish skin gelatin, steelhead salmon serum, Protein-Free Blocking Buffer (Pierce), salmon sperm DNA and randomly sheared genomic DNA. Thus the invention provides a method further comprising the step of blocking the insoluble metal salt, prior to the addition of the binding reagent.

Washing

Usually a wash step comprises centrifuging the insoluble metal salt particles to form a pellet, aspirating the supernatant and replacing it with a fresh buffer solution. The suspension is then passed through the flow cytometer which is able to detect the size of the particle (thus providing information on the number of insoluble metal salt particles in the desired size range and also excluding any aggregates of binding reagent from analysis) and also any luminescence from the label bound to the adsorbed component (which permits differentiation between insoluble metal salt particles which have component adsorbed to them, and those which do not, and also the degree of adsorption). Thus the proportion of the particles in the suspension which are of appropriate size and which also fluoresce appropriately (indicating the presence of the adsorbed component) can be determined. This information can then be used to determine whether or not the batch of material which has been assayed is suitable for use in downstream processes.

Insoluble Metal Salts

As disclosed herein, components can adsorb to insoluble metal salts, thereby forming an adsorbed complex. For instance, they can be adsorbed to insoluble calcium salts (e.g. calcium phosphate) or, preferably, to insoluble aluminium salts. Such aluminium salts have a long history of use in vaccines. Aluminium salts which include hydroxide ions are the preferred insoluble metal salts for use with the present invention.

Useful aluminium salts include, but are not limited to, aluminium hydroxide, aluminium oxyhydroxide, and aluminium hydroxyphosphates (including aluminium hydroxyphosphate sulfate). Such salts are described e.g. in chapters 8 & 9 of reference 7.

Preferred salts for adsorption of components are aluminium oxyhydroxides and/or aluminium hydroxyphosphate. These have surface hydroxyl moieties which can readily undergo ligand exchange with phosphorus-containing groups (e.g. phosphates, phosphonates) to provide stable adsorption.

The adjuvants commonly known as "aluminium hydroxide" are typically aluminium oxyhydroxide salts, which are usually at least partially crystalline. Aluminium oxyhydroxide, which can be represented by the formula AlO(OH), can be distinguished from other aluminium compounds, such as aluminium hydroxide Al(OH)$_3$, by infrared (IR) spectroscopy, in particular by the presence of an adsorption band at 1070 cm$^{-1}$ and a strong shoulder at 3090-3100 cm$^{-1}$ (chapter 9 of ref. 7). The degree of crystallinity of an aluminium hydroxide adjuvant is reflected by the width of the diffraction band at half height (WHH), with poorly-crystalline particles showing greater line broadening due to smaller crystallite sizes. The surface area increases as WHH increases, and adjuvants with higher WHH values have been seen to have greater capacity for antigen adsorption. A fibrous morphology (e.g. as seen in transmission electron micrographs) is typical for aluminium hydroxide adjuvants. The pI of aluminium hydroxide adjuvants is typically about 11 i.e. the adjuvant itself has a positive surface charge at physiological pH. Adsorptive capacities of between 1.8-2.6 mg protein per mg Al$^{+++}$ at pH 7.4 have been reported for aluminium hydroxide adjuvants.

The adjuvants commonly known as "aluminium phosphate" are typically aluminium hydroxyphosphates, often also containing a small amount of sulfate (i.e. aluminium hydroxyphosphate sulfate). They may be obtained by precipitation, and the reaction conditions and concentrations during precipitation influence the degree of substitution of phosphate for hydroxyl in the salt. Hydroxyphosphates generally have a PO$_4$/Al molar ratio between 0.3 and 1.2. Hydroxyphosphates can be distinguished from strict AlPO$_4$ by the presence of hydroxyl groups. For example, an IR spectrum band at 3164 cm$^{-1}$ (e.g. when heated to 200° C.) indicates the presence of structural hydroxyls (chapter 9 of reference 7).

The PO$_4$/Al$^{3+}$ molar ratio of an aluminium phosphate adjuvant will generally be between 0.3 and 1.2, preferably between 0.8 and 1.2, and more preferably 0.95±0.1. The aluminium phosphate will generally be amorphous, particularly for hydroxyphosphate salts. A typical adjuvant is amorphous aluminium hydroxyphosphate with PO$_4$/Al molar ratio between 0.84 and 0.92, included at 0.6 mg Al$^{3+}$/ml. The aluminium phosphate will generally be particulate (e.g. plate-like morphology as seen in transmission electron micrographs). Typical diameters of the particles are in the range 0.5-20 μm (e.g. about 5-10 μm) after any antigen adsorption. Adsorptive capacities of between 0.7-1.5 mg protein per mg Al$^{+++}$ at pH 7.4 have been reported for aluminium phosphate adjuvants.

The point of zero charge (PZC) of aluminium phosphate is inversely related to the degree of substitution of phosphate for hydroxyl, and this degree of substitution can vary depending on reaction conditions and concentration of reactants used for preparing the salt by precipitation. PZC is also altered by changing the concentration of free phosphate ions in solution (more phosphate=more acidic PZC) or by adding a buffer such as a histidine buffer (makes PZC more basic). Aluminium phosphates used according to the invention will generally have a PZC of between 4.0 and 7.0, more preferably between 5.0 and 6.5 e.g. about 5.7.

A composition including a component adsorbed to an insoluble metal salt can also include a buffer (e.g. a phosphate or a histidine or a Tris buffer).

Because of the insolubility of adsorptive metal salts which are useful with the invention, compositions containing adsorbed components will generally be suspensions having a cloudy appearance. This can mask contaminating bacterial growth and so the method of manufacturing a composition from a batch an adsorbed component (which has been assayed by flow cytometry) may include the step of adding a preservative such as thiomersal or 2-phenoxyethanol. It is preferred that a composition should be substantially free from (e.g. <10 μg/ml) mercurial material e.g. thiomersal-free. Methods of manufacturing a composition containing no mercury are more preferred. Thus a method of the invention may comprise the step of removing mercurial material from a suspension of adsorbed component.

A composition can include a mixture of both an aluminium oxyhydroxide and an aluminium hydroxyphosphate, and adsorbed components may be adsorbed to one or both of these salts.

The concentration of Al$^{+++}$ in a composition for administration to a patient is preferably less than 10 mg/ml e.g. ≤5 mg/ml, ≤4 mg/ml, ≤3 mg/ml, ≤2 mg/ml, ≤1 mg/ml, etc. A preferred range is between 0.3 and 1 mg/ml. A maximum of <0.85 mg/dose is preferred. The concentration of Al$^{+++}$ in the pharmaceutical composition may differ from the concentration in the suspension analysed by the flow cytometry method of the invention.

Immunogens

The invention is particularly useful for assaying adsorbed components in, or for incorporation into, immunogenic compositions. Adsorbed components assayed by the method of the invention may be useful during immunisation.

The invention can be used with a wide range of adsorbed components which can be used for treating or protecting against a wide range of diseases. The adsorbed component may elicit an immune response that protects against a viral disease (e.g. due to an enveloped or non-enveloped virus), a bacterial disease (e.g. due to a Gram negative or a Gram positive bacterium), a fungal disease, a parasitic disease, an auto-immune disease, or any other disease. The adsorbed component may also be useful in immunotherapy e.g. for treating a tumour/cancer, Alzheimer's disease, or an addiction.

The adsorbed component may take various forms e.g. a whole organism, an outer-membrane vesicle, a polypeptide, a saccharide, a liposaccharide, a conjugate (e.g. of a carrier and a hapten, or of a carrier and a saccharide or liposaccharide), etc. Where the adsorbed component is a polypeptide, it will typically be a surface polypeptide e.g. an adhesin, a hemagglutinin, an envelope glycoprotein, a spike glycoprotein, etc.

The adsorbed component may elicit an immune response against an influenza virus, including influenza A and B viruses. Various forms of influenza virus immunogen are currently available, typically based either on live virus or on inactivated virus. Inactivated vaccines may be based on whole virions, split virions, or on purified surface antigens. Influenza antigens can also be presented in the form of virosomes. Hemagglutinin is the main adsorbed component in current inactivated vaccines, and vaccine doses are standardised by reference to HA levels, typically measured by SRID. Existing vaccines typically contain about 15 μg of HA per strain, although lower doses can be used e.g. for children, or in pandemic situations, or when using an adjuvant. Fractional doses such as ½ (i.e. 7.5 μg HA per strain), ¼ and ⅛ have been used, as have higher doses (e.g. 3× or 9× doses [8,9]). Thus compositions may include between 0.1 and 150 μg of HA per influenza strain, preferably between 0.1 and 50 μg e.g. 0.1-20 μg, 0.1-15 μg, 0.1-10 μg, 0.1-7.5 μg, 0.5-5 μg, etc. Particular doses include e.g. about 45, about 30, about 15, about 10, about 7.5, about 5, about 3.8, about 3.75, about 1.9, about 1.5, etc. per strain. It is usual to include substantially the same mass of HA for each strain included in the vaccine e.g. such that the HA mass for each strain is within 10% of the mean HA mass per strain, and preferably within 5% of the mean. For live vaccines, dosing is measured by median tissue culture infectious dose (TCID$_{50}$) rather than HA content, and a TCID$_{50}$ of between 10$^6$ and 10$^8$ (preferably between 10$^{6.5}$-10$^{7.5}$) per strain is typical. Rather than use SPF eggs as the substrate for viral growth, where virus is harvested from infected allantoic fluids of hens' eggs, cell lines that support influenza virus replication may be used. The cell line will typically be of mammalian origin e.g. MDCK. Influenza A virus adsorbed components may be from any suitable HA subtype strain e.g. H1, H3, H5, H7, H9 etc., such as a H1N1, H3N2 and/or H5N1 strain.

The adsorbed component may elicit an immune response against a *Candida* fungus such as *C. albicans*. For instance, the adsorbed component may be a β-glucan, which may be conjugated to a carrier protein. The glucan may include β-1,3 and/or β-1,6 linkages. Suitable adsorbed components include those disclosed in references 10 & 11.

The adsorbed component may elicit an immune response against a *Streptococcus* bacterium, including *S. agalactiae, S. pneumoniae* and *S. pyogenes*. For instance, the adsorbed component may be a capsular saccharide, which may be conjugated to a carrier protein. For *S. agalactiae* the saccharide may be from one or more of serotypes Ia, Ib, II, III, and/or V. For *S. pneumoniae* the saccharide may be from one or more of serotypes 1, 3, 4, 5, 6B, 7F, 9V, 14, 18C, 19F, and/or 23F. In addition to (or in place of) capsular saccharide immunogen(s), polypeptide adsorbed components may be used to elicit a protective anti-streptococcal immune response e.g. comprising RrgB, as disclosed in reference 12.

The adsorbed component may elicit an immune response against a *Staphylococcus* bacterium, including *S. aureus* or *S. epidermidis*. For instance, the immunogen may comprise an IsdA antigen, an IsdB antigen, a ClfA antigen, a ClfB antigen, a SdrD antigen, a Spa antigen, an EsxA antigen, an EsxB antigen, a Sta006 antigen, a hemolysin, and/or a Sta011 antigen. Suitable *S. aureus* immunogens and their combinations are disclosed in reference 13.

The adsorbed component may elicit an immune response against a meningococcal bacterium (*Neisseria meningitidis*). For instance, the adsorbed component may be a capsular saccharide, which may be conjugated to a carrier protein. Capsular saccharides are particularly useful for protecting against meningococcal serogroups A, C, W135 and/or Y. In addition to (or in place of) capsular saccharide adsorbed component(s), polypeptide adsorbed components and/or outer membrane vesicles may be used to elicit a protective anti-meningococcal immune response, particularly for use against serogroup B e.g. as disclosed in reference 14.

The adsorbed component may elicit an immune response against a hepatitis virus, such as a hepatitis A virus, a hepatitis B virus, a hepatitis C virus and/or a hepatitis E virus. For instance, the adsorbed component may be hepatitis B virus surface antigen (HBsAg).

The adsorbed component may elicit an immune response against a respiratory syncytial virus. Adsorbed components may be from a group A RSV and/or a group B RSV. Suitable immunogens may comprise the F and/or G glycoproteins or fragments thereof e.g. as disclosed in references 15 & 16.

The adsorbed component may elicit an immune response against a Chlamydia bacterium, including *C. trachomatis* and *C. pneumoniae*. Suitable adsorbed components include those disclosed in references 17-23.

The adsorbed component may elicit an immune response against an *Escherichia coli* bacterium, including extraintestinal pathogenic strains. Suitable adsorbed components include those disclosed in references 24-26.

The adsorbed component may elicit an immune response against a coronavirus, such as the human SARS coronavirus. Suitable adsorbed components may comprise the spike glycoprotein.

The adsorbed component may elicit an immune response against a *Helicobacter pylori* bacterium. Suitable adsorbed components include CagA [27-30], VacA [31,32], and/or NAP [33-35].

The adsorbed component may elicit an immune response against rabies virus. A suitable adsorbed component is an inactivated rabies virus [36, RabAvert™].

The adsorbed component may elicit an immune response against a human papillomavirus. Useful immunogens are L1 capsid proteins, which can assemble to form structures known as virus-like particles (VLPs). The VLPs can be produced by recombinant expression of L1 in yeast cells (e.g. in *S. cerevisiae*) or in insect cells (e.g. in *Spodoptera* cells, such as *S. frugiperda*, or in *Drosophila* cells). For yeast cells, plasmid vectors can carry the L1 gene(s); for insect cells, baculovirus vectors can carry the L1 gene(s). More preferably, the composition includes L1 VLPs from both HPV-16 and HPV-18 strains. This bivalent combination has been shown to be highly effective [37]. In addition to HPV-16 and HPV-18 strains, it is also possible to include L1 VLPs from HPV-6 and HPV-11 strains.

The adsorbed component may elicit an immune response against a tumour antigen, such as MAGE-1, MAGE-2, MAGE-3 (MAGE-A3), MART-1/Melan A, tyrosinase, gp100, TRP-2, etc. The adsorbed component may elicit an immunotherapeutic response against lung cancer, melanoma, breast cancer, prostate cancer, etc.

The adsorbed component may elicit an immune response against a hapten conjugated to a carrier protein, where the hapten is a drug of abuse [38]. Examples include, but are not limited to, opiates, marijuana, amphetamines, cocaine, barbituates, glutethimide, methyprylon, chloral hydrate, methaqualone, benzodiazepines, LSD, nicotine, anticholinergic drugs, antipsychotic drugs, tryptamine, other psychomimetic drugs, sedatives, phencyclidine, psilocybine, volatile nitrite, and other drugs inducing physical and/or psychological dependence.

Various other adsorbed components may be used.

Compositions for Immunisation against *Neisseria meningitidis*

The flow cytometry method of the invention is particularly useful for assaying adsorbed components in immunogenic compositions for immunising against meningococcus e.g. against serogroup B.

Preferred immunogenic compositions prepared by the method of manufacturing disclosed herein comprise: (i) an aluminium hydroxide adjuvant; (ii) compound 1, 2 or 5 herein; (iii) a first polypeptide comprising SEQ ID NO: 1; (iv) a second polypeptide comprising SEQ ID NO: 2; and (v) a third polypeptide comprising SEQ ID NO: 3, 4 or 5; wherein compound of (ii) is adsorbed to the aluminium hydroxide.

The polypeptides used with the invention may, compared to the SEQ ID NOs herein, include one or more (e.g. 1, 2, 3, 4, 5, 6, 7, 8, 9, etc.) amino acid substitutions, such as conservative substitutions (i.e. substitutions of one amino acid with another which has a related side chain). Genetically encoded amino acids are generally divided into four families: (1) acidic i.e. aspartate, glutamate; (2) basic i.e. lysine, arginine, histidine; (3) non-polar i.e. alanine, valine, leucine, isoleucine, proline, phenylalanine, methionine, tryptophan; and (4) uncharged polar i.e. glycine, asparagine, glutamine, cysteine, serine, threonine, tyrosine. Phenylalanine, tryptophan, and tyrosine are sometimes classified jointly as aromatic amino acids. In general, substitution of single amino acids within these families does not have a major effect on the biological activity. The polypeptides may also include one or more (e.g. 1, 2, 3, 4, 5, 6, 7, 8, 9, etc.) single amino acid deletions relative to the SEQ ID NO sequences. The polypeptides may also include one or more (e.g. 1, 2, 3, 4, 5, 6, 7, 8, 9, etc.) insertions (e.g. each of 1, 2, 3, 4 or 5 amino acids) relative to the SEQ ID NO sequences.

Ideally, 1 2 or 3 of the first second and/or third polypeptides is/are also adsorbed to the aluminium hydroxide. These polypeptides are disclosed in more detail in references 14 and 39. The composition produced by the method of manufacturing may include 5-100 µg of each polypeptide. The composition ideally does not include any bacterial outer membrane vesicles.

The composition produced by the method of manufacturing may include from 5-100 µg of compound 1, 2 or 5. For example, it may include from 5-100 µg of compound 2, or it may include from 5-100 µg of compound 5.

The composition may include a histidine buffer e.g. a 10 mM histidine buffer. It may include sucrose and/or sodium chloride. It may be administered in a dosage volume of 0.5 ml e.g. for intramuscular injection.

Agonists

The adsorbed component for analysis by the method of the invention may be an agonist of a receptor. The adsorbed agonist may be the naturally occurring cognate ligand of the receptor. In an alternative, the adsorbed agonist may be a non-naturally occurring ligand of the receptor. In further alternatives, the adsorbed agonist may be a peptide mimetic of the receptor or a small molecule capable of binding to the receptor. An example of a small molecule capable of binding to the receptor is a SMIP (small molecule immunopotentiator).

For example, the adsorbed component may be a TLR agonist which comprises an adsorptive moiety and a TLR agonist moiety. The adsorptive moiety confers the ability to adsorb to an insoluble metal salt (see above), whereas the TLR agonist moiety confers the ability to agonise a Toll-like receptor. Typically a TLR agonist assayed by the method of the invention would thus function as a TLR agonist even without its adsorptive moiety. Except where otherwise stated, TLR agonists can activate any of TLR1, TLR2, TLR3, TLR4, TLR5, TLR6, TLR7, TLR8, TLR9 or TLR11.

Where the a compound is referred to as a TLR agonist, the compound is preferably an agonist of TLR1, TLR2, TLR3, TLR4, TLR5, TLR6, TLR7, TLR8, TLR9, TLR10 or TLR11. From this group, a preferred sub-group is TLR1, TLR2, TLR3, TLR5, TLR6, TLR7, TLR8 and TLR11. A more preferred subgroup is TLR2, TLR7 and TLR8. Another preferred subgroup is TLR2 and TLR7.

Most preferably, a TLR agonist is an agonist of a human TLR.

Numerous other agonists which increase the immune response of a subject are suitable for use as adsorbed components for analysis by the method of the invention.

Pharmaceutical Compositions and Products

The method of the invention can be used to analyse components adsorbed to insoluble metal salts from a batch of adsorbed component which is then used in the manufacture of pharmaceutical compositions and products. The assayed batch of adsorbed component can be formulated in numerous ways, and the formulation can comprise many further components.

A pharmaceutical composition comprising the adsorbed component may be generated by the addition of one or more pharmaceutically acceptable excipients. A thorough discussion of such components is available in reference 40.

Pharmaceutical compositions comprising the adsorbed component are preferably in aqueous form, particularly at the point of administration, but they can also be presented in non-aqueous liquid forms or in dried forms e.g. as gelatin capsules, or as lyophilisates, etc., following analysis by a method of the present invention. Thus a method of the invention may comprise the step of lyophilising a suspension of an adsorbed component.

Pharmaceutical compositions comprising the adsorbed component may include one or more preservatives, such as thiomersal or 2-phenoxyethanol. Mercury-free compositions are preferred, and preservative-free vaccines can be prepared. Thus a method of the invention may comprise the step of adding a preservative.

Pharmaceutical compositions comprising the adsorbed component can include a physiological salt, such as a sodium salt e.g. to control tonicity. Sodium chloride (NaCl) is typical, which may be present at between 1 and 20 mg/ml e.g. 10±2 mg/ml or 9 mg/ml. Other salts that may be present include potassium chloride, potassium dihydrogen phosphate, disodium phosphate dehydrate, magnesium chloride, calcium chloride, etc. Thus a method of the invention may comprise the step of adding a physiological salt.

Pharmaceutical compositions comprising the adsorbed component can have an osmolality of between 200 mOsm/kg and 400 mOsm/kg, e.g. between 240-360 mOsm/kg, or between 290-310 mOsm/kg. Thus a method of the invention may comprise the step of adjusting the osmolality of the suspension of adsorbed component to between 200 mOsm/kg and 400 mOsm/kg, e.g. between 240-360 mOsm/kg, or between 290-310 mOsm/kg. Pharmaceutical compositions comprising the adsorbed component may include compounds in plain water (e.g. w.f.i.) but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range. Thus a method of the invention may comprise the step of adding or exchanging the buffer in a suspension of adsorbed component, for example to a phosphate buffer, a Tris buffer, a borate buffer, a succinate buffer or a histidine buffer.

Pharmaceutical compositions comprising the adsorbed component typically have a pH between 5.0 and 9.5 e.g. between 6.0 and 8.0. Thus a method of the invention may comprise the step of adjusting the pH of a suspension of adsorbed component, optionally to between 5.0 and 9.5 e.g. between 6.0 and 8.0.

Pharmaceutical compositions are preferably sterile. Thus a method of the invention may comprise the step of sterilising a suspension of adsorbed component.

Pharmaceutical compositions preferably non-pyrogenic e.g. containing <1 EU (endotoxin unit, a standard measure) per dose, and preferably <0.1 EU per dose. Thus a method of the invention may comprise the step of removing endotoxin from a suspension of adsorbed component.

Pharmaceutical compositions are preferably gluten free. Thus a method of the invention may comprise the step of removing gluten from a suspension of adsorbed component.

Pharmaceutical compositions prepared by the method of manufacture of the invention are suitable for administration to animal (and, in particular, human) patients, and thus include both human and veterinary uses. They may be used in a method of raising an immune response in a patient, comprising the step of administering the composition to the patient.

Pharmaceutical compositions may be prepared in unit dose form. In some embodiments a unit dose may have a volume of between 0.1-1.0 ml e.g. about 0.5 ml. Thus a method of the invention may comprise the step of preparing a unit dose.

Pharmaceutical compositions assayed by the methods of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilised composition or a spray-freeze dried composition). The composition may be prepared for topical administration e.g. as an ointment, cream or powder. The composition may be prepared for oral administration e.g. as a tablet or capsule, as a spray, or as a syrup (optionally flavoured). The composition may be prepared for pulmonary administration e.g. by an inhaler, using a fine powder or a spray. The composition may be prepared as a suppository or pessary. The composition may be prepared for nasal, aural or ocular administration e.g. as a spray or drops. The composition may be in kit form, designed such that a combined composition is reconstituted just prior to administration to a patient. Such kits may comprise one or more antigens in liquid form and one or more lyophilised antigens. Injectables for intramuscular administration are typical. Thus a method of the invention may comprise the step of preparing an injectable.

Compositions comprise an effective amount of one or more adjuvanted components i.e. an amount which, when administered to an individual, either in a single dose or as part of a series, is effective for enhancing the immune response. This amount can vary depending upon the health and physical condition of the individual to be treated, age, the taxonomic group of individual to be treated (e.g. non-human primate, primate, etc.), the capacity of the individual's immune system to synthesise antibodies, the degree of protection desired, the formulation of the vaccine, the treating doctor's assessment of the medical situation, and other relevant factors. The amount will fall in a relatively broad range that can be determined through routine trials. An amount of between 1-1000 m/dose can be used e.g. from 10-100 μg per dose. Thus a method of the invention may comprise the step of diluting or concentrating the adsorbed component to achieve a concentration suitable for preparing a unit dose.

General

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

Unless specifically stated, a process comprising a step of mixing two or more components does not require any specific order of mixing. Thus components can be mixed in any order. Where there are three components then two components can be combined with each other, and then the combination may be combined with the third component, etc.

Where animal (and particularly bovine) materials are used in the culture of cells, they should be obtained from sources that are free from transmissible spongiform encephalopathies (TSEs), and in particular free from bovine spongiform encephalopathy (BSE). Overall, it is preferred to culture cells in the total absence of animal-derived materials.

Where a compound is administered to the body as part of a composition then that compound may alternatively be replaced by a suitable prodrug.

The term "antibody" includes any of the various natural and artificial antibodies and antibody-derived proteins which are available, and their derivatives, e.g. including without limitation polyclonal antibodies, monoclonal antibodies, chimeric antibodies, humanized antibodies, human antibodies, single-domain antibodies, whole antibodies, antibody fragments such as F(ab')2 and F(ab) fragments, Fv fragments (non-covalent heterodimers), single-chain antibodies such as single chain Fv molecules (scFv), minibodies, oligobodies, dimeric or trimeric antibody fragments or constructs, etc. The term "antibody" does not imply any particular origin, and includes antibodies obtained through non-conventional processes, such as phage display. Antibodies of the invention can be of any isotype (e.g. IgA, IgG, IgM i.e. an α, γ or μ heavy chain) and may have a κ or a λ light chain.

BRIEF DESCRIPTION OF THE DRAWINGS

FIGS. 2a-2g are a series of histograms showing an increase in fluorescence detected with increasing concentrations of NadA (FIG. 2a) 0 μg m$^{-1}$ (FIG. 2b) 50 μg ml$^{-1}$ (FIG. 2c) 100 μg ml$^{-1}$ (FIG. 2d) 200 μg ml$^{-1}$ (FIG. 2e) 400 μg ml$^{-1}$ (FIG. 2f) 800 μg ml$^{-1}$ and (FIG. 2g) 1600 μg ml$^{-1}$. The left hand peak in each image represents aluminium hydroxide particles without adsorbed component. With increasing concentration, a larger proportion of particles are seen to shift to the right, indicating an elevated level of fluorescence from a label specifically attached to NadA.

FIGS. 3a-3d are a series of histograms showing the results of the tests for autoflorescence of the assay components. The histograms represent the event counts versus the fluorescence measured for the APC-A channel 660/20. (FIG. 3a) Analysis of aluminium hydroxide by flow cytometry identifies 99% of the aggregates as having fluorescence intensity less than 1000. (FIGS. 3b, 3c, 3d) Similar analyses of aluminium hydroxide together with assay components (NadA (b), NadA+BSA (FIG. 3c), and NadA, BSA and anti-NadA rabbit antibody (FIG. 3d)) indicated no inherent fluorescence over the background level for the antigen NadA, the blocking agent (BSA) or by the primary antibody.

FIGS. 4a-4c are a series of histograms showing the specificity of antibody binding to NadA adsorbed to aluminium hydroxide. The histograms represent the event counts in percentage (%) versus the relative fluorescence intensity measured for the APC-Alexa 647 at channel 660/20 for various sample controls. (FIG. 4a) Non-specific binding was determined by performing the flow cytometry assay in absence of antigen with primary antibody diluted 1:1000 and 1:1000 or containing 100 μg ml$^{-1}$ NadA but using irrelevant primary antibody. (FIG. 4b) The BSA treatment was successful in blocking the level of fluorescence for aluminium hydroxide particles (left peak) by 10-fold lower to the levels measured for the complete assay with NadA formulated at 100 μg ml$^{-1}$ (right peak). (FIG. 4c) The assay is highly reproducible, and only minor variation was observed between identical formulations assay at time 0 and 24 h apart or after waiting 24 h following the antibody staining (three overlapping peaks).

FIGS. 6a-6g are a series of scatter plots forming an analysis of the antigen distribution of NadA on aluminium hydroxide aggregates using side scattering and relative fluorescence intensity (RFI). The percentage of florescent particles increases with the concentration of NadA (0, 9.375, 18.75, 37.5, 75, 150, 300 μgml$^{-1}$). FIG. 6a shows the percentage of fluorescent particles at a concentration of 0 μg/ml$^{-1}$ NadA. FIG. 6b shows the percentage of fluorescent particles at a concentration of 9.375 μg/ml$^{-1}$ NadA. FIG. 6c shows the percentage of fluorescent particles at a concentration of 18.75 μg/ml$^{-1}$ NadA. FIG. 6d shows the percentage of fluorescent particles at a concentration of 37.5 μg/ml$^{-1}$ NadA. FIG. 6e shows the percentage of fluorescent particles at a concentration of 75 μg/ml$^{-1}$ NadA. FIG. 6f shows the percentage of fluorescent particles at a concentration of 150 μg/ml$^{-1}$ NadA. FIG. 6g shows the percentage of fluorescent particles at a concentration of 300 μg/ml$^{-1}$ NadA.

FIGS. 9a-9d are a series of scatter plots providing a morphological analysis of aluminium hydroxide-Compound C formulation and controls based on forward and side scatter parameters (FSC and SSC). (FIG. 9a) Aluminium hydroxide, (FIG. 9b) Compound C (FIG. 9c) Filtered compound C and (FIG. 9d) Compound C adsorbed to aluminium hydroxide.

FIGS. 10a-10c are a series of scatter plots providing a morphological analysis of aluminium hydroxide +Compound A formulation and relative controls based on forward and side scatter parameters (FSC and SSC). (FIG. 10a) Aluminium hydroxide, (FIG. 10b) Compound A, (FIG. 10c) Compound A with aluminium hydroxide.

(FIGS. 11a, 11h) 0 µg ml$^{-1}$, (FIGS. 11b, 11i) 50 µg ml$^{-1}$, (FIGS. 11c, 11j) 100 µg ml$^{-1}$, (FIGS. 11d, 11k) 150 µg ml$^{-1}$, (FIGS. 11e, 11$^{-1}$) 200 µg ml$^{-1}$, (FIGS. 11f, 11m) 250 µg ml$^{-1}$, (FIGS. 11g,) 400 µg ml$^{-1}$, and (FIGS. 11n) 300 µg ml$^{-1}$.

FIGS. 15a-15d are a series of scatter plots providing a morphological analysis of aluminium hydroxide-Compound E formulation and controls based on forward and side scatter parameters (FSC and SSC) and a series of histograms showing fluorescence traces for aluminium hydroxide formulations for Compound E. (FIG. 15a) PBS/PBS, (FIG. 15b) 153/153, (FIG. 15c) PBS/Alum, (FIG. 15d) Alum LHD153/Alum LHD153.

MODES FOR CARRYING OUT THE INVENTION

Figure 1:
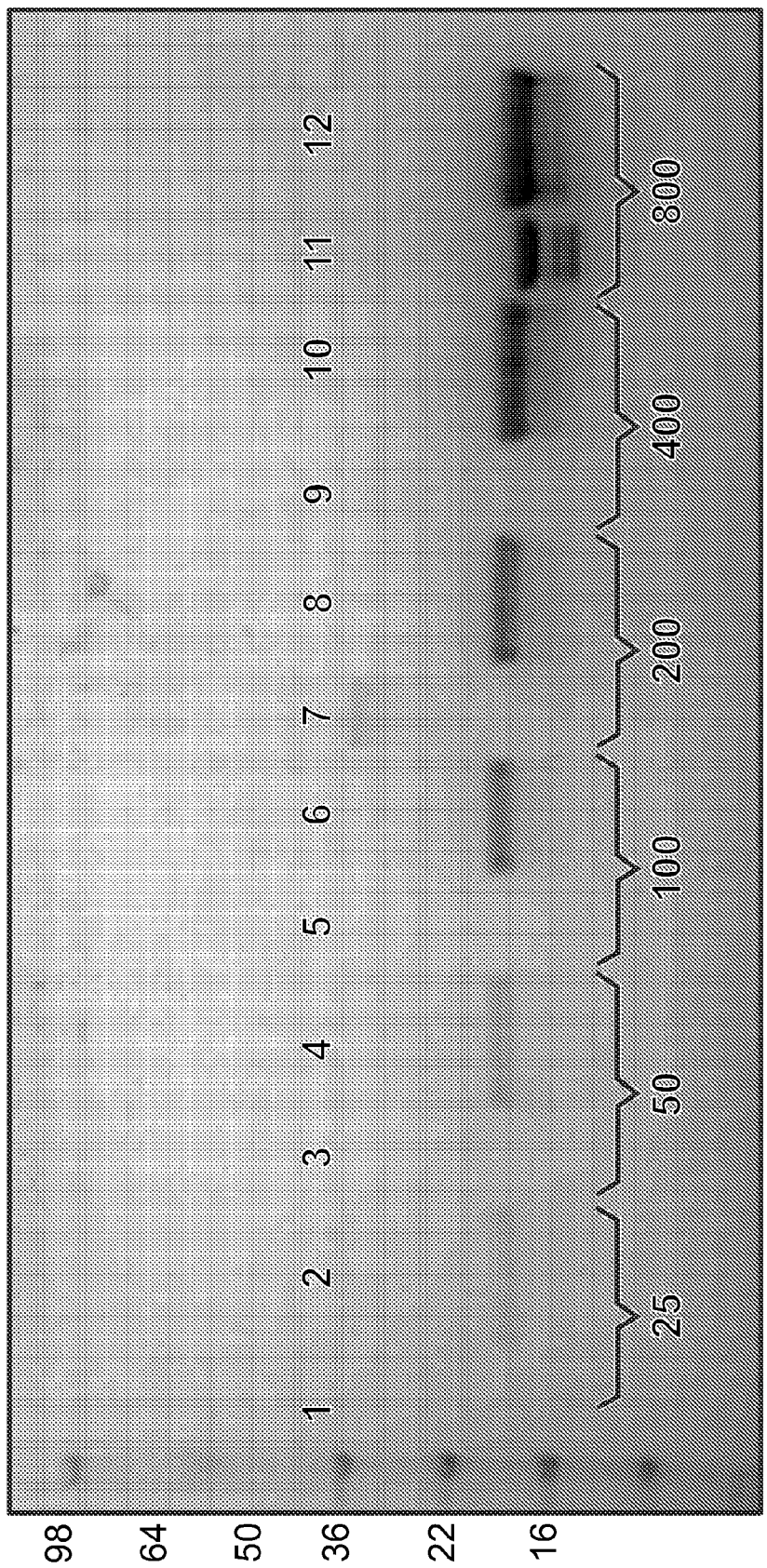
FIG. 1 is an image of an SDS-PAGE gel displaying the adsorption capacity of aluminium hydroxide for the antigen NadA. Odd numbered lanes are supernatant treated with deoxycholic acid sodium salt (DOC) and trichloroacetic acid (TCA) of aluminium hydroxide adsorbed samples at 50, 100, 200, 400, 800 and 1600 μg ml$^{-1}$ of NadA. Even lanes are aluminium hydroxide pellet desorbed samples from formulation with: 50, 100, 200, 400, 800 and 1600 μg ml$^{-1}$ of NadA. Each sample contained 3000 μg ml$^{-1}$ aluminium hydroxide.
Figure 2B:
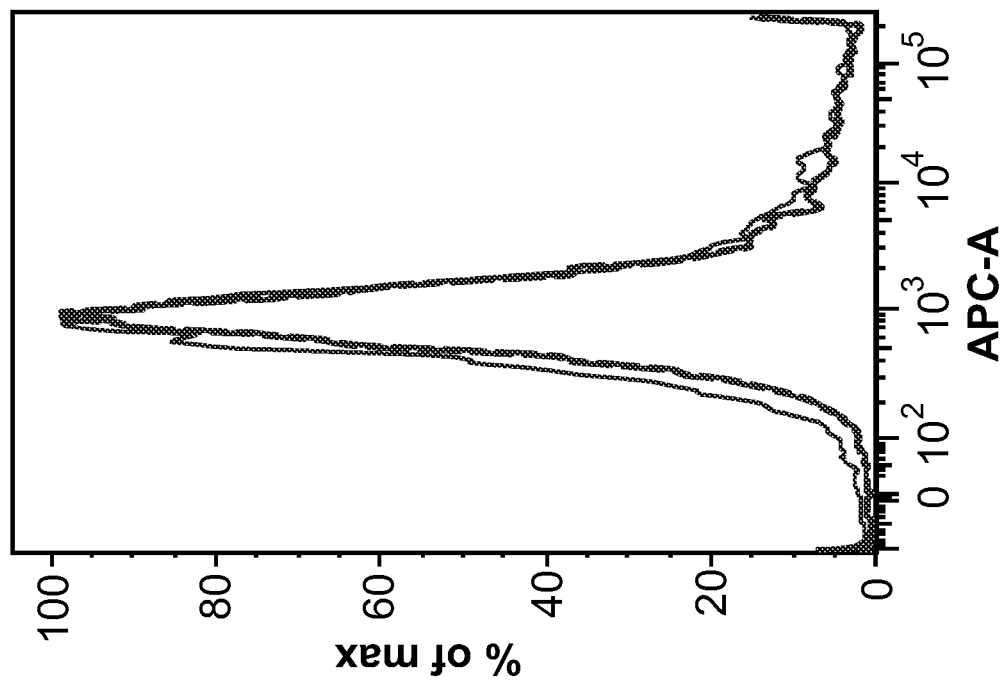
Figure 2A:
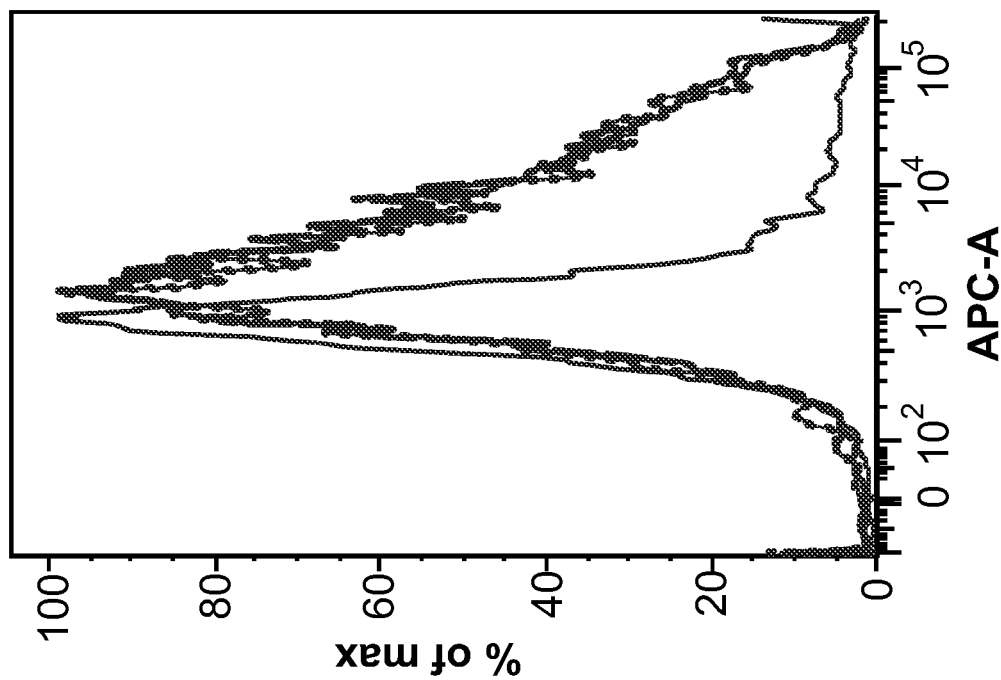
Figure 2D:
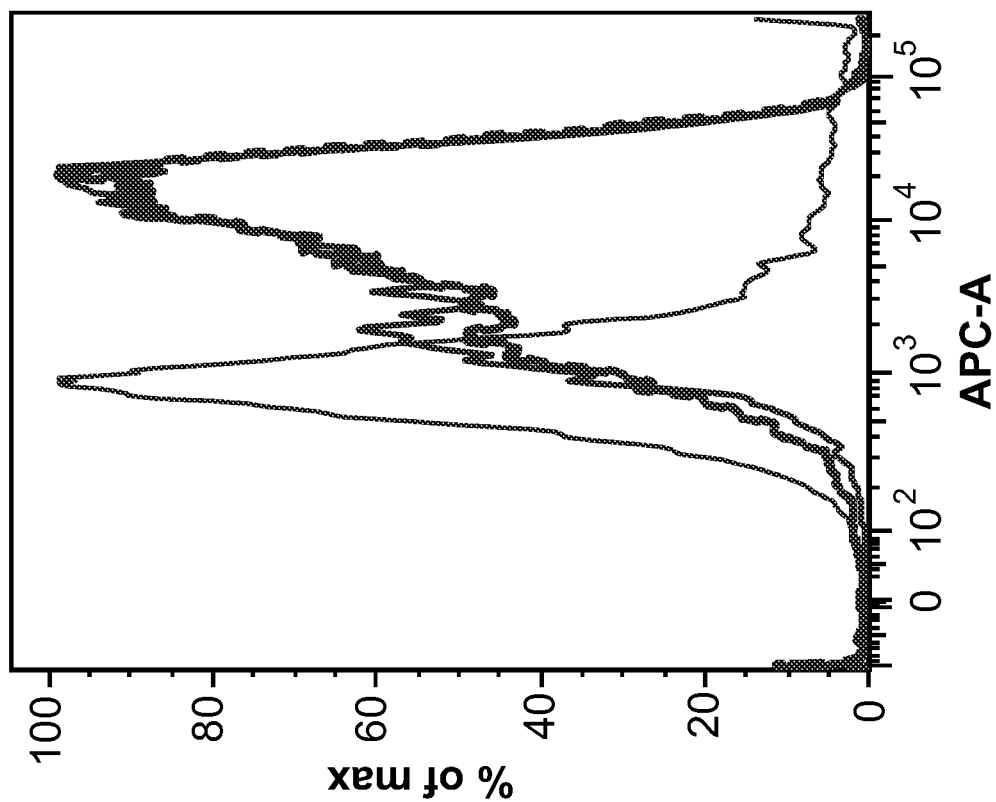
Figure 2C:
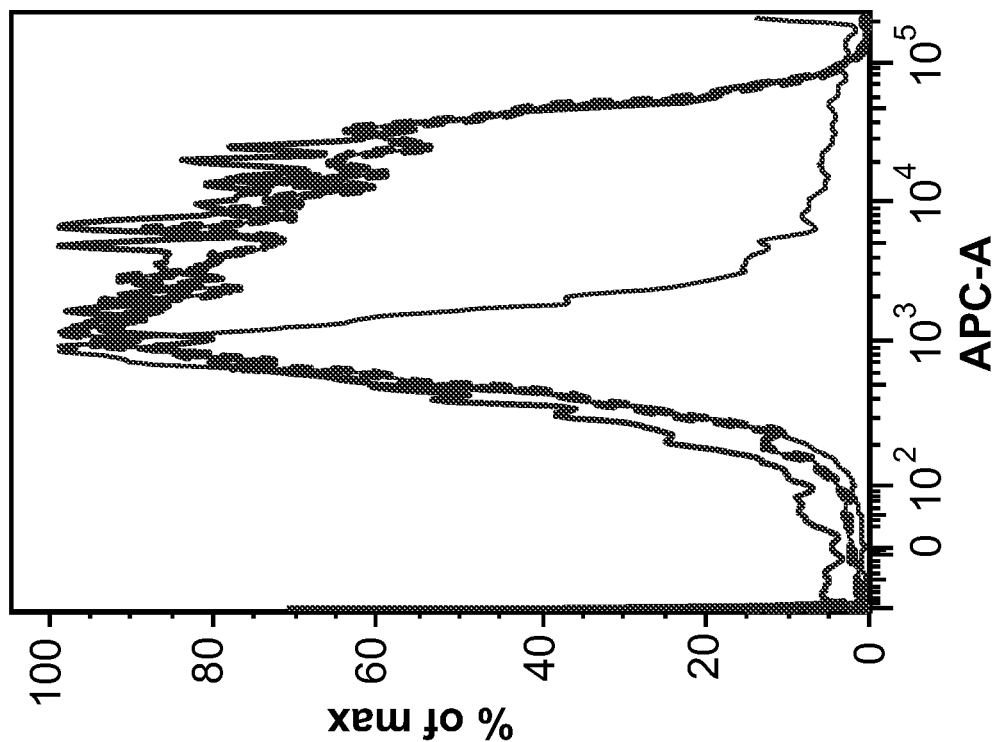
Figure 2G:
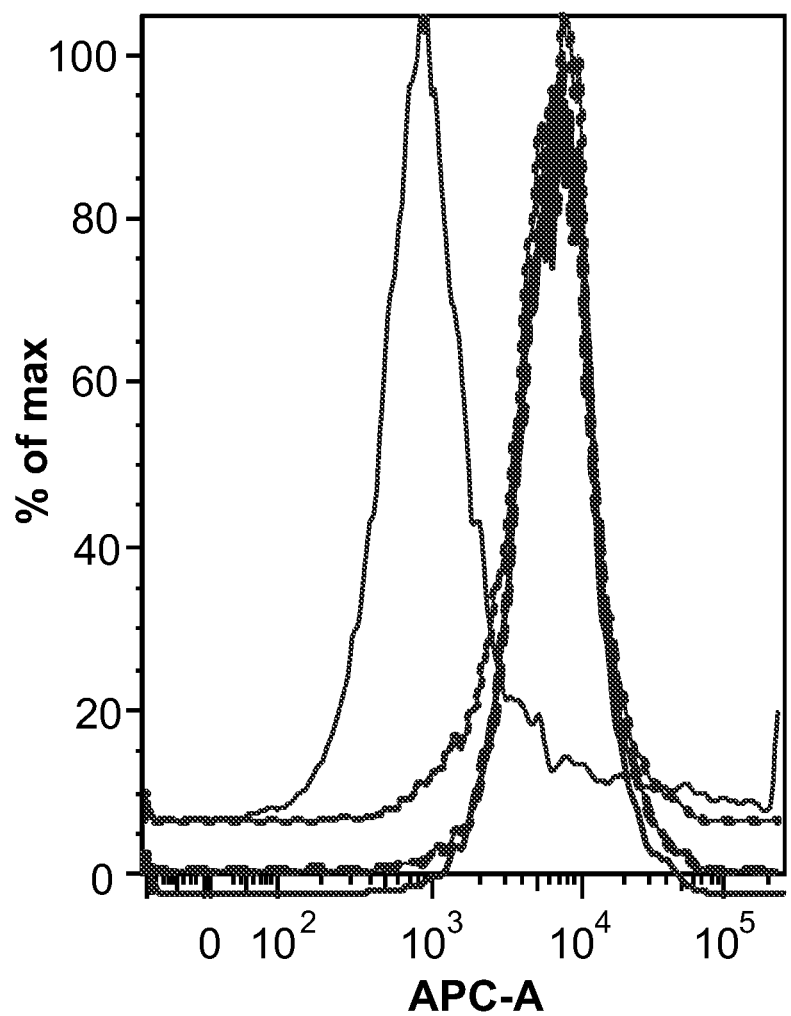

Further information for implementing the invention can be obtained from reference 41.

Flow Cytometry Analysis of Adsorbed Protein
Materials

Clinical grade material (GMP) of a recombinant protein antigen of *Neisseria meningitidis* serogroup B (MenB) NadA was used for the experiments. Anti-NadA polyclonal rabbit antibody was used as primary antibody at 1:500, dilution in 10 mM histidine buffer, pH 6.5. Alexa Fluor 647 F(ab')2 fragment of goat anti-rabbit antibody was purchased from Molecular Probes and used at 1:800 dilution in 1×PBS. This antibody was utilized as the final step of the assay.
Preparation of Standards and Samples Formulations A set of standard suspensions containing the antigen NadA at 300 µg ml$^{-1}$ and five serial two-fold dilutions was prepared by serially diluting a stock suspension sample the day before the assay.

The stock suspension was prepared by mixing 1500 µg of aluminium hydroxide per 150 µg of NadA in 10 mM histidine buffer (pH 6.5). The final osmolarity of the formulation was adjusted to 300 mOsm/L using a 2M NaCl solution. The concentration of aluminium hydroxide in the stock solution was 3000 µg ml$^{-1}$ and the concentration of NadA was 300 µg ml$^{-1}$. The antigen was adsorbed by stirring the stock suspension for at least two hours at 4° C. Subsequently, the stock suspension was serially diluted, to 9.38 µg ml$^{-1}$, by mixing 1 ml aluminium hydroxide-antigen suspension with 1 ml of aluminium hydroxide suspension, which had been previously adjusted for concentration, pH and osmolarity. The samples were used for assaying after an overnight incubation under rocking motion at 4° C. For each assay, blank samples containing 3000 µg ml$^{-1}$ of aluminium hydroxide, adjusted to pH and osmolarity, were included as part of the standard set. In parallel, six check standard samples containing 6.25, 12.5, 25, 50 100 and 200 µg ml$^{-1}$ of antigen, were prepared independently by an individual dilution from another stock suspension sample of 3000 µg ml$^{-1}$ of aluminium hydroxide with 300 µg ml$^{-1}$ of NadA prepared exactly as previously described. The dose volume and the aluminium hydroxide concentration for each standard and check sample were respectively 500 µl and 1500 µg/dose (human dose).

The aluminium hydroxide binding capacity (3000 µg ml$^{-1}$ in 10 mM histidine pH 6.5, 300 mOsm/L) was evaluated for several formulations of NadA at 50, 100, 200, 400, 800 and 1600 ml$^{-1}$. To determine antigen adsorption, each formulation was centrifuged at 3000 g for 20 minutes and the supernatant was removed without disturbing the pellet. To precipitate the possible unbound antigens, the supernatants were treated with 0.5% deoxycholic acid sodium salt (DOC), incubated for 10 min at room temperature, followed by the addition of 60% trichloroacetic acid (TCA). The TCA pellets were re-suspended with sample buffer while the aluminium pellets were re-constituted with sample buffer containing 0.5 M Sodium phosphate at pH 8. Samples were loaded into a NUPAGE Novex 4-12% gradient Bis-Tris Midi gel and run under reducing conditions at a constant voltage of 200 V for approximately 50 minutes. The gels were stained-destained with colloidal blue staining kit.

At the clinical dose of 50 µg (100 µg ml$^{-1}$), NadA antigen is predominantly adsorbed to the aluminium hydroxide adjuvant. Any unabsorbed antigen in the formulation supernatant was below the limit of detection (<2%; FIG. 1). Furthermore, unabsorbed NadA in the formulation supernatant was not detectable at an antigen concentration of 800 µg/ml indicating ≥98% adsorption at this antigen concentration. Antigen was, however, detectable at 1600 µg/ml indicating that the adsorptive capacity of 1500 µg of aluminium hydroxide for NadA lies somewhere between 800 and 1600 µg/ml of NadA, and that at the clinical dose of 50 µg the amount of NadA adsorbed is significantly below the adsorptive capacity limit of the adjuvant of 1500 µg per dose in 10 mM histidine pH 6.5.

Flow Cytometry Assay

The assay utilized to analyse the NadA adsorbed to insoluble aluminium hydroxide was a three-step procedure: the saturation of the free sites on the aluminium hydroxide, the primary binding with an antibody that specifically recognizes the antigen NadA and the staining with a fluorescently labelled secondary antibody that binds to the first antibody.

First the BSA was added to the adsorbed component composition, followed by a 30 minute incubation at 4° C. using a vertical rotary mixer. After this step primary antibody was added, and followed by a further 30 minute incubation at 4° C. using a vertical rotary mixer. The secondary antibody was added followed by incubation for 20 minutes at room temperature without mixing, in the dark. The blank, standard and check samples were placed on 96-microwell polypropylene plates. The 75 µl/well suspensions were saturated with 25 µl of 10% BSA in 10 mM histidine buffer pH 6.5. After the incubation, plates were centrifuged (3000 g for 5 minutes) and the supernatants were removed. The aluminium pellets were then washed and centrifuged twice with 100 µl of 10 mM histidine buffer pH 6.5. To reduce the background, the primary antibody, rabbit anti-NadA, was pre-adsorbed with a goat serum (diluted 1/10 in histidine buffer pH 6.5) and subsequently diluted up to 1/500 in histidine buffer pH 6.5. The washed pellets were resuspended with 75 µl of histidine buffer pH 6.5 and 75 µl of primary antibody was subsequently added. Then, the samples were incubated and washed-centrifuged as previously described. Goat anti-rabbit antibody, Alexa Fluor 647® fluorescently labelled, was diluted 1/800 in PBS 1× and then added to each well. After the incubation, plates were washed and centrifuged and resuspended in 1×PBS. The treated samples were read and acquired on a FACSCanto™ II using filter for APC-A channel (660/20 nm).

Auto Fluorescence of Assay Components

Analysis of aluminium hydroxide by flow cytometry identifies 99% of the aggregates having fluorescence intensity less than 1000. Similar analysis of aluminium hydroxide together with assay components indicated no inherent fluorescence over this background level for the antigen NadA, the BSA used as a blocking agent and the primary antibodies (FIGS. 2a-2g).

Effect of Assay Buffer Systems on Antigen Adsorption

Adsorption of antigens to aluminium hydroxide adjuvants depends on pH, ionic strength and the presence of anions such as phosphate (reference 42). Therefore, it was necessary to evaluate the influence of the assay conditions on NadA adsorption.

The amount of antigen that is released from aluminium hydroxide during each of the blocking, staining and washing was measured in the supernatant of the assay sample after each of these steps (data not shown). Eluted antigen was not detectable in the supernatant until the incubation with the secondary antibody and the final washing step with PBS. Some antigen was displaced from aluminium hydroxide during the final wash with PBS. These were found to be in the range of 5% to 10% of antigen present in the formulation. Substitution of PBS with histidine buffer for this final wash was able to alleviate this effect with no detectable antigen released into the wash buffer (data not shown). The antigen loss following exchange to a PBS buffer was not found to have a significant effect of the predictive capability of the assay to determine, reliably and accurately, the concentration of antigen bound to the insoluble metal salt (see Table 3).

Furthermore, despite these observations, the antigen remained predominantly bound to aluminium hydroxide with recovery of the majority of the antigen from aluminium hydroxide once antibody staining procedure had been completed.

Specificity of Antibody Binding Against Adsorbed Antigen to Aluminium

Analysis of the fluorescence intensity of the standard formulation confirmed that for the aluminium hydroxide at 3000 µg ml$^{-1}$ containing no of NadA, most of the adjuvant aggregates (>99%) had fluorescence intensity less than 1000 (FIG. 3b). While at the NadA concentration of 100 µg ml$^{-1}$ (human dose), the aggregates had a marked increase in relative fluorescence with a mean relative fluorescence 9.6 fold greater than that observed for the no NadA formulation. As antibodies have been reported to adsorb to aluminium hydroxide adjuvant via ligand exchange and electrostatic interactions, it was necessary to investigate whether there is any unspecific binding of the primary and secondary antibodies to aluminium hydroxide in the formulation.

To counter any non-specific binding, aluminium hydroxide was blocked with 2.5% BSA prior to staining with the primary and secondary antibodies. This blocking was successful in limiting non-specific binding, as performing the flow cytometry assay in the absence of antigen with primary antibodies diluted 1:1000 and 1:10000 resulted in levels of fluorescence for the aluminium hydroxide particles 10-fold below levels observed for the complete assay with NadA formulated at 100 µg ml$^{-1}$ (FIG. 3a). Furthermore when the assay was performed with irrelevant primary antibodies not specific for NadA, the levels of fluorescence remained equal to those observed in the absence of antigen, indicating that unspecific binding between NadA and the fluorescently labelled secondary antibody is not significant (FIG. 3a).

To evaluate the stability and reproducibility of the assay, multiple formulations were prepared in parallel but stained and/or analyzed by flow cytometry at different time intervals (FIG. 3c). These data indicate that the assay is highly reproducible because little variation was observed between identical formulations assayed 24 hours apart. Furthermore the assay is stable because waiting 24 hours following the antibody staining procedure of the assay had little impact on the levels of fluorescence measured by flow cytometry analysis.

Morphology and Antigen Distribution of Standard Formulations

Figure 5:
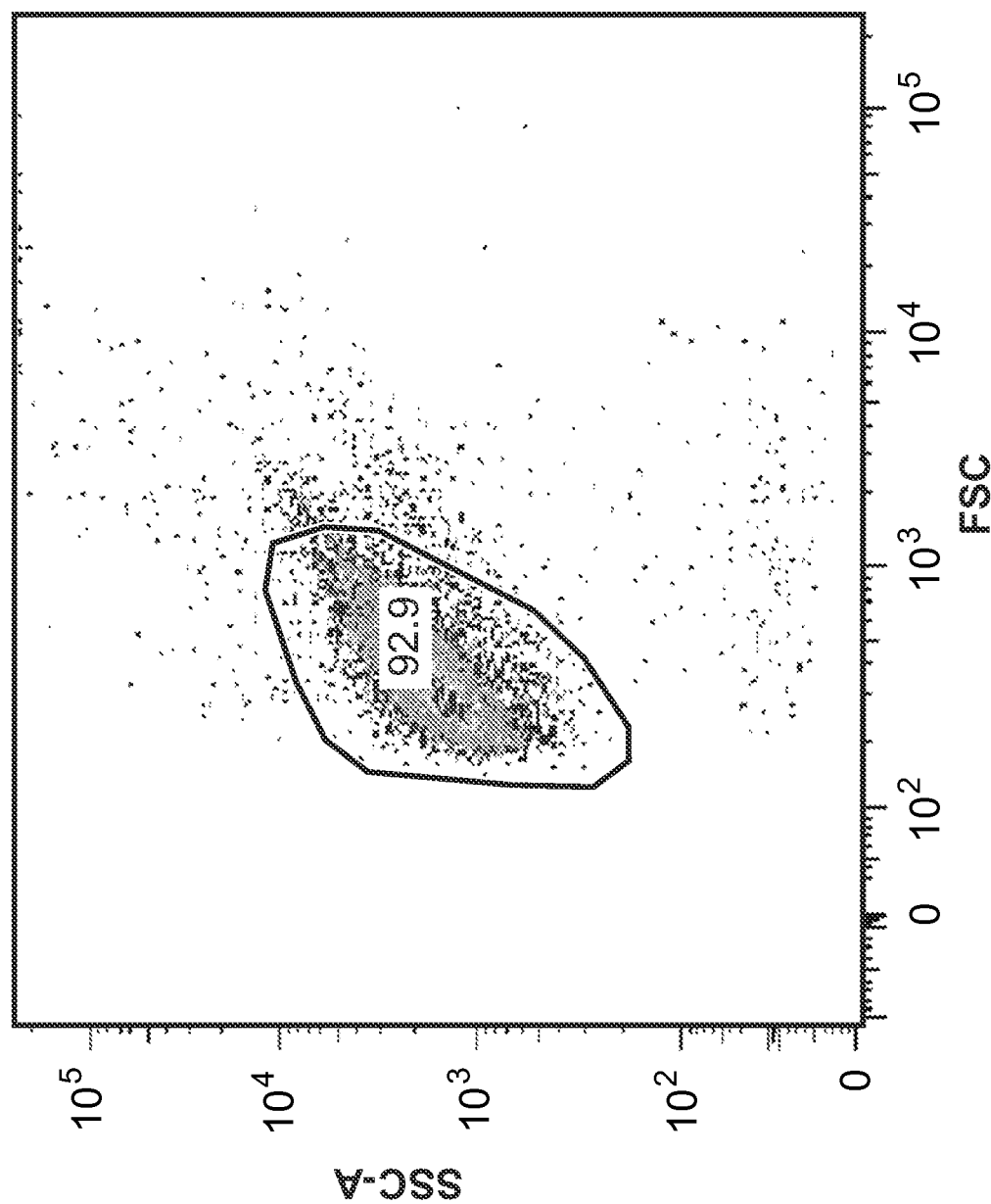
FIG. 5 is a representation of scatter plots for all standard formulations (0-300 μg ml$^{-1}$). The gated dots appeared as a single uniform population of particles with increased concentration of adsorbed NadA having no impact on forward and side scatter measurements.
Figure 6A:
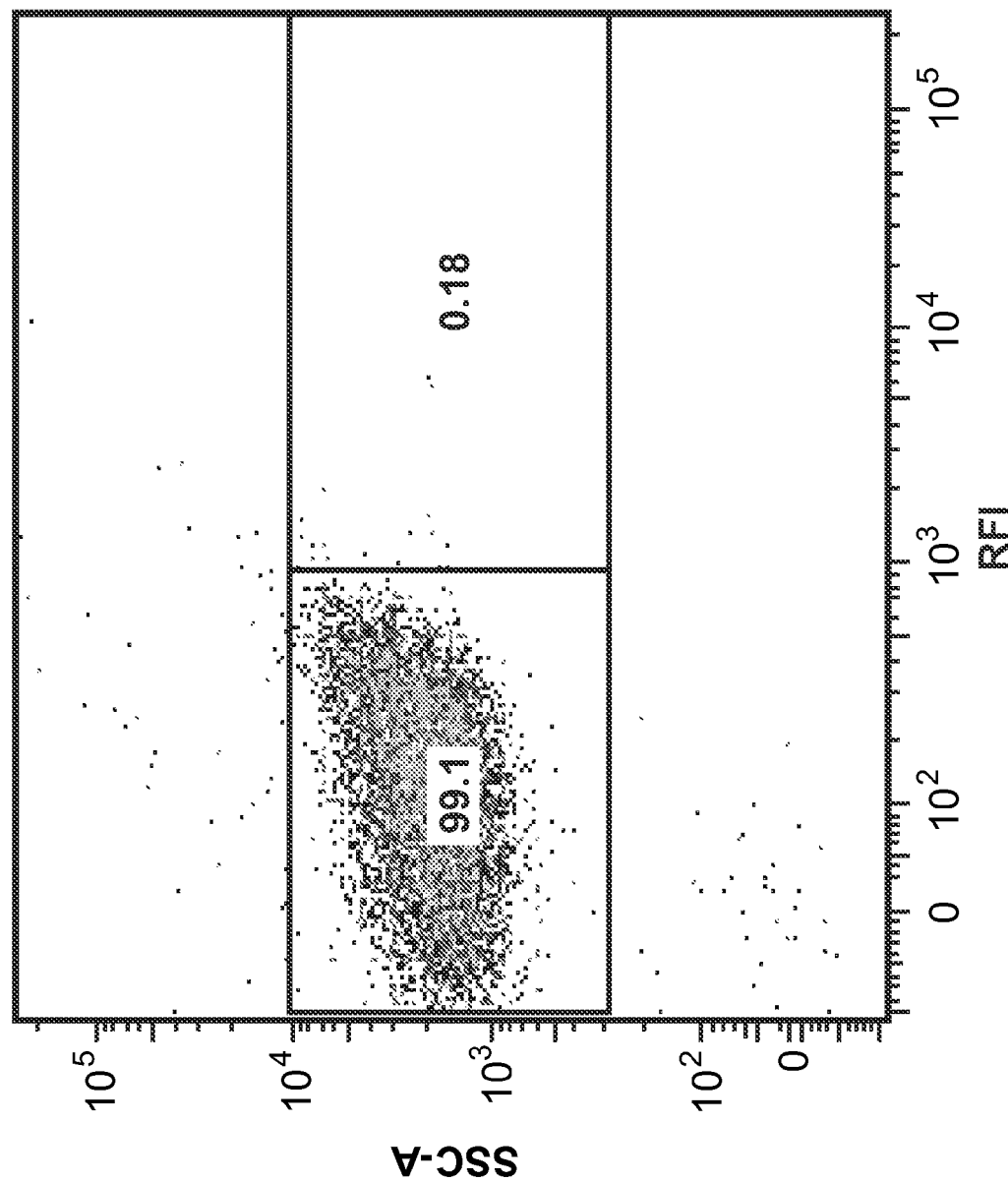
Figure 6E:
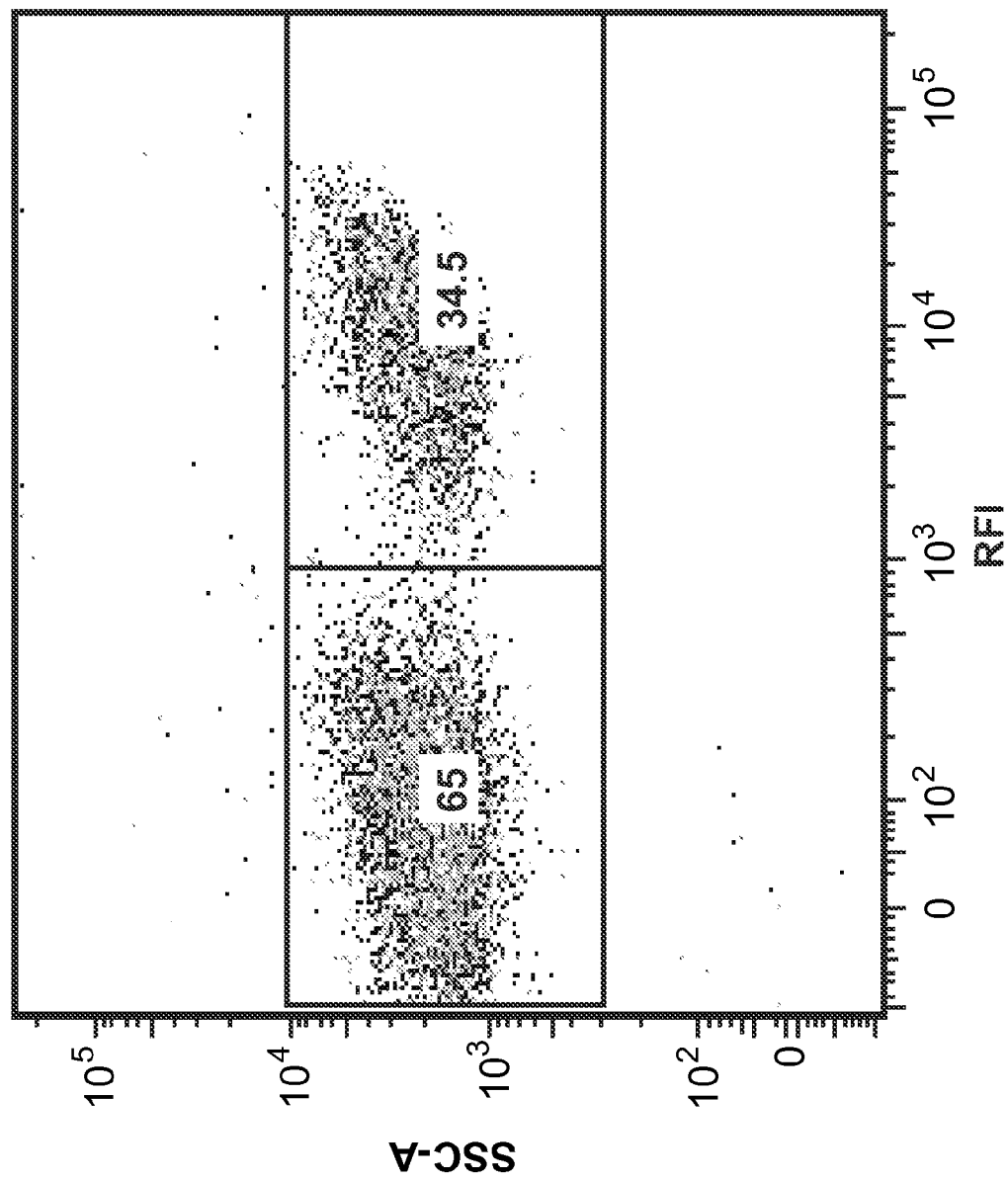
Figure 7:
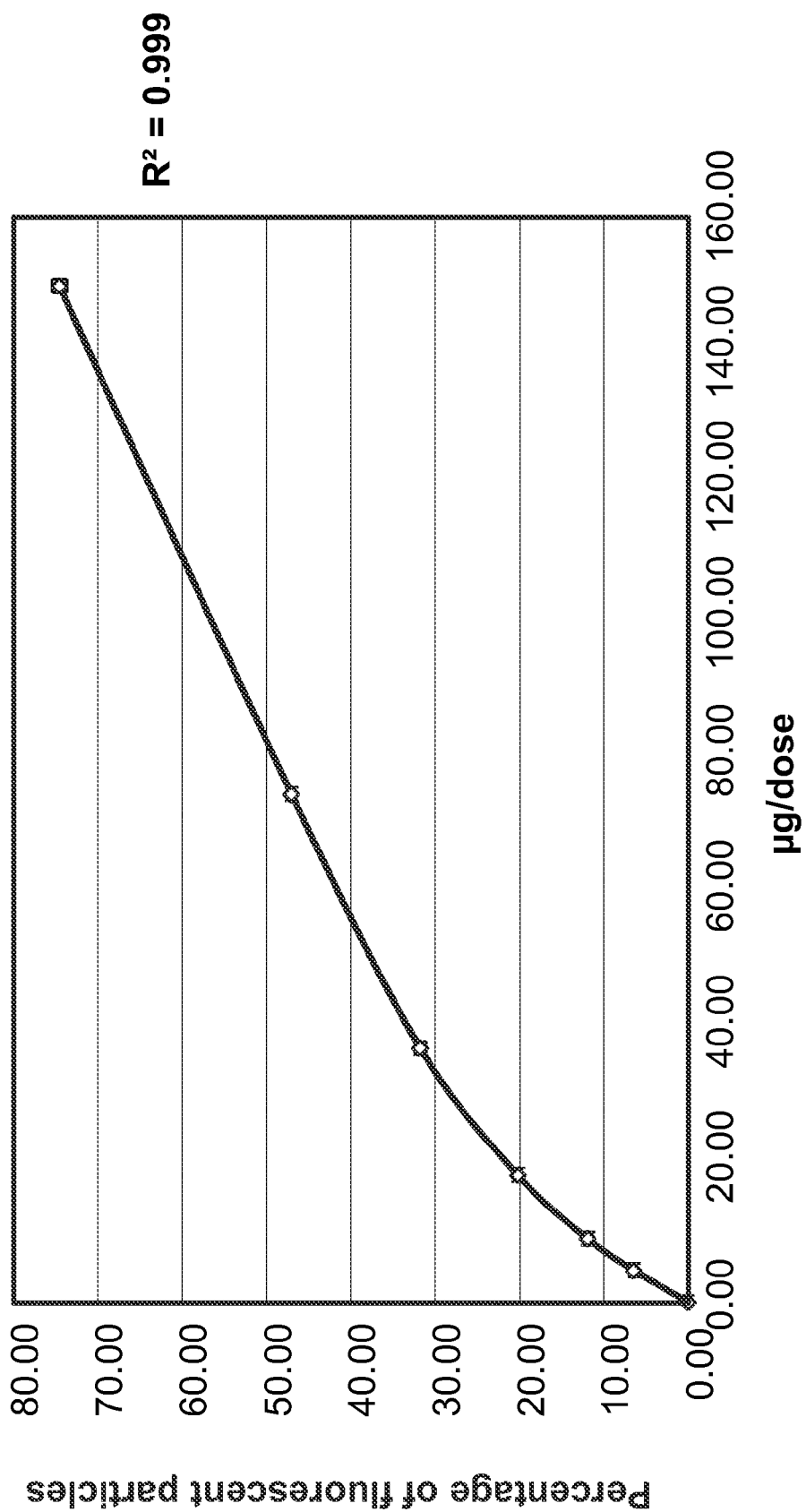
FIG. 7 is a graph of a standard curve of NadA concentration in the flow cytometry assay calculated with three-parameter non-linear regression analysis ($y=ax^3+bx^2+cx$) with correlation coefficients $R^2>0.99$. The y axis displays the percentage of particles with relative fluorescence intensity>1000. Each value represents the mean and standard deviations of triplicate samples performed on three independent experiments. Results showed the detection of the MenB antigen NadA in the range of 3.12-100 µg/dose (6.24-200 µg ml$^{-1}$).

Standard formulations, prepared from a stock solution of 300 µg ml$^{-1}$ for NadA and serially 2-fold diluted five times with aluminium hydroxide suspension, were analyzed by flow cytometry using both forward (FSC) and side scatter (SSC), parameters associated with particle size and morphology respectively. All standard formulations appeared as a single uniform population of particles (FIGS. 4a-4c), with increased concentration of adsorbed NadA having no impact on forward and side scatter measurements. Antigen distribution of NadA on aluminium hydroxide aggregates was analyzed using SSC and relative fluorescence intensity (RFI). The analysis of the RFI revealed that when the suspension had no antigen adsorbed, 99% of the aggregates showed an RFI<1000. However, as the concentration of NadA gradually increased, the fluorescence intensity increased proportionally to the amount of antigen adsorbed (FIG. 5). When aluminium hydroxide particles are loaded with the highest concentration (300 µg ml$^{-1}$) the entire suspension exposed a uniformed fluorescence 23-fold higher than the aluminium hydroxide alone.

Direct Quantification of Adsorbed NadA Antigen in Vaccine Formulation

Standard formulations were prepared in the range of 0-100 µg ml$^{-1}$ and tested by the flow cytometry assay. Standard curves generated by three-parameter non-linear regression analysis had correlation coefficients $R^2$>0.99 (FIGS. 6a-6g). To evaluate the reliability of the standard curves for measuring antigen concentrations, a series of test samples in the same concentration range were assayed and their protein concentration determined from fluorescence readings (Table 3). The results showed that the flow cytometry assay is accurate and reliable with overall percent accuracy of the test formulations in the range of 85% or greater.

Factorial In Vitro Displacement Study

An in vitro displacement study was performed to determine whether the protein BSA, used as the blocking agent, or the primary or secondary antibodies interfere with antigen adsorbed by displacing it from aluminium hydroxide during the assay. The experiment was done in U96-microwell polypropylene plates. Aliquots of 75 µl of a clinical dose sample were mixed with BSA blocking solution, followed by the primary and secondary antibodies. The addition of each reagent was followed by 30 minutes incubation at 4° C., 20 minutes for the secondary antibody, followed by washing steps. After each incubation, the supernatant was kept for further analysis. The presence of the MenB protein in the supernatants was evaluated by SDS-PAGE and the protein was evidenced by western blotting using the same polyclonal antibody used for the assay.

Analysis of Suspensions with More than One Adsorbed Component

Another advantage common to antibody based assays specific for a target antigen is the potential of the assay to be applied directly to complex formulations containing multiple antigens and adjuvants such as combination vaccines. The assay was applied to a trivalent vaccine containing GNA2091-1870 and GNA2132-1030 in addition to NadA, and found no interference of these antigens in determining adsorbed concentrations of NadA.

Discussion

In addition to the accuracy, sensitivity and reproducibility of the flow cytometry assay possesses a number of other key advantages which stem from the fact that as flow cytometry analyses physical particles it is measuring the antigen directly on the surface of the aluminium particles. Firstly the degree of antigen adsorption to aluminium hydroxide is measured directly without the reliance on indirect measurements of unadsorbed antigen in formulation supernatants. Secondly, as the assay may be antibody based, it is possible for flow cytometry to be used to monitor antigen stability whilst still bound to the surface of insoluble metal salt adjuvants. This could be particularly powerful for antigens where protective epitopes have been well defined and in which monoclonal antibodies specific for these regions could be used in the flow cytometry assay to monitor structural integrity of the epitopes over time or to monitor vaccine consistency prior to release. Finally another potential advantage of this assay is that it is able to determine protein concentrations on each insoluble metal salt particle which can reveal the uniformity of antigen distribution in the formulation. With guidelines in the literature (e.g. reference 43) describing different adsorption strategies for the production of multi-component vaccines, flow cytometry based assays could help monitor uniformity of resulting vaccines and importance of antigen distribution on efficacy.

Flow Cytometry Analysis of Adsorbed Small Molecules

Flow cytometry (FC) based technology can be used for the direct detection of SMIPs on aluminium hydroxide with no need for labelling. The assay was tested using a new class of TLR7 agonists which are analogs of the lead compound Compound A. Benzonaphthyridine is the core scaffold of the series and the molecules have intrinsic fluorescence features. Association of SMIPs with aluminium hydroxide transforms plain insoluble metal salt particles into particles that display fluorescent tags, detectable with flow cytometry by combining the light scattering properties with the intensity of fluorescence upon appropriate excitation.

Figure 8:
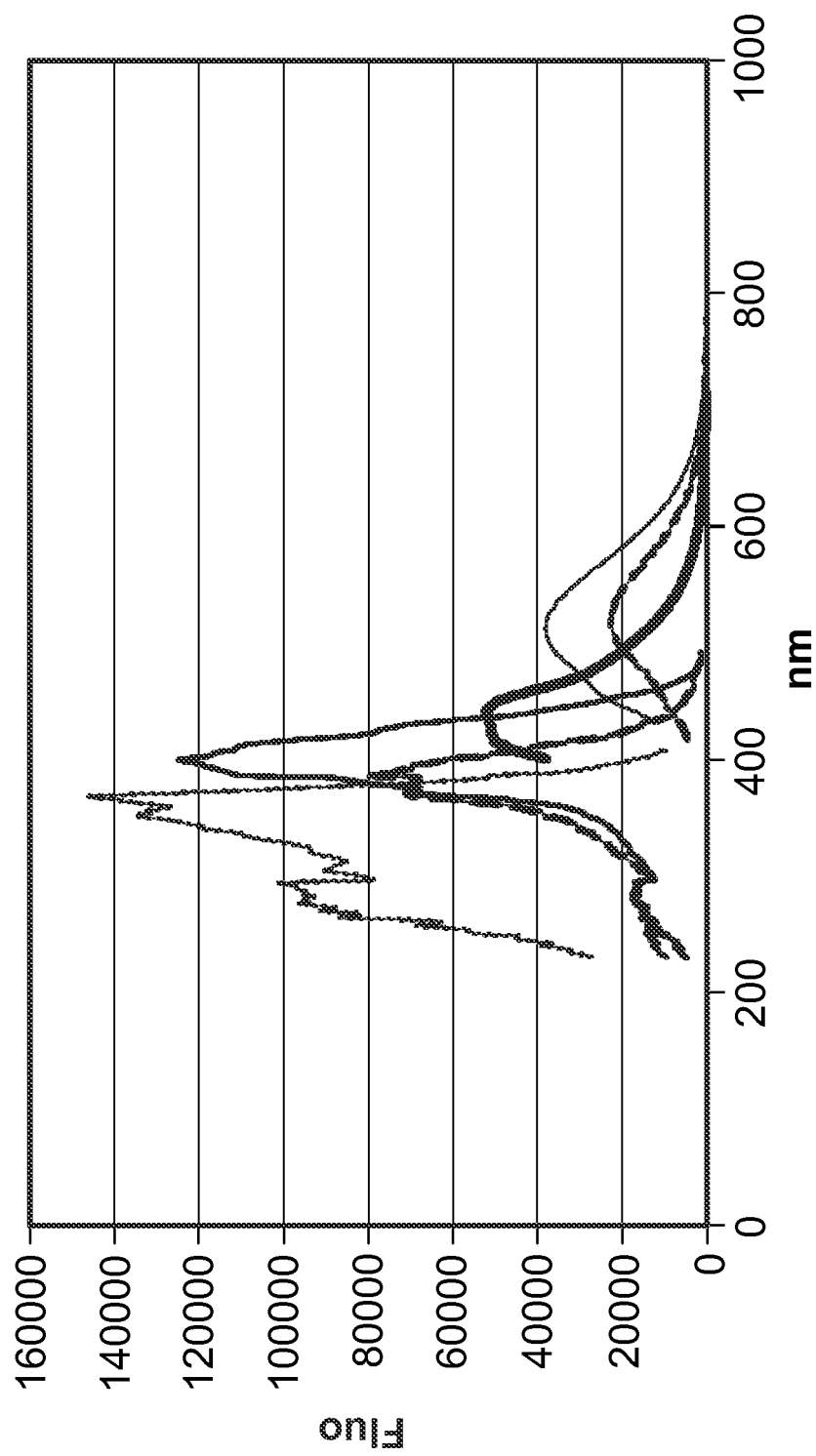
FIG. 8 is a graph showing the excitation profile of a number of SMIPs.
Figure 14:
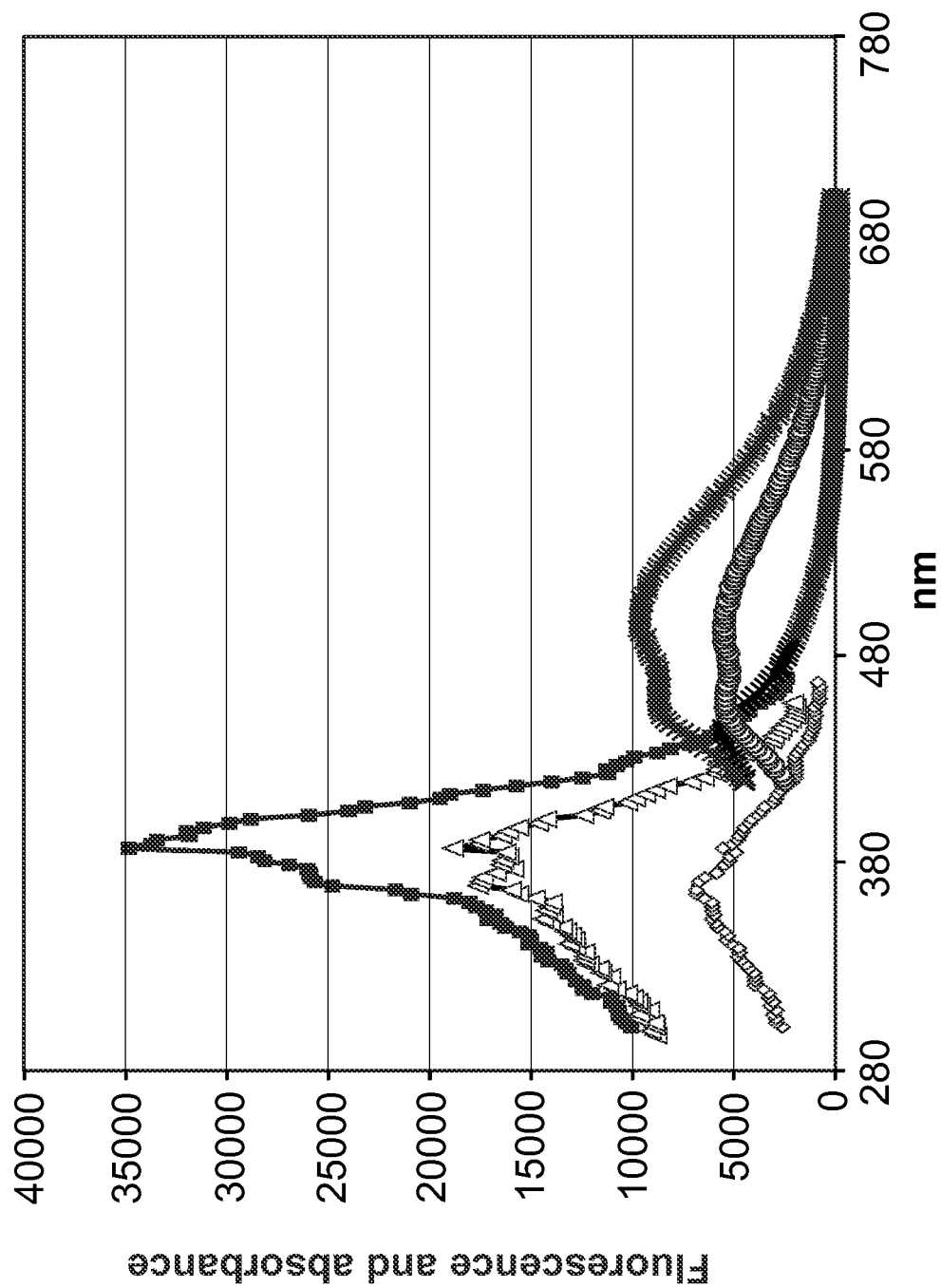
FIG. 14 is a graph showing the excitation profile of two further SMIPs.

Fluorescence spectroscopy confirmed that Compound A, Compound C, Compound B, Compound E and Compound H can be excited in the violet visible spectrum and emit fluorescence in the blue/green visible spectrum with slight differences in wavelength (FIGS. 8 and 14).

Aluminium hydroxide based formulations were analyzed on the FACS Canto II system and characterized by associated morphological parameters (FSC and SSC). Negative controls included aluminium hydroxide alone, small molecule solutions, PBS and Alum-3 MenB vaccine (FIGS. 9a-9d shows the results of these experiments for Compound C).

Aluminium hydroxide alone was gated to cover a homogeneous and compact population, which was based on screening tens of thousands of event to determine light scatter of light emitted by 488 nm blue laser source. Analysis of a solution of Compound C and the PBS control resulted in no detection of particles through light scattering over the background instrumental noise. The gate covered most of the particles of alum (more than 90%) and was applied to all other samples and used to evaluate fluorescence intensity. Filtration of SMIP solutions helped to avoid scatter of precipitated particles or co-precipitation of SMIPs and aluminium hydroxide when formulated together. Aluminium hydroxide alone was gated to cover an homogeneous and compact population (FIG. 10a). The gate was applied to Compound A and no overlapping of light scatter could be found (FIG. 10b). When mixed together they still behave as two different populations (FIG. 10c), in contrast to the single homogenous population observed when Compound C was adsorbed to aluminium hydroxide. Compound E also adsorbed to aluminium hydroxide and behaved as a single population (FIGS. 15a-15d).

Aluminium hydroxide particles included in the applied gate were analyzed for their fluorescence intensity at FACS Canto II using violet laser (405 nm) as excitation source and two different filters for emission: 525/50 nm and 450/50 nm (FIGS. 10a-10c).

Figure 11A:
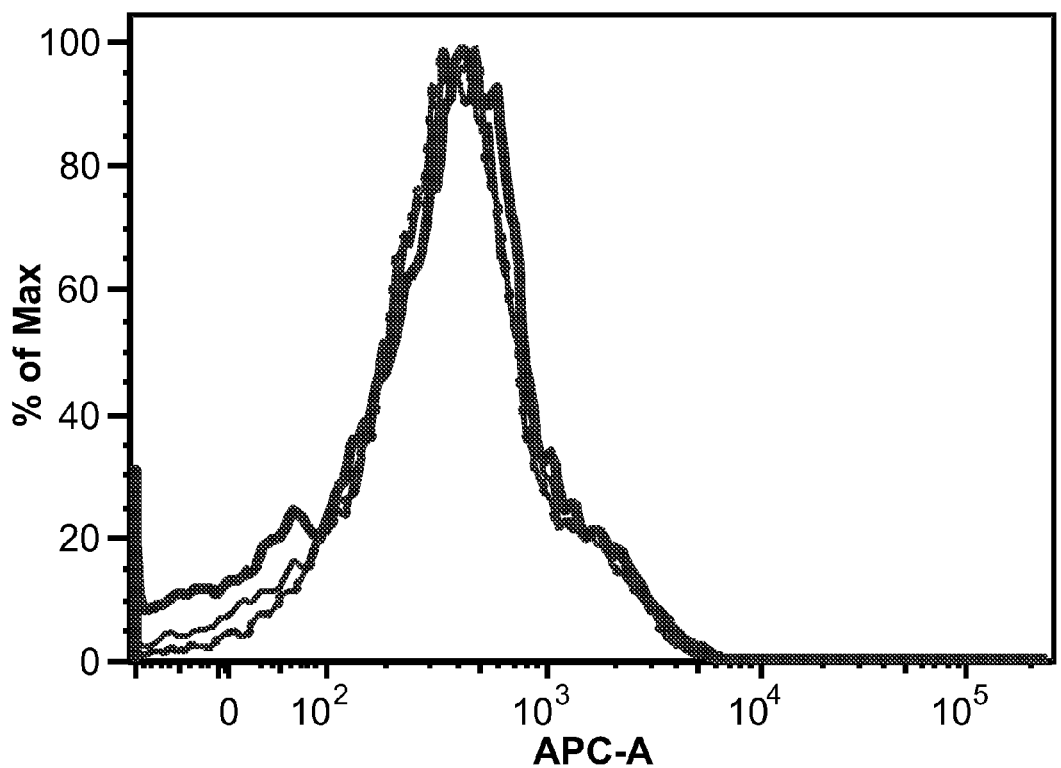
FIGS. 11a-11n show a series of histograms showing the shift of the positive fluorescence peak detected with labeled secondary antibody 961c specific. The shift to the right is directly proportional to amount of 961c adsorbed onto aluminum hydroxide particles adsorbed with 961c only (FIGS. 11a-11g), and when this component was adsorbed as part of a 3-component combination (FIGS. 11h-11n).
Figure 11B:
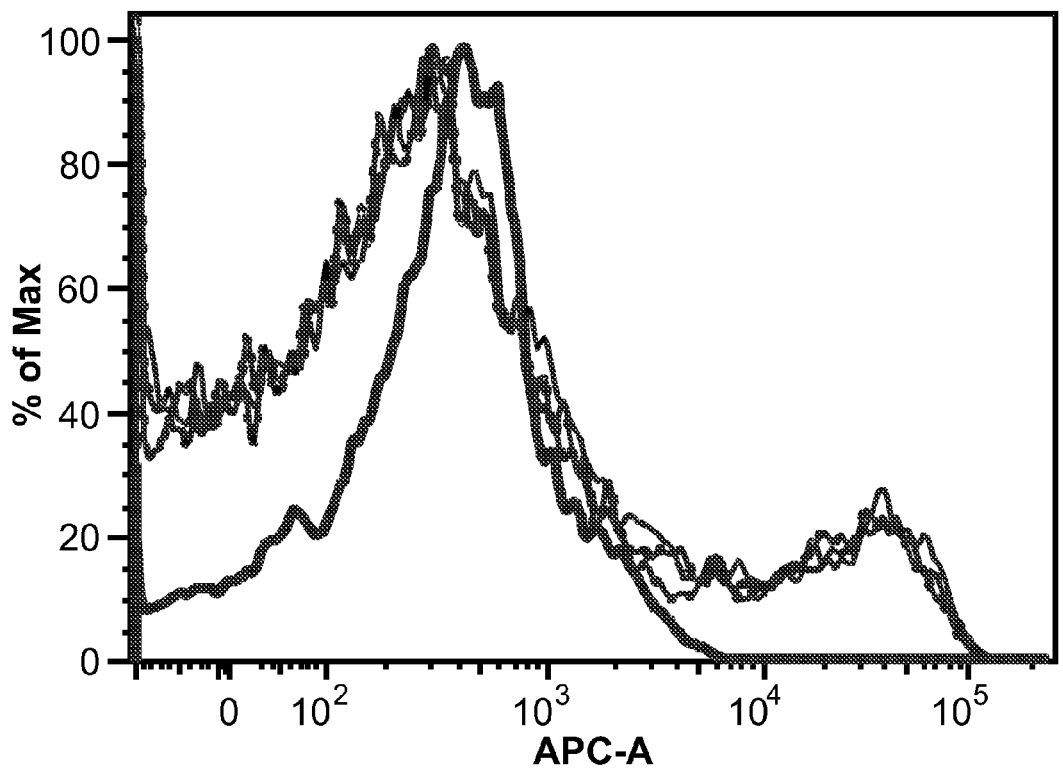
Figure 11C:
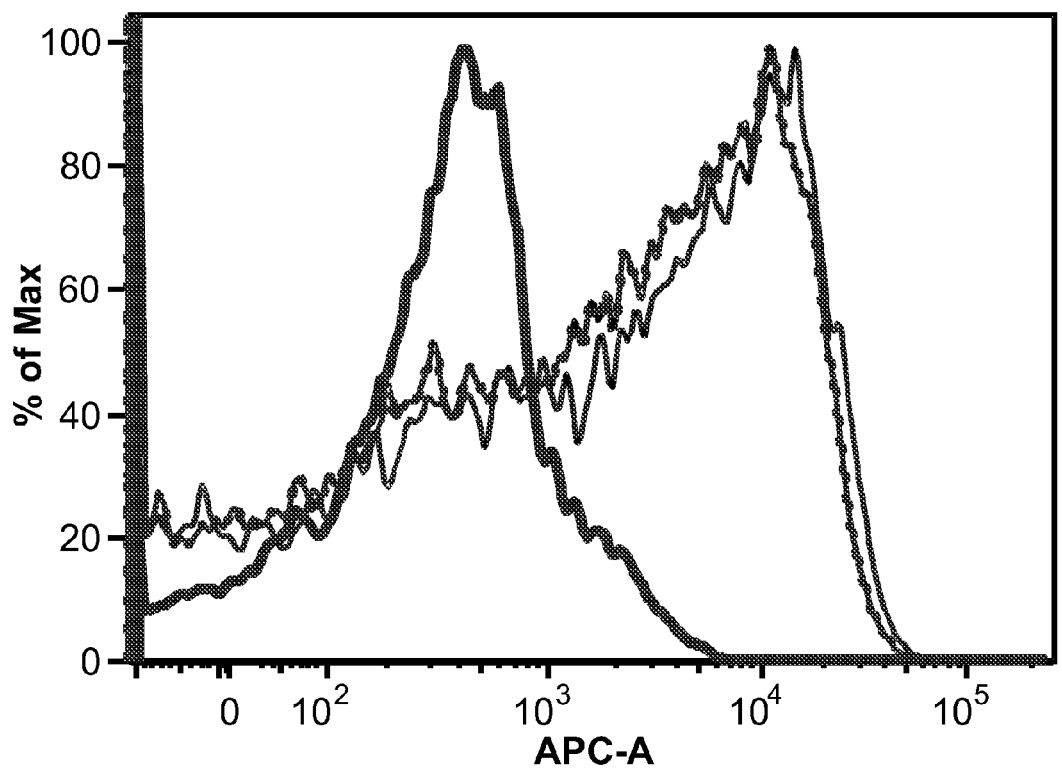
Figure 11D:
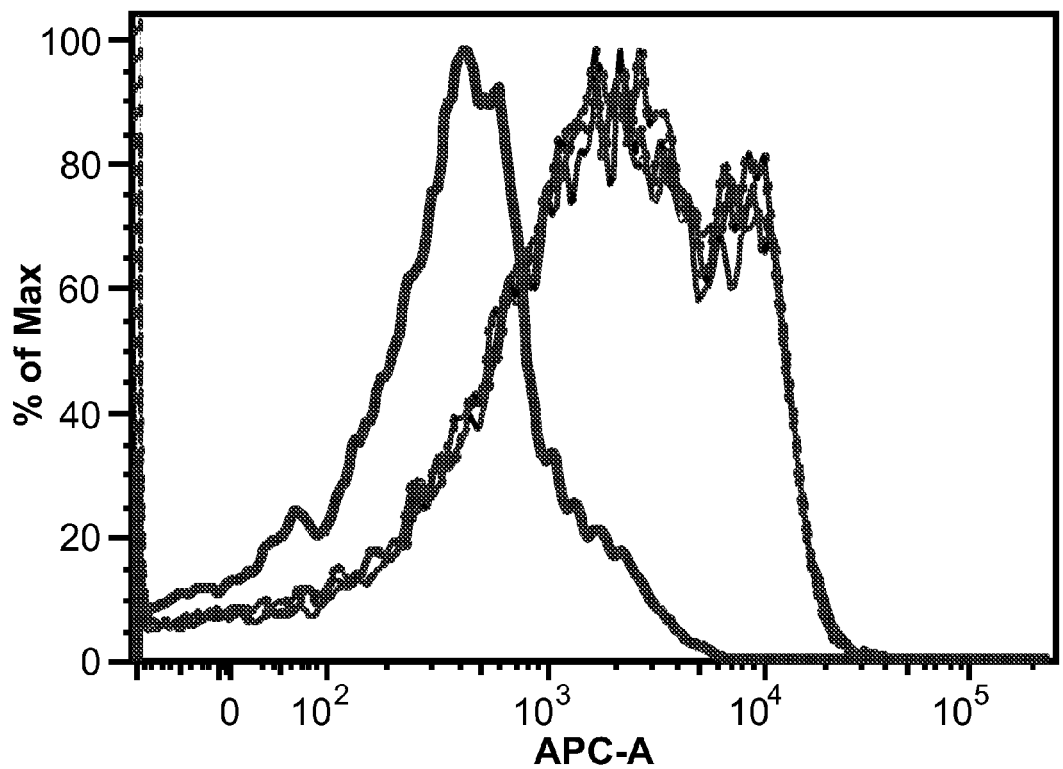
Figure 11E:
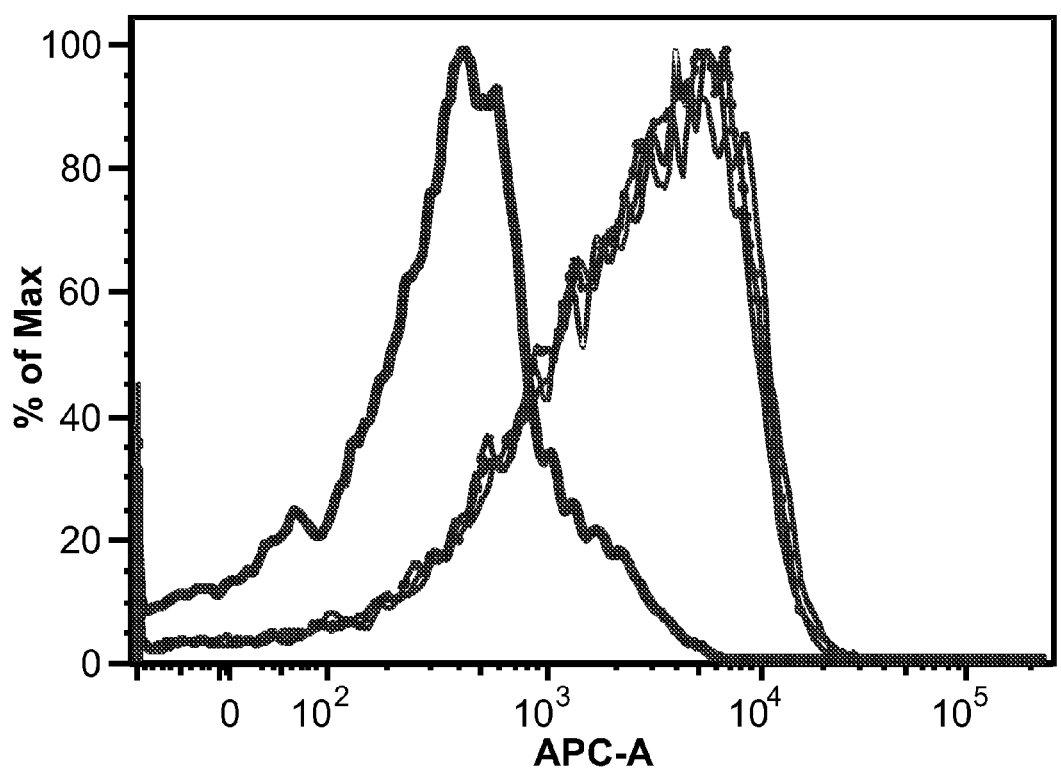
Figure 11F:
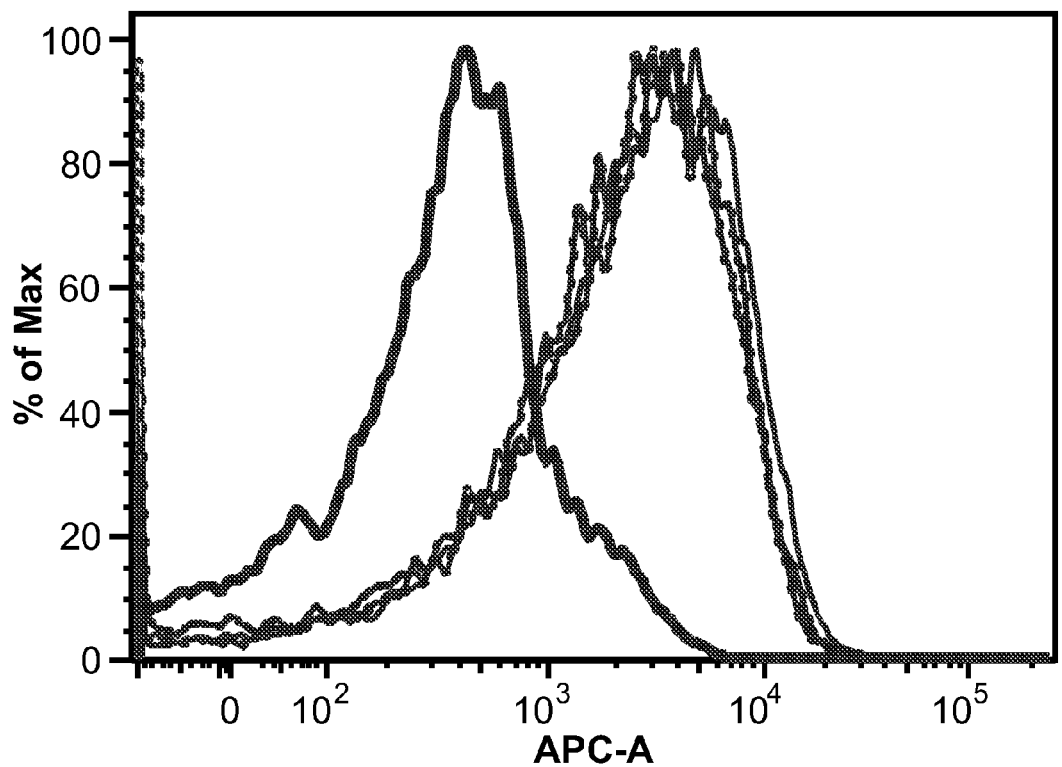
Figure 11G:
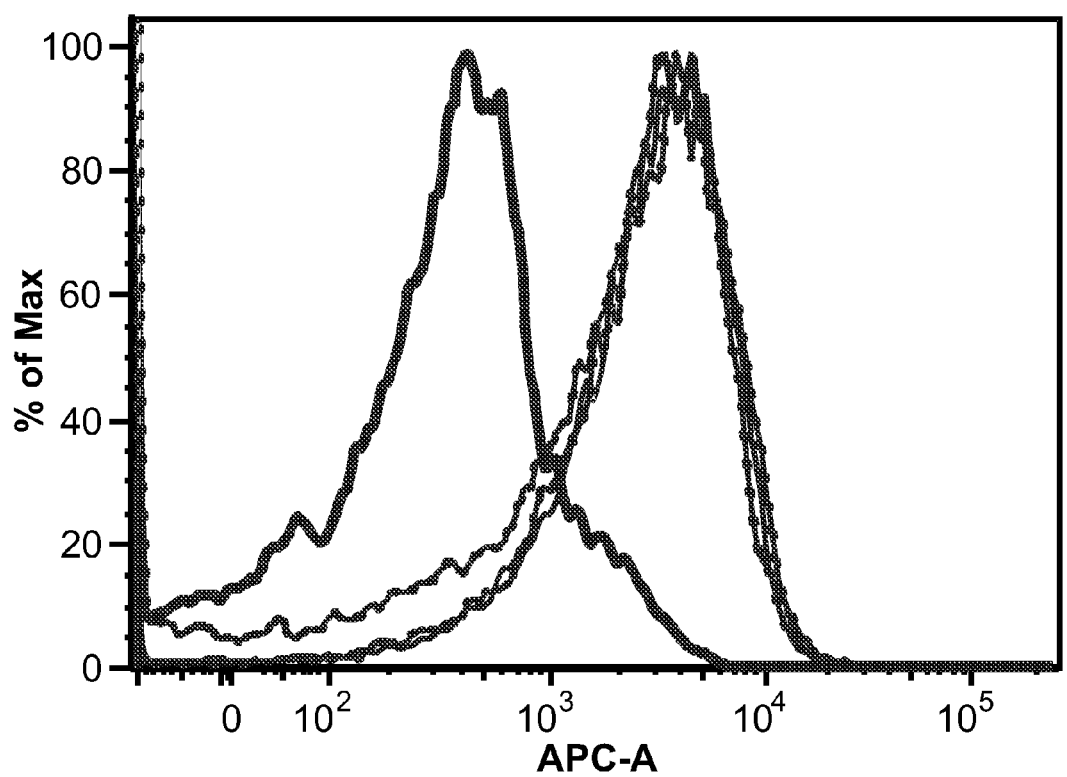
Figure 11H:
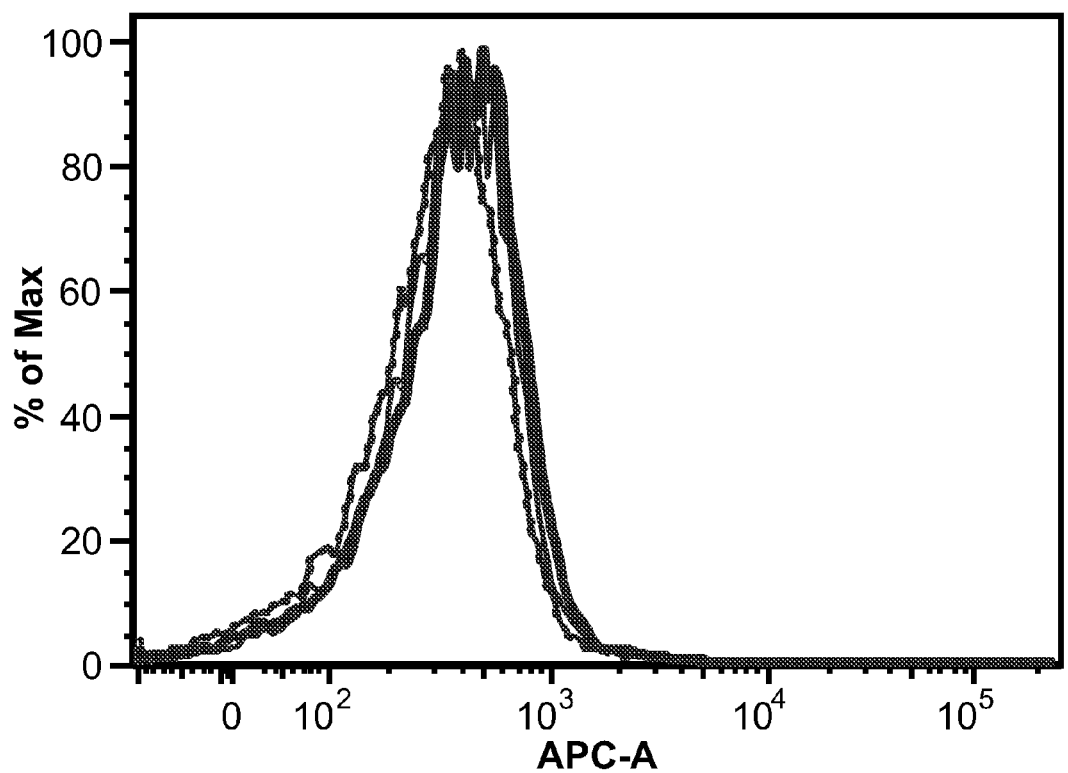
Figure 11I:
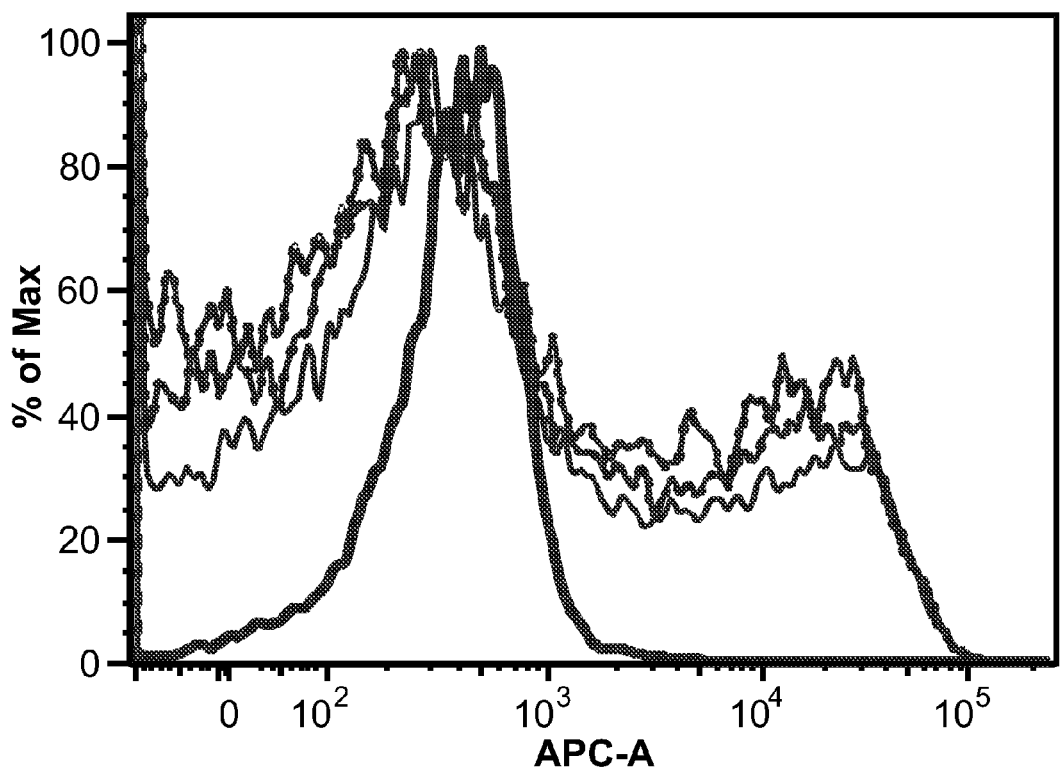
Figure 11J:
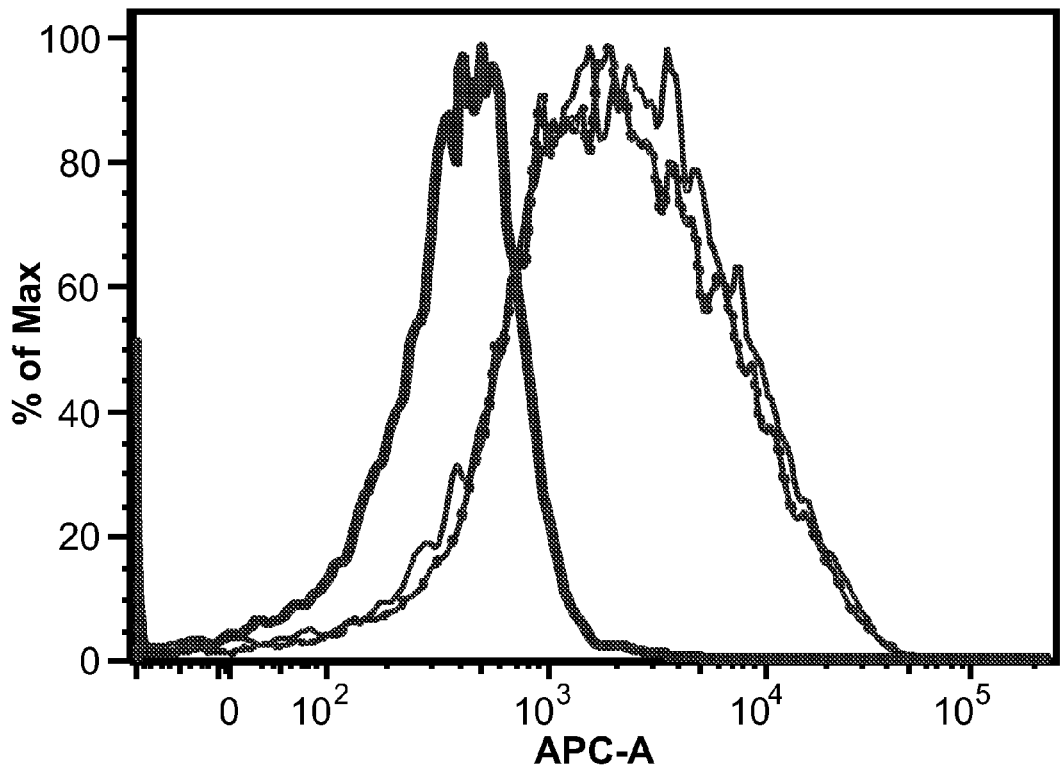
Figure 11K:
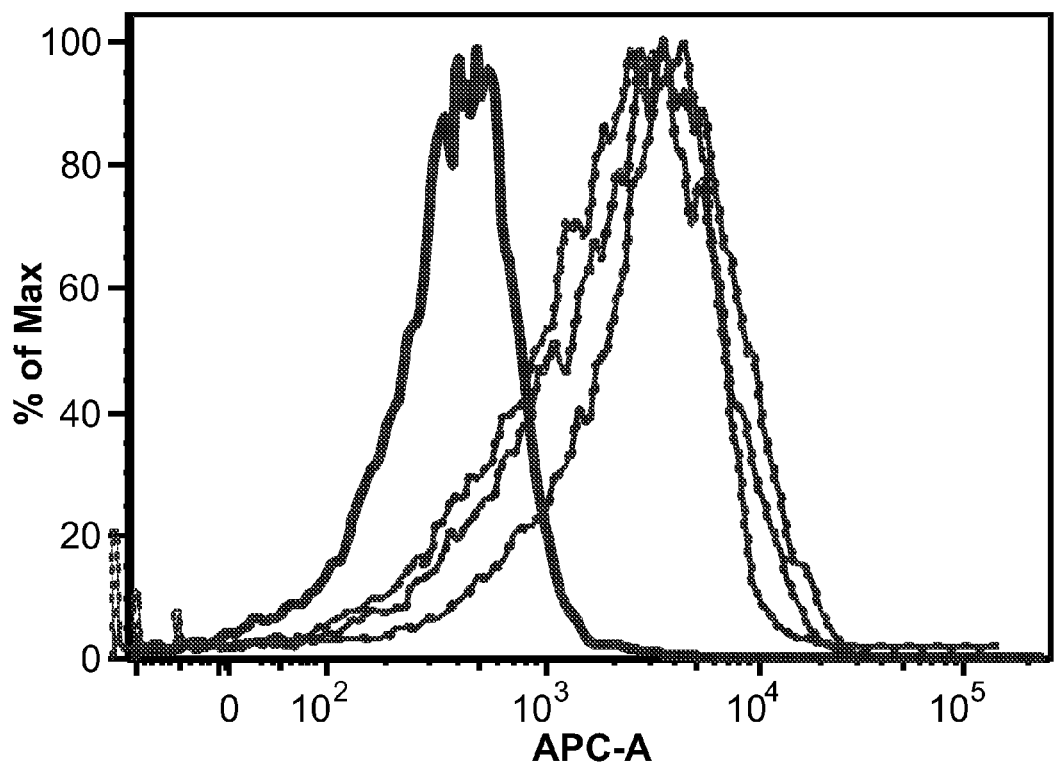
Figure 11L:
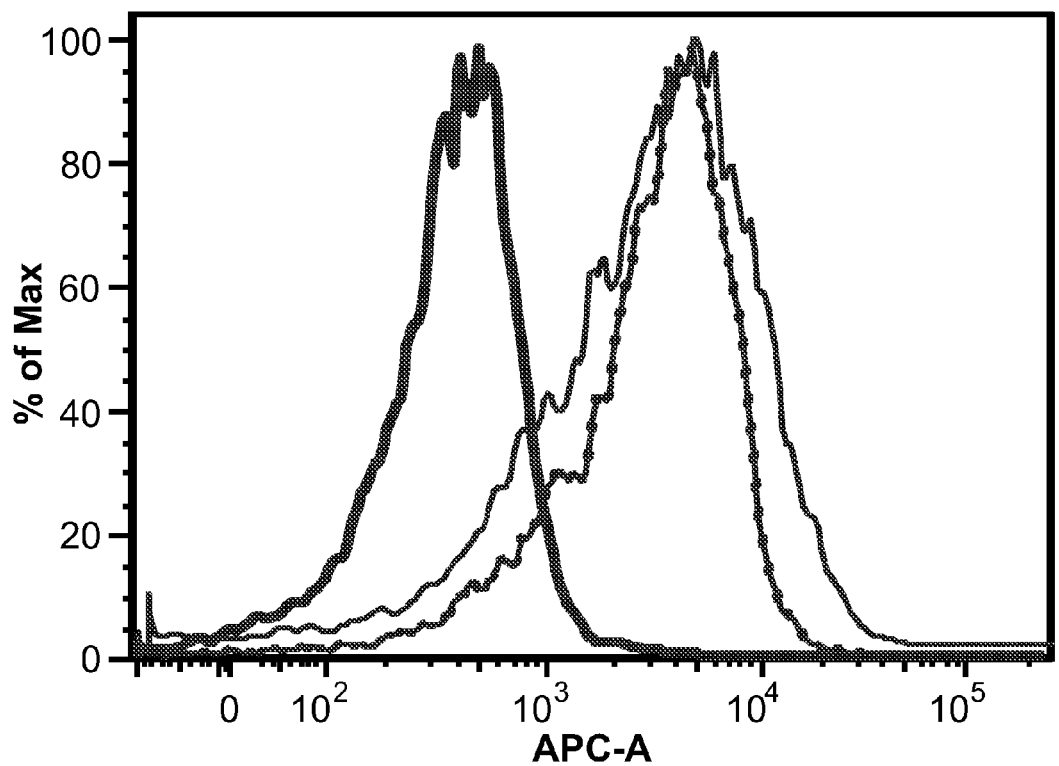
Figure 11M:
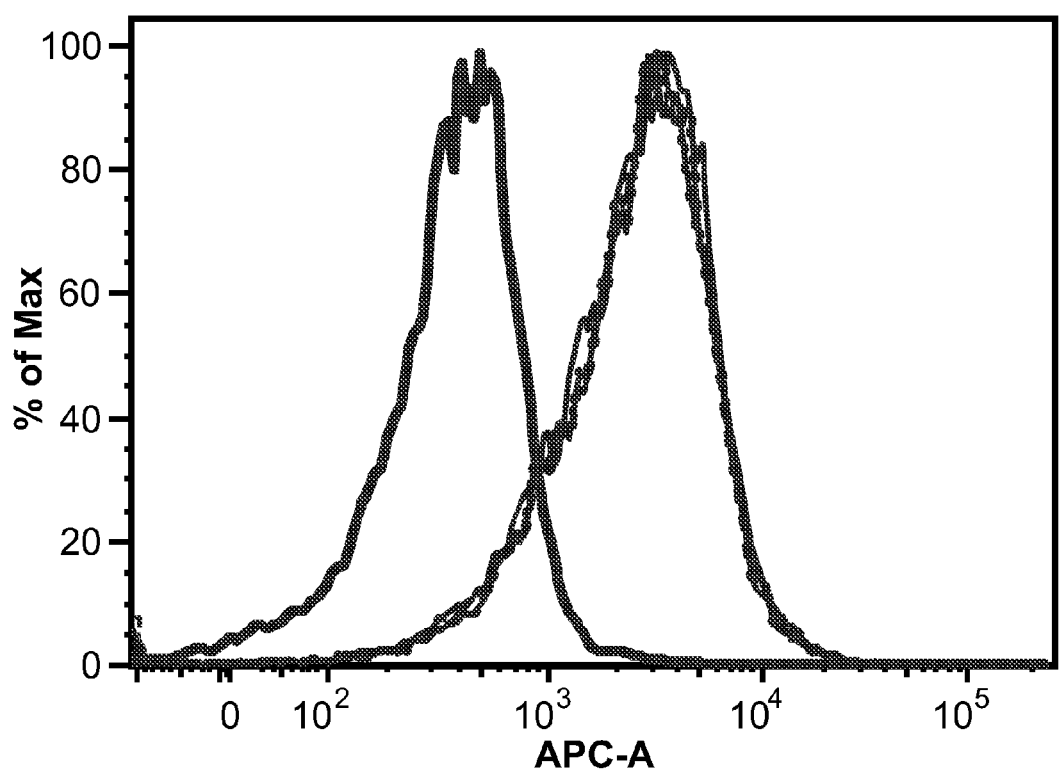
Figure 11N:
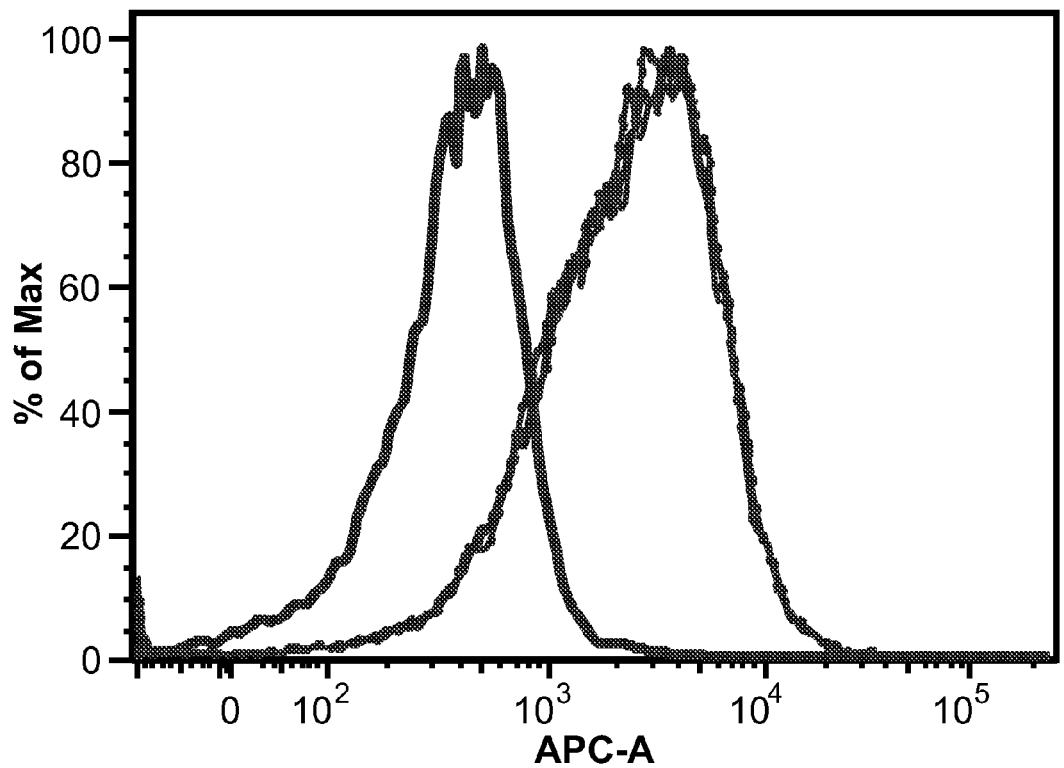

A desorption protocol was used to further confirm binding of SMIPs to aluminium hydroxide. SMIP-aluminium hydroxide formulation was treated with a 0.5M phosphate buffer (pH9) and the desorbed aluminium hydroxide was washed with either water (for soluble compounds) or butanol (for poorly water soluble compounds). The aluminium hydroxide was then analyzed again on FACS Canto II, using the same instrument settings, and showed no fluorescence like aluminium hydroxide alone (FIGS. 11a-11n).

Figure 12A:
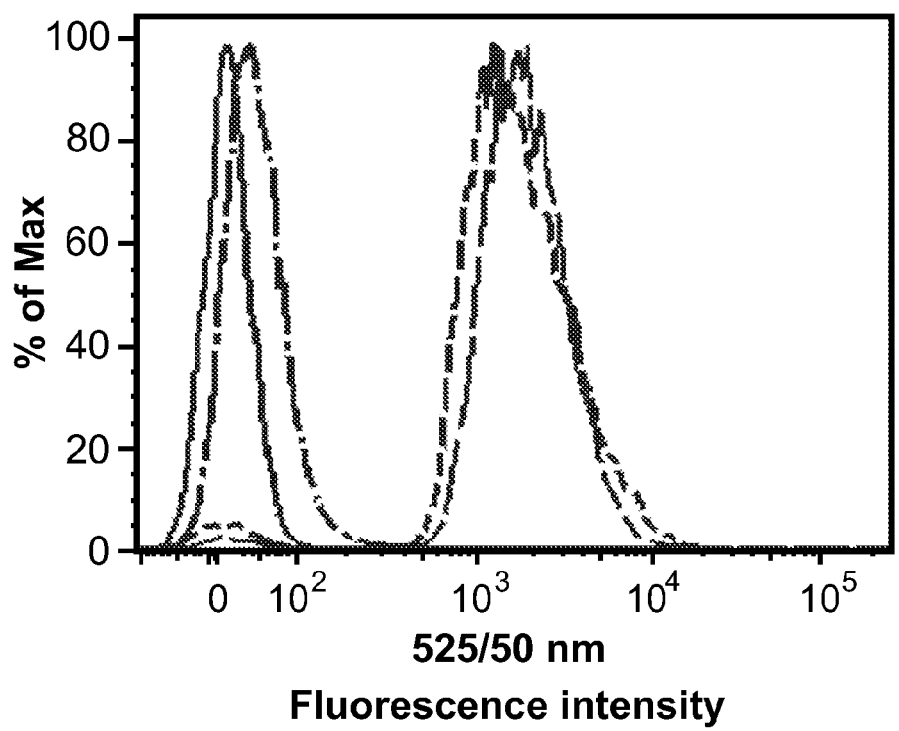
FIGS. 12a-12c are a series of histograms showing fluorescence traces for aluminium hydroxide formulations for (FIG. 12a) Compound B and (FIG. 12b) Compound C. The histograms show increased fluorescence intensity of SMIP-aluminium hydroxide particles (both in the presence and absence of an antigen) with respect to negative controls. This increase is irrespective of whether or not the aluminium hydroxide also has a protein component adsorbed to it. Aluminium hydroxide mixed with Compound A (FIG. 12c), on the contrary, does not show fluorescence as Compound A does not adsorb on aluminium hydroxide particles.
Figure 12B:
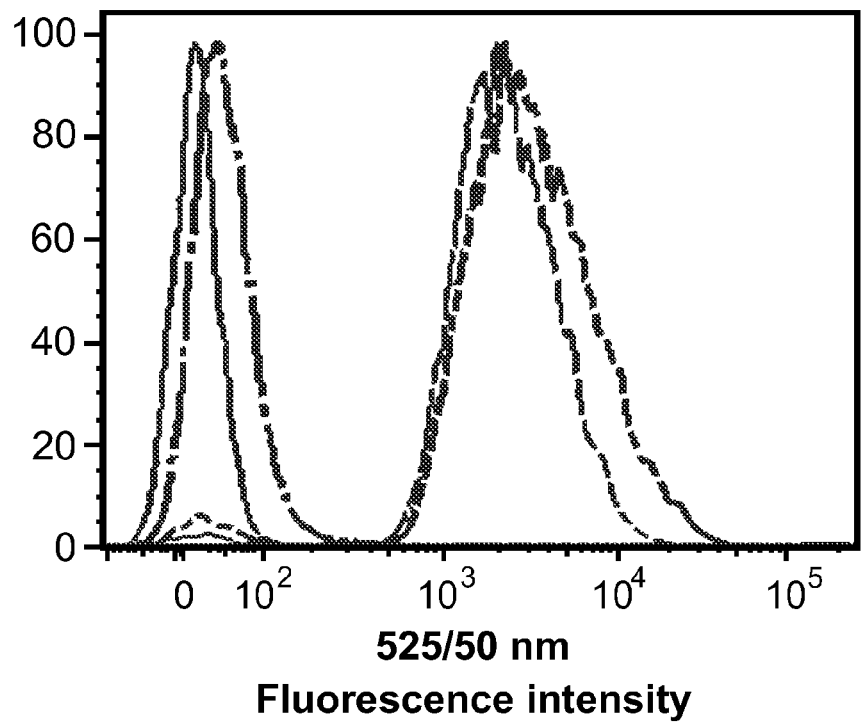
Figure 12C:
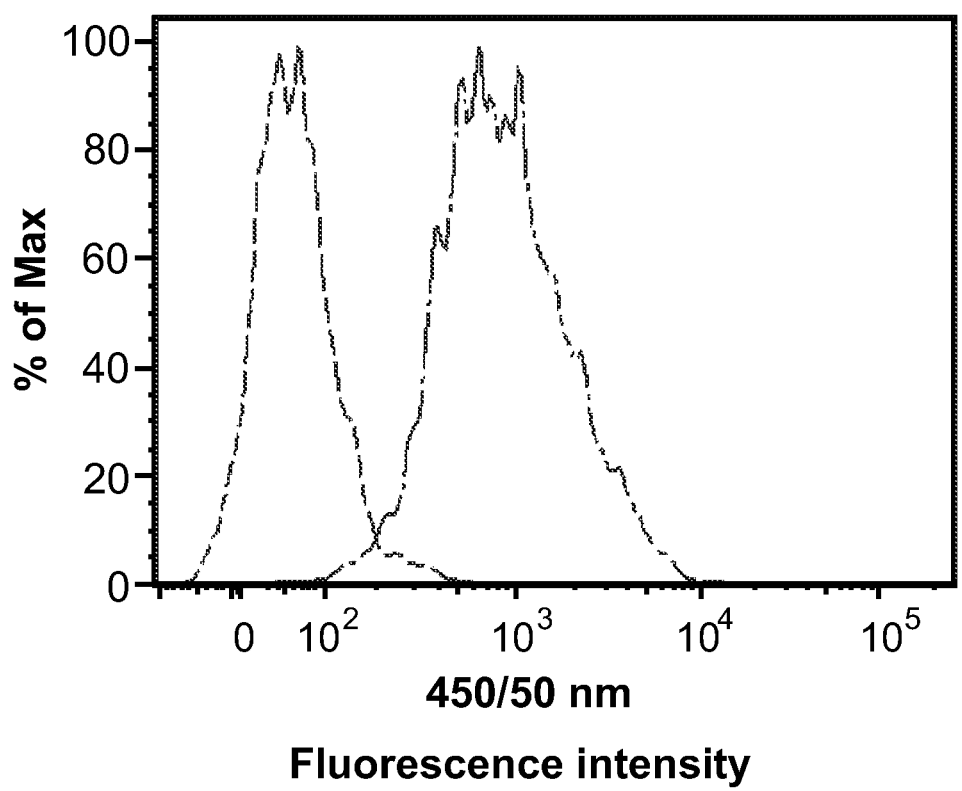
Figure 13A:
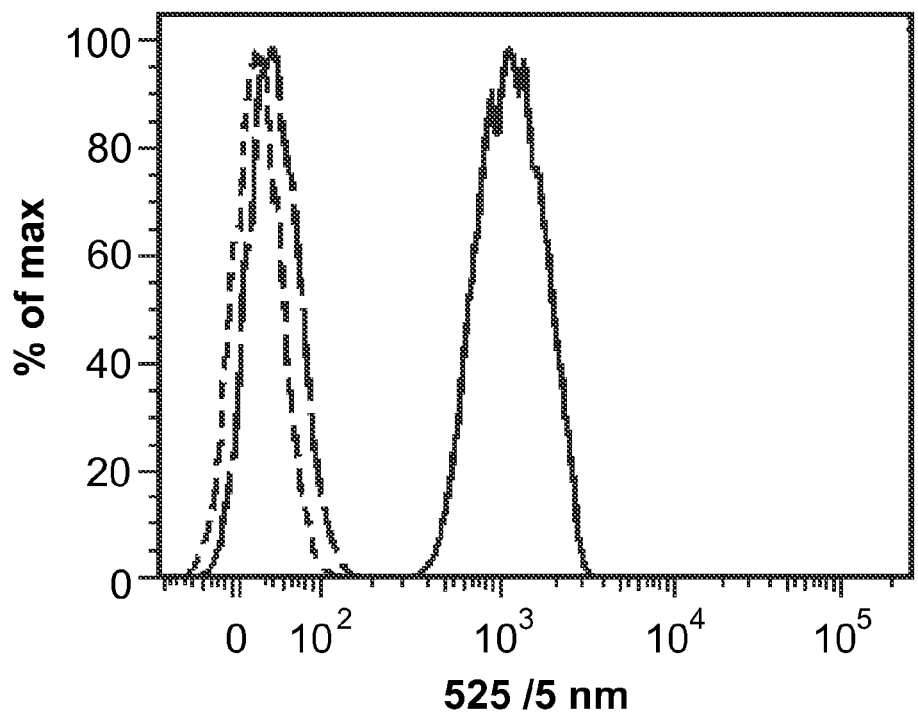
FIG. 13a is a histogram which shows that prior to adsorption and following desorption of SMIP Compound B, aluminium hydroxide particles do not fluoresce in the same manner as when Compound B is adsorbed
Figure 13B:
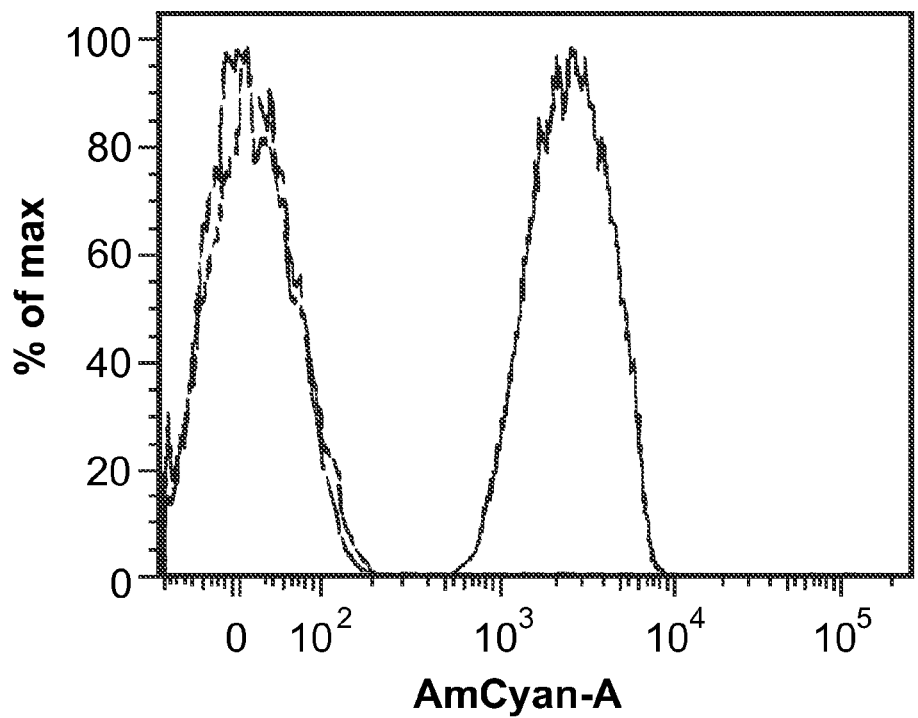
FIG. 13b is a histogram which shows that prior to adsorption and following desorption of SMIP Compound C, aluminium hydroxide particles do not fluoresce in the same manner as when Compound C is adsorbed.

The fluorescence properties of TLR7 SMIPs have been fully exploited to develop a novel assay for the direct detection of SMIPs on aluminium hydroxide. Flow cytometry proved to be a unique tool for the qualitative characterization of SMIP-aluminium hydroxide formulations even in the presence of antigens (see FIGS. 12a & 12b). The adsorption of SMIPs on aluminium hydroxide is well supported by the observation that SMIP-aluminium hydroxide particles have fluorescent features respect to negative control, the light scatter of soluble SMIPs was negligible, the light scatter of insoluble SMIPs (Compound A, not adsorbed on aluminium hydroxide) had different morphology, aluminium hydroxide returns to its negative fluorescence status upon desorption of SMIP. Fluorescence properties were also used to confirm association of SMIPs on aluminium hydroxide via confocal microscopy.

The fluorescence of SMIP can be further exploited to evaluate in vitro SMIP uptake by macrophages via flow cytometry as a powerful tool to understand localization of SMIPs in cells and understand the effect of aluminium hydroxide formulations on the internalization of TLR agonists. Preliminary analyses showed that this type of assay is feasible.

It will be understood that the invention has been described by way of example only and modifications may be made whilst remaining within the scope and spirit of the invention.

TABLE 1

Commonly used fluorescent labels

| Dye | Absorbance Wavelength | Emission Wavelength | Visible colour |
|---|---|---|---|
| Hydroxycoumarin | 325 | 386 | blue |
| methoxycoumarin | 360 | 410 | blue |
| Alexa fluor | 345 | 442 | blue |
| aminocoumarin | 350 | 445 | blue |
| Cy2 | 490 | 510 | green (dark) |
| FAM | 495 | 516 | green (dark) |
| Alexa fluor 488 | 494 | 517 | green (light) |
| Fluorescein FITC | 495 | 518 | green (light) |
| Alexa fluor 430 | 430 | 545 | green (light) |
| Alexa fluor 532 | 530 | 555 | green (light) |
| HEX | 535 | 556 | green (light) |
| Cy3 | 550 | 570 | yellow |
| TRITC | 547 | 572 | yellow |
| Alexa fluor 546 | 556 | 573 | yellow |
| Alexa fluor 555 | 556 | 573 | yellow |
| R-phycoerythrin (PE) | 480; 565 | 578 | yellow |
| Rhodamine Red-X | 560 | 580 | orange |
| Tamara | 565 | 580 | red |
| Cy3.5 581 | 581 | 596 | red |
| Rox | 575 | 602 | red |
| Alexa fluor 568 | 578 | 603 | red |
| Red 613 | 480; 565 | 613 | red |
| Texas Red | 615 | 615 | red |
| Alexa fluor 594 | 590 | 617 | red |
| Alexa fluor 633 | 621 | 639 | red |
| Allophycocyanin | 650 | 660 | red |
| Alexa fluor 633 | 650 | 668 | red |
| Cy5 | 650 | 670 | red |
| Alexa fluor 660 | 663 | 690 | red |
| Cy5.5 | 675 | 694 | red |
| TruRed | 490; 675 | 695 | red |
| Alexa fluor 680 | 679 | 702 | red |
| Cy7 | 743 | 770 | red |

TABLE 2

TLR Agonists

| TLR7 agonist | Structure |
|---|---|
| Compound A | 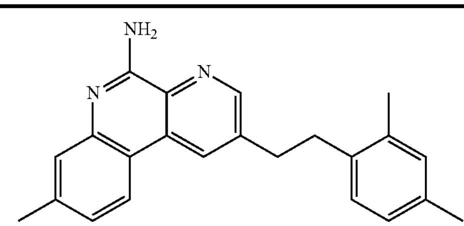 |
| Compound B | 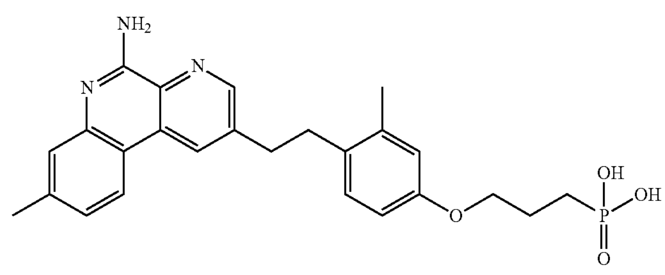 [SMILES: Cc1ccc2c(c1)nc(N)c1ncc(CCc3ccc(OCCCP(=O)(O)O)cc3C)cc12] |
| Compound C | 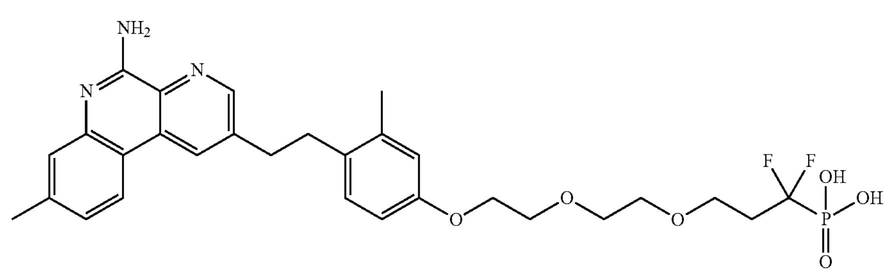 [SMILES: Cc1ccc2c(c1)nc(N)c1ncc(CCc3ccc(OCCOCCOCCC(F)(F)P(=O)(O)O)cc3C)cc12] |

TABLE 2-continued
TLR Agonists
| TLR7 agonist | Structure |
|---|---|
| Compound D | 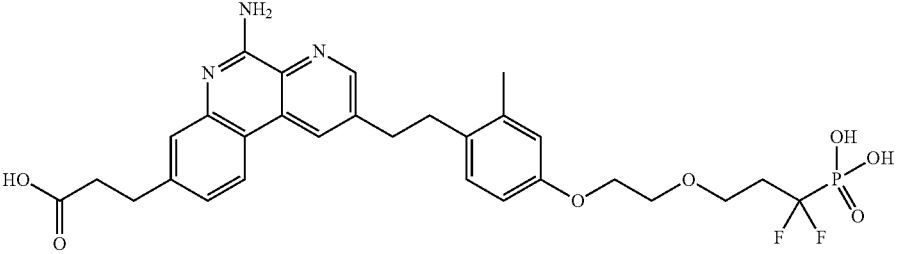 [SMILES: Cc1cc(OCCOCCC(F)(F)P(=O)(O)O)ccc1CCc1cnc2c(N)nc3cc(CCC(=O)O)ccc3c2c1] |
| Compound E | 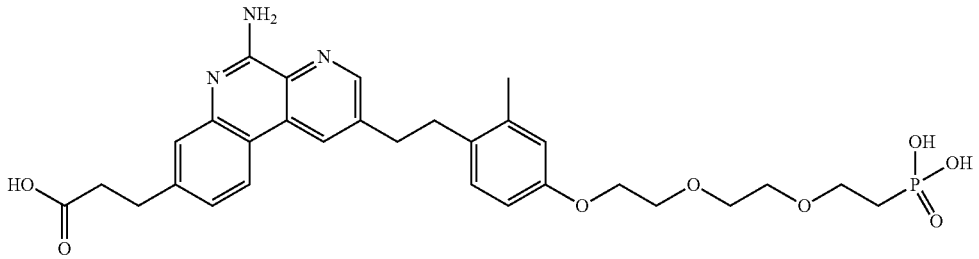 [SMILES: Cc1cc(OCCOCCOCCP(=O)(O)O)ccc1CCc1cnc2c(N)nc3cc(CCC(=O)O)ccc3c2c1] |
|  | 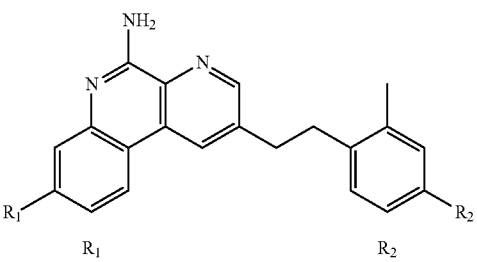 |
|  | R₁          R₂ |
| Compound F | 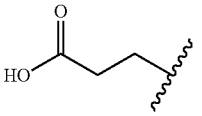 [SMILES: *CCC(=O)O] 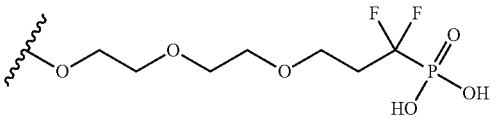 [SMILES: *OCCOCCOCCC(F)(F)P(=O)(O)O] |
| Compound G | 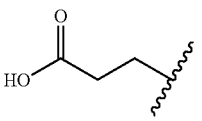 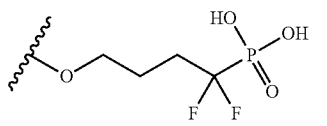 [SMILES: *OCCCC(F)(F)P(=O)(O)O] |
| Compound H | 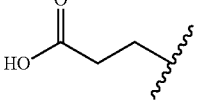 |

TABLE 2-continued

TLR Agonists

| TLR7 agonist | Structure |
|---|---|
| | (structure: linker-O-CH₂CH₂-O-CH₂CH₂-C(F)(F)-P(=O)(OH)(OH)) |

TABLE 3

Comparison of nominal concentration and concentration detected by the flow cytometry assay

| Nominal concentration[a] (μg/500 μl) | Concentration detected[b] (μg/500 μl) | Accuracy[c] (%) | CV[d] (%) |
|---|---|---|---|
| 3.12 | 3.01 +/− 0.1 | 94.8 +/− 2.1 | 4.8 |
| 6.25 | 6.27 +/− 0.3 | 96.4 +/− 2.8 | 4.8 |
| 12.5 | 12.79 +/− 0.2 | 97.6 +/− 1.6 | 1.6 |
| 25 | 24.87 +/− 0.8 | 97.5 +/− 2.0 | 3.4 |
| 50 | 50.5 +/− 2.8 | 94.8 +/− 1.5 | 5.7 |
| 100 | 113.98 +/− 12.3 | 84.7 +/− 10.1 | 10.8 |

[a]Test samples of NadA on Aluminium hydroxide were freshly formulated and diluted to a final concentration with Aluminium hydroxide suspension (3.0 mg/ml)
[b]Back calculation was performed by converting the percentage of fluorescence reading of the standard concentrations of antigen using three-parameter non-linear regression analysis.
[c]% accuracy is percent similarity between the amount of NadA calculated by back calculation (detected by flow cytometry assay) and the known amount of NadA
[d]CV, coefficient of variation between assays, CV is calculated as standard deviation divided by the mean

REFERENCES

[1] WO2004/038417.
[2] Thiele et al. (1990) *J Clin Lab Anal* 4:126-9.
[3] Lai et al. (2008) *Applied Spectroscopy* 62:784-90.
[4] Zhu et al. (2009) *J Immunol Methods* 344:73-8.
[5] *The Molecular Probes® Handbook—A Guide to Fluorescent Probes and Labeling Technologies* (11th Ed.; Invitrogen)
[6] International patent application PCT/IB2010/002386.
[7] *Vaccine Design* . . . (1995) eds. Powell & Newman. ISBN: 030644867X. Plenum.
[8] Treanor et al. (1996) *J Infect Dis* 173:1467-70.
[9] Keitel et al (1996) *Clin Diagn Lab Immunol* 3:507-10.
[10] WO03/097091.
[11] Cassone & Torosantucci (2006) *Expert Rev Vaccines* 5:859-67.
[12] PCT/IB2010/052445.
[13] PCT/IB2010/000998.
[14] Giuliani et al. (2006) *Proc Natl Acad Sci USA*. 103: 10834-9.
[15] WO95/27787.
[16] WO03/010317.
[17] WO2007/110700.
[18] WO2006/138004.
[19] WO2005/084306.
[20] WO2005/002619.
[21] WO03/049762.
[22] WO02/02606.
[23] WO00/37494.
[24] WO2008/020330.
[25] WO2006/091517.
[26] WO2006/089264.
[27] Covacci & Rappuoli (2000) *J. Exp. Med.* 19:587-592.
[28] WO 93/18150.
[29] Covacci et al. (1993) *Proc. Natl. Acad. Sci. USA* 90:5791-5795.
[30] Tummuru et al. (1994) *Infect. Immun.* 61:1799-1809.
[31] Marchetti et al. (1998) *Vaccine* 16:33-37.
[32] Telford et al. (1994) *J. Exp. Med.* 179:1653-1658.
[33] Evans et al. (1995) *Gene* 153:123-127.
[34] WO 96/01272 & WO96/01273, especially SEQ ID NO:6.
[35] WO 97/25429.
[36] *MMWR Morb Mortal Wkly Rep* 1998 Jan. 16; 47(1):12, 19.
[37] Harper et al. (2004) *Lancet* 364(9447):1757-65.
[38] U.S. Pat. No. 6,699,474.
[39] WO2007/060548.
[40] *Remington: The Science and Practice of Pharmacy* (Gennaro, 2000; 20th edition, ISBN: 0683306472).
[41] Ugozzoli et al. (2011) *Analytical Biochemistry* 418: 224-230.
[42] Hem and HogenEsch (2007) *Expert Rev Vaccines* 6:685-698.
[43] Matheis et al. (2001) *Vaccine* 20:67-73.

The invention claimed is:

1. A flow cytometric method for measuring the amount of a component adsorbed to an insoluble metal salt, wherein the measuring comprises the steps of: (i) labelling the adsorbed component with a labelled binding reagent to produce a labelled component; and (ii) measuring the amount of the labelled adsorbed component on the insoluble metal salt particles by flow cytometry.

2. The method according to claim 1 further comprising, before analysis, the step of adsorbing the component to the insoluble metal salt.

3. The method according to claim 1, wherein the labelling step is preceded by a blocking step.

4. The method according to claim 1, wherein the component is a polypeptide antigen.

5. The method according to claim 1, wherein the component is an immunopotentiator.

6. The method according to claim 1, wherein the metal salt is an aluminium salt.

7. The method according to claim 6, wherein the aluminium salt comprises an aluminium hydroxide and/or an aluminium phosphate.

8. The method according to claim 1, wherein the labelled binding reagent comprises an antibody.

9. The method according to claim 8, wherein the labelled binding reagent comprises a primary antibody and a secondary antibody.

10. The method according to claim 1, wherein the labelled binding reagent comprises a fluorophore.

11. A method for analysing the distribution of a component which is adsorbed to an insoluble metal salt particles, comprising steps of: (i) labelling the adsorbed component with a labelled binding reagent to produce a labelled adsorbed component; and (ii) analysing the distribution of the labelled adsorbed component on the insoluble metal salt particles by flow cytometry.

12. The method according to claim 11 further comprising, before analysis, the step of adsorbing the component to the insoluble metal salt particles.

13. The method according to claim 11, wherein the labelling step is preceded by a blocking step.

14. The method according to claim 11, wherein the component is a polypeptide antigen.

15. The method according to claim 11, wherein the component is an immunopotentiator.

16. The method according to claim 11, wherein the metal salt particles are aluminium metal salt particles.

17. The method according to claim 16, wherein the aluminium metal salt particles comprises aluminium hydroxide particles and/or an aluminium phosphate particles.

18. The method according to claim 17, wherein the labelled binding reagent comprises antibody.

19. The method according to claim 18, wherein the labelled binding reagent comprises a primary antibody and a secondary antibody.

20. The method according to claim 11, wherein the labelled binding reagent comprises a fluorophore.

* * * * *